United States Patent
Whayne et al.

(10) Patent No.: US 8,235,990 B2
(45) Date of Patent: *Aug. 7, 2012

(54) VACUUM COAGULATION PROBES

(75) Inventors: James G. Whayne, Chapel Hill, NC (US); Sidney D. Fleischman, Durham, NC (US); Earl Wayne Rogers, Rougemont, NC (US)

(73) Assignee: nContact Surgical, Inc., Morrisville, NC (US)

( * ) Notice: Subject to any disclaimer, the term of this patent is extended or adjusted under 35 U.S.C. 154(b) by 1239 days.

This patent is subject to a terminal disclaimer.

(21) Appl. No.: 11/737,523

(22) Filed: Apr. 19, 2007

(65) Prior Publication Data

US 2007/0250058 A1 Oct. 25, 2007

Related U.S. Application Data

(63) Continuation-in-part of application No. 11/558,420, filed on Nov. 9, 2006, and a continuation-in-part of application No. 11/408,302, filed on Apr. 21, 2006, which is a continuation-in-part of application No. 11/208,465, filed on Aug. 18, 2005, now Pat. No. 7,572,257, which is a continuation-in-part of application No. 10/425,251, filed on Apr. 29, 2003, now Pat. No. 7,063,698, which is a continuation-in-part of application No. 10/172,296, filed on Jun. 14, 2002, now Pat. No. 6,893,442.

(51) Int. Cl.
*A61B 18/14* (2006.01)
(52) U.S. Cl. .......................................... 606/49; 606/41
(58) Field of Classification Search .............. 606/41, 606/42, 45–50; 607/101–105; 604/35
See application file for complete search history.

(56) References Cited

U.S. PATENT DOCUMENTS

| | | | |
|---|---|---|---|
| 4,993,412 A | 2/1991 | Murphy et al. |
| 5,125,928 A | 6/1992 | Parins et al. |
| 5,277,696 A | 1/1994 | Hagen |
| 5,322,064 A | 6/1994 | Lundquist |
| 5,366,490 A | 11/1994 | Edwards et al. |
| 5,562,722 A | 10/1996 | Racz et al. |
| 5,571,088 A | 11/1996 | Lennox et al. |

(Continued)

FOREIGN PATENT DOCUMENTS

JP 2004-500917 1/2004

(Continued)

OTHER PUBLICATIONS

European Patent Application No. 06751099.0 filed Apr. 21, 2006 in the name of Kiser at al., Supplementary European Search Report and European Search Opinion mailed Sep. 3, 2009.

(Continued)

*Primary Examiner* — Michael Peffley
(74) *Attorney, Agent, or Firm* — Levine Bagade Han LLP

(57) ABSTRACT

Methods for using a surgical device integrating a suction mechanism with a coagulation mechanism for improving lesion creation capabilities. The device comprises an elongate member having an insulative covering attached about means for coagulating soft tissue. Openings through the covering expose regions of the coagulation-causing elements and are coupled to lumens in the elongate member which are routed to a vacuum source and a fluid source to passively transport fluid along the contacted soft tissue surface in order to push the maximum temperature deeper into tissue.

38 Claims, 35 Drawing Sheets

U.S. PATENT DOCUMENTS

| | | | |
|---|---|---|---|
| 5,725,523 A | 3/1998 | Mueller | |
| 5,733,280 A | 3/1998 | Avitall | |
| 5,769,847 A | 6/1998 | Panescu et al. | |
| 5,782,760 A | 7/1998 | Schaer | |
| 5,782,828 A | 7/1998 | Chen et al. | |
| 5,785,706 A | 7/1998 | Bednarek | |
| 5,788,681 A | 8/1998 | Weaver et al. | |
| 5,836,311 A | 11/1998 | Borst et al. | |
| 5,851,206 A | 12/1998 | Guglielmi et al. | |
| 5,919,188 A | 7/1999 | Shearon et al. | |
| 5,957,882 A | 9/1999 | Nita et al. | |
| 5,971,983 A | 10/1999 | Lesh | |
| 6,063,081 A | 5/2000 | Mulier et al. | |
| 6,071,279 A | 6/2000 | Whayne et al. | |
| 6,071,281 A | 6/2000 | Burnside et al. | |
| 6,080,151 A | 6/2000 | Swartz et al. | |
| 6,086,583 A * | 7/2000 | Ouchi | 606/41 |
| 6,120,500 A | 9/2000 | Bednarek et al. | |
| 6,161,543 A | 12/2000 | Cox et al. | |
| 6,190,382 B1 | 2/2001 | Ormsby et al. | |
| 6,210,408 B1 | 4/2001 | Chandrasekaran et al. | |
| 6,237,555 B1 | 5/2001 | Dykstra et al. | |
| 6,237,605 B1 | 5/2001 | Vaska et al. | |
| 6,237,606 B1 | 5/2001 | Zikorus et al. | |
| 6,245,062 B1 * | 6/2001 | Berube et al. | 606/33 |
| 6,264,650 B1 | 7/2001 | Hovda et al. | |
| 6,264,654 B1 | 7/2001 | Swartz et al. | |
| 6,296,638 B1 | 10/2001 | Davison et al. | |
| 6,305,378 B1 | 10/2001 | Lesh | |
| 6,311,692 B1 | 11/2001 | Vaska et al. | |
| 6,314,916 B1 | 11/2001 | Watson, Sr. | |
| 6,314,962 B1 | 11/2001 | Vaska et al. | |
| 6,314,963 B1 | 11/2001 | Vaska et al. | |
| 6,325,798 B1 * | 12/2001 | Edwards et al. | 606/41 |
| 6,364,876 B1 | 4/2002 | Erb et al. | |
| 6,425,895 B1 | 7/2002 | Swanson et al. | |
| 6,463,223 B1 | 10/2002 | Karakama et al. | |
| 6,463,332 B1 | 10/2002 | Aldrich | |
| 6,464,699 B1 | 10/2002 | Swanson | |
| 6,474,340 B1 | 11/2002 | Vaska et al. | |
| 6,482,202 B1 | 11/2002 | Goble et al. | |
| 6,484,727 B1 | 11/2002 | Vaska et al. | |
| 6,506,180 B1 | 1/2003 | Lary | |
| 6,514,250 B1 | 2/2003 | Jahns et al. | |
| 6,522,930 B1 | 2/2003 | Schaer et al. | |
| 6,529,778 B2 * | 3/2003 | Prutchi | 607/119 |
| 6,558,382 B2 * | 5/2003 | Jahns et al. | 606/41 |
| 6,579,288 B1 | 6/2003 | Swanson et al. | |
| 6,605,087 B2 | 8/2003 | Swartz et al. | |
| 6,645,200 B1 | 11/2003 | Koblish et al. | |
| 6,645,202 B1 | 11/2003 | Pless et al. | |
| 6,652,518 B2 * | 11/2003 | Wellman et al. | 606/41 |
| 6,663,622 B1 * | 12/2003 | Foley et al. | 606/34 |
| 6,689,128 B2 | 2/2004 | Sliwa, Jr. et al. | |
| 6,701,931 B2 | 3/2004 | Sliwa, Jr. et al. | |
| 6,719,755 B2 | 4/2004 | Sliwa, Jr. et al. | |
| 6,726,684 B1 | 4/2004 | Woloszko et al. | |
| 6,764,487 B2 | 7/2004 | Mulier et al. | |
| 6,849,075 B2 * | 2/2005 | Bertolero et al. | 606/41 |
| 6,887,238 B2 | 5/2005 | Jahns et al. | |
| 6,887,249 B1 | 5/2005 | Houser et al. | |
| 6,893,442 B2 | 5/2005 | Whayne | |
| 6,917,834 B2 | 7/2005 | Koblish et al. | |
| 6,918,908 B2 * | 7/2005 | Bonner et al. | 606/41 |
| 6,949,095 B2 | 9/2005 | Vaska et al. | |
| 7,033,352 B1 | 4/2006 | Gauthier et al. | |
| 7,052,491 B2 | 5/2006 | Erb et al. | |
| 7,063,698 B2 | 6/2006 | Whayne et al. | |
| 7,115,126 B2 | 10/2006 | Berube et al. | |
| 7,144,363 B2 | 12/2006 | Pai et al. | |
| 7,207,988 B2 | 4/2007 | Leckrone et al. | |
| 7,226,448 B2 | 6/2007 | Bertolero et al. | |
| 7,371,233 B2 | 5/2008 | Swanson et al. | |
| 7,387,627 B2 | 6/2008 | Erb et al. | |
| 7,399,300 B2 | 7/2008 | Bertolero et al. | |
| 7,410,487 B2 | 8/2008 | Whayne | |
| 7,572,257 B2 | 8/2009 | Whayne et al. | |
| 7,758,578 B2 | 7/2010 | Whayne et al. | |
| 7,780,661 B2 | 8/2010 | Whayne et al. | |
| 7,803,155 B2 | 9/2010 | Whayne et al. | |
| 2001/0025175 A1 | 9/2001 | Panescu et al. | |
| 2002/0002372 A1 | 1/2002 | Jahns et al. | |
| 2002/0045895 A1 | 4/2002 | Sliwa et al. | |
| 2002/0072739 A1 | 6/2002 | Lee et al. | |
| 2002/0091299 A1 | 7/2002 | Silverman et al. | |
| 2002/0111608 A1 | 8/2002 | Baerveldt et al. | |
| 2002/0133150 A1 | 9/2002 | Whayne et al. | |
| 2002/0138109 A1 | 9/2002 | Keogh et al. | |
| 2002/0193851 A1 | 12/2002 | Silverman et al. | |
| 2003/0109874 A1 | 6/2003 | Dennis | |
| 2003/0114844 A1 | 6/2003 | Ormsby et al. | |
| 2003/0233090 A1 | 12/2003 | Whayne | |
| 2003/0233091 A1 | 12/2003 | Whayne et al. | |
| 2004/0153057 A1 | 8/2004 | Davison et al. | |
| 2004/0186467 A1 | 9/2004 | Swanson et al. | |
| 2004/0220657 A1 | 11/2004 | Nieminen et al. | |
| 2005/0004516 A1 | 1/2005 | Vanney | |
| 2005/0045895 A1 | 3/2005 | Emerson et al. | |
| 2005/0119545 A1 | 6/2005 | Swanson | |
| 2005/0149152 A1 | 7/2005 | Bertolero et al. | |
| 2005/0240175 A1 | 10/2005 | Bertolero et al. | |
| 2005/0288666 A1 | 12/2005 | Bertolero et al. | |
| 2006/0004388 A1 | 1/2006 | Whayne et al. | |
| 2006/0009762 A1 | 1/2006 | Whayne | |
| 2006/0015165 A1 | 1/2006 | Bertolero et al. | |
| 2006/0122680 A1 | 6/2006 | Auth et al. | |
| 2006/0184167 A1 | 8/2006 | Vaska et al. | |
| 2006/0200124 A1 | 9/2006 | Whayne et al. | |
| 2006/0206113 A1 | 9/2006 | Whayne et al. | |
| 2006/0235381 A1 | 10/2006 | Whayne et al. | |
| 2006/0293646 A1 | 12/2006 | Whayne et al. | |
| 2007/0005051 A1 | 1/2007 | Kampa | |
| 2007/0043351 A1 | 2/2007 | Fleischman et al. | |
| 2007/0083082 A1 | 4/2007 | Kiser et al. | |
| 2007/0083225 A1 | 4/2007 | Kiser et al. | |
| 2007/0156185 A1 | 7/2007 | Swanson et al. | |
| 2007/0239155 A1 | 10/2007 | Ibrahim et al. | |
| 2007/0249991 A1 | 10/2007 | Whayne et al. | |
| 2008/0114342 A1 | 5/2008 | Whayne et al. | |
| 2008/0114354 A1 | 5/2008 | Whayne et al. | |
| 2008/0114355 A1 | 5/2008 | Whayne et al. | |
| 2008/0243119 A1 | 10/2008 | Whayne et al. | |
| 2009/0254009 A1 | 10/2009 | Whayne et al. | |
| 2010/0262138 A1 | 10/2010 | Whayne et al. | |

FOREIGN PATENT DOCUMENTS

| | | |
|---|---|---|
| JP | 2005-512668 | 5/2005 |
| WO | WO 01/58373 | 8/2001 |
| WO | WO 01/80755 | 11/2001 |
| WO | WO 03/053259 | 7/2003 |
| WO | WO 2004/028233 | 6/2004 |
| WO | WO 2004/93698 | 11/2004 |
| WO | WO 2005/046456 | 5/2005 |

OTHER PUBLICATIONS

European Patent Application No. 06751099.0 filed Apr. 21, 2006 in the name of Kiser at al., office action mailed Nov. 16, 2009.

International Patent Application No. PCT/US2006/015268 filed Apr. 21, 2006 in the name of Kiser et al., International Search Report and Written Opinion mailed Oct. 3, 2007.

International Patent Application No. PCT/US2006/060749 in the name of Whayne et al. filed Nov. 9, 2006, International Search Report and Written Opinion mailed Nov. 21, 2007.

International Patent Application No. PCT/US2009/040981 in the name of Sicvol filed Apr. 17, 2009, International Search Report and Written Opinion mailed Jun. 11, 2009.

International Patent Application No. PCT/US2009/046780 in the name of Whayne et al. filed Jun. 9, 2009, International Search Report and Written Opinion mailed Jul. 28, 2009.

U.S. Appl. No. 11/155,305, filed Jun. 17, 2005 in the name of Whayne et al., Final Office Action mailed Aug. 13, 2009.

U.S. Appl. No. 11/155,305, filed Jun. 17, 2005 in the name of Whayne et al., Non-final Office Action mailed Oct. 28, 2008.

U.S. Appl. No. 11/155,338, filed Jun. 17, 2005 in the name of Whayne et al., Final Office Action mailed Dec. 8, 2009.

U.S. Appl. No. 11/155,338, filed Jun. 17, 2005 in the name of Whayne et al., Non-final Office Action mailed Feb. 17, 2009.

U.S. Appl. No. 11/408,302, filed Apr. 21, 2006 in the name of Fleischman, Non-final Office Action mailed Nov. 3, 2009.

U.S. Appl. No. 11/408,307, filed Apr. 21, 2006 in the name of Kiser et al., Non-final Office Action mailed Sep. 17, 2009.

U.S. Appl. No. 11/408,315, filed Apr. 21, 2006 in the name of Kiser et al., Non-final Office Action mailed Sep. 22, 2009.

U.S. Appl. No. 11/419,840, filed May 23, 2006 in the name of Whayne, Non-final Office Action mailed Dec. 3, 2008.

U.S. Appl. No. 11/432,962, filed May 12, 2006 in the name of Whayne, Non-final Office Action mailed Dec. 3, 2008.

Cragg et al. "Endovascular Diathermic Vessel Occlusion", Radiology 1982, vol. 144, pp. 303-308.

Gorisch et al. "Heat-Induced Contraction of Blood Vessels", Lasers in Surgery and Medicine 1982, vol. 2, pp. 1-13.

Nath et al. "Cellular Electrophysiologic Effects of Hyperthermia on Isolated Guinea Pig Papillary Muscle: Implications for Catheter Ablation", Circulation 1993, vol. 88, pp. 1826-1831.

U.S. Appl. No. 11/558,423, filed Nov. 9, 2006 in the name of Whayne et al., final Office Action mailed Apr. 27, 2010.

U.S. Appl. No. 11/408,302, filed Apr. 21, 2006 in the name of Fleischman et al., non-final Office Action mailed Nov. 3, 2009.

U.S. Appl. No. 11/558,420, filed Nov. 9, 2006 in the name of Whayne et al., non-final Office Action mailed May 12, 2010.

U.S. Appl. No. 11/432,962, filed May 12, 2006 in the name of Whayne, Non-final Office Action mailed Apr. 21, 2010.

U.S. Appl. No. 11/419,840, filed May 23, 2006 in the name of Whayne, final Office Action mailed Apr. 21, 2010.

Cragg, et al., "Endovascular diathermic vessel occlusion," *Radiology*, 144:303-308, 1982.

Gorisch et al., "Heat-induced contraction of blood vessels," *Lasers in Surgery and Medicine*, 2:1-13, 1982.

Nath, et al., "Cellular electrophysiologic effects of hyperthermia on isolated guinea pig papillary muscle: implications for catheter ablation," *Circulation*, 88:1826-1831, 1993.

International Patent Application No. PCT/US2006/015009 in the name of Fleischman et al. filed Apr. 21, 2006, International Search Report and Written Opinion mailed Sep. 27, 2006.

International Patent Application No. PCT/US2006/060753 in the name of Whayne et al. filed Nov. 9, 2006, International Search Report and Written Opinion mailed Dec. 3, 2007.

U.S. Appl. No. 10/172,296, filed Jun. 14, 2002 in the name of Whayne, Non-Final Office Action mailed Oct. 17, 2003.

U.S. Appl. No. 10/172,296, filed Jun. 14, 2002 in the name of Whayne, Notice of Allowance mailed Jul. 23, 2004.

U.S. Appl. No. 10/425,251, filed Apr. 29, 2003 in the name of Whayne, Final Office Action mailed Nov. 14, 2005.

U.S. Appl. No. 10/425,251, filed Apr. 29, 2003 in the name of Whayne, Non-final Office Action mailed Jan. 20, 2006.

U.S. Appl. No. 10/425,251, filed Apr. 29, 2003 in the name of Whayne, Non-final Office Action mailed May 25, 2005.

U.S. Appl. No. 10/425,251, filed Apr. 29, 2003 in the name of Whayne, Notice of Allowance mailed Apr. 12, 2006.

U.S. Appl. No. 11/096,205, filed Mar. 30, 2005 in the name of Whayne, Non-final Office Action mailed Sep. 19, 2007.

U.S. Appl. No. 11/096,205, filed Mar. 30, 2005 in the name of Whayne, Notice of Allowance mailed May 1, 2008.

U.S. Appl. No. 11/208,465, filed Aug. 18, 2008 in the name of Whayne et al., Final Office Action mailed Jan. 7, 2009.

U.S. Appl. No. 11/208,465, filed Aug. 18, 2008 in the name of Whayne et al., Non-final Office Action mailed Jul. 29, 2008.

U.S. Appl. No. 11/208,465, filed Aug. 18, 2008 in the name of Whayne et al., Notice of Allowance mailed Jun. 11, 2009.

U.S. Appl. No. 11/419,840, filed May 23, 2006 in the name of Whayne, Non-final Office Action mailed Aug. 31, 2009.

U.S. Appl. No. 11/432,962, filed May 12, 2006 in the name of Whayne, Non-final Office Action mailed Sep. 1, 2009.

U.S. Appl. No. 11/433,248, filed May 12, 2006 in the name of Whayne, Non-final Office Action mailed Jan. 5, 2009.

U.S. Appl. No. 11/433,248, filed May 12, 2006 in the name of Whayne, Non-final Office Action mailed Sep. 3, 2009.

U.S. Appl. No. 11/558,423, filed Nov. 9, 2006 in the name of Whayne et al., Non-final Office Action mailed Aug. 19, 2009.

* cited by examiner

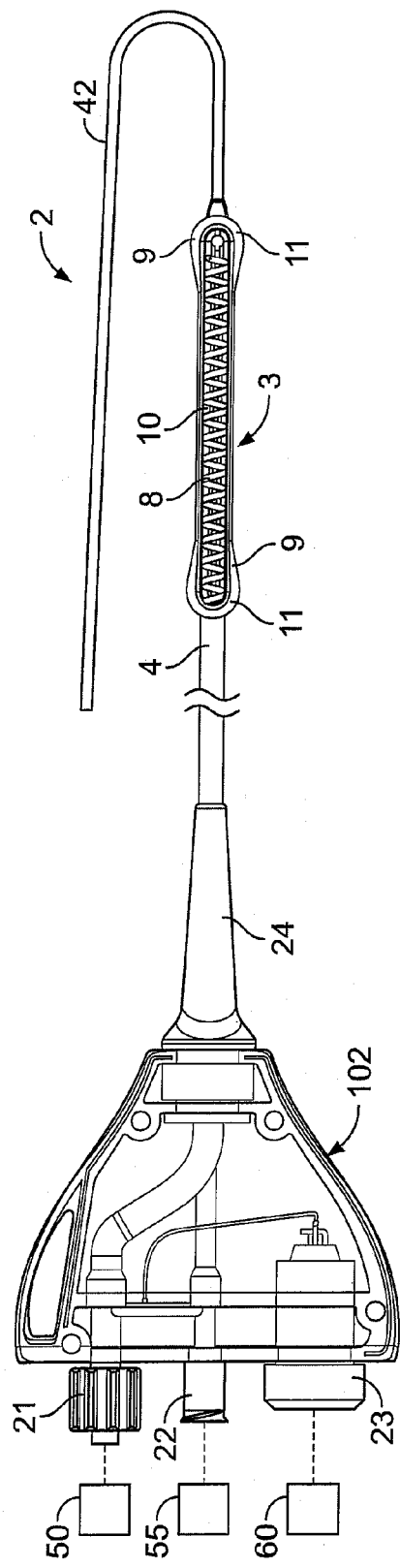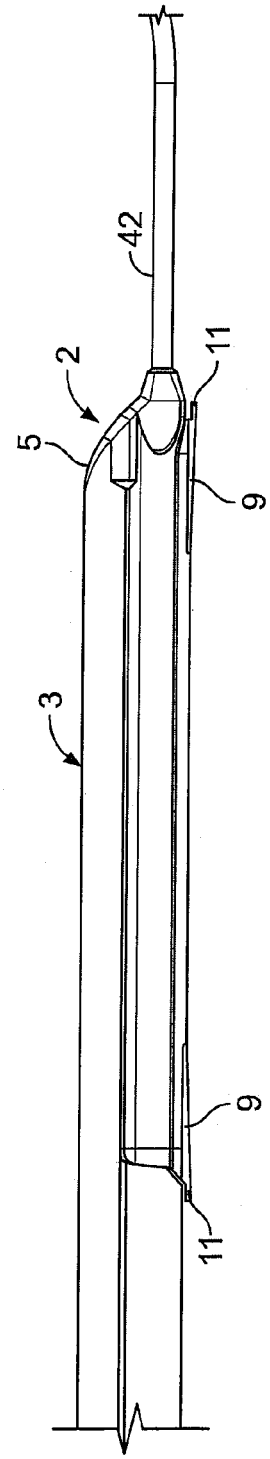
FIG. 1A
FIG. 1B

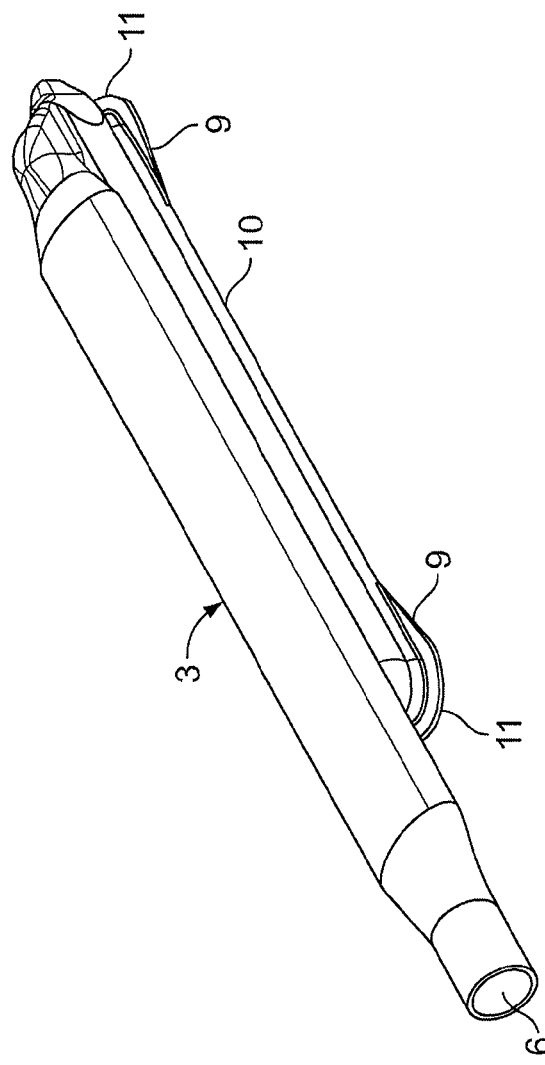
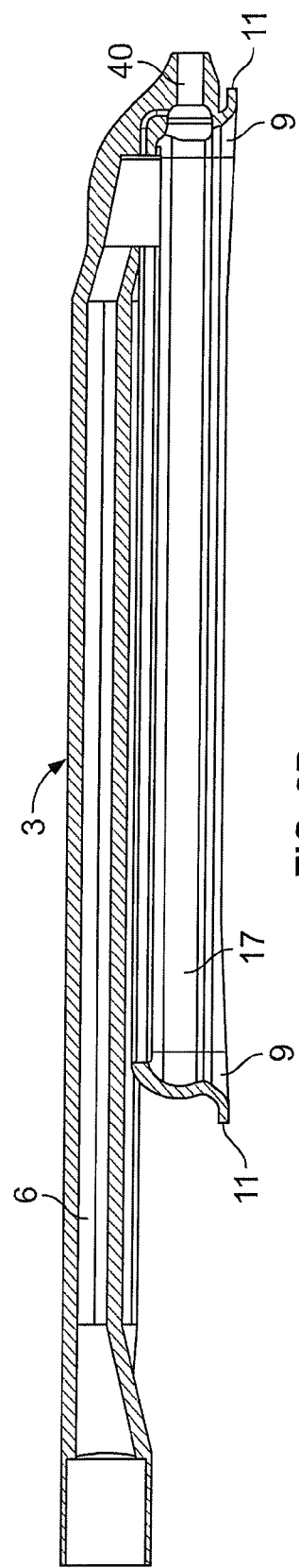
FIG. 2A
FIG. 2B

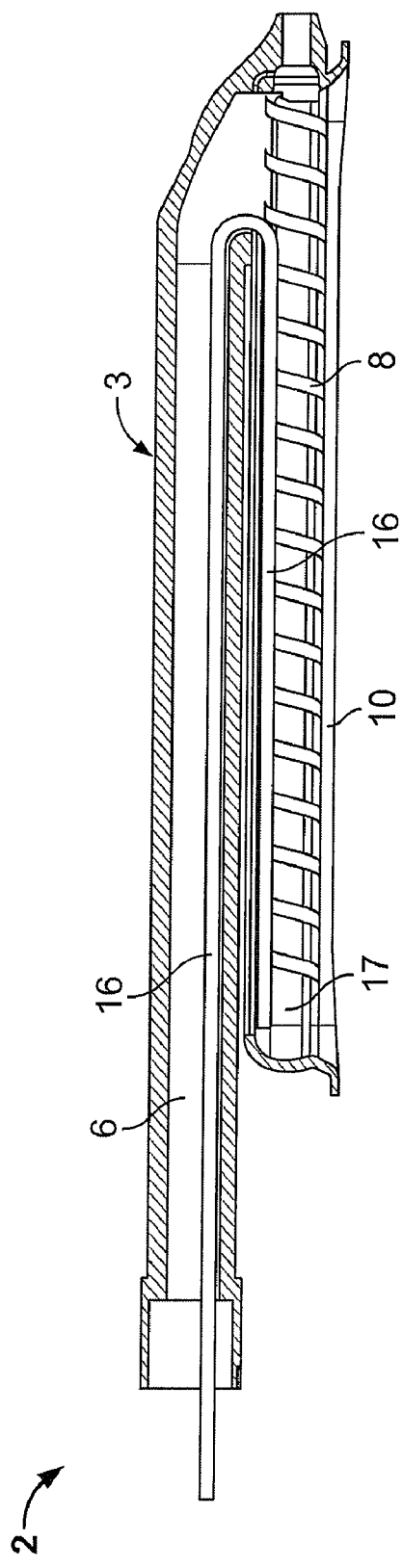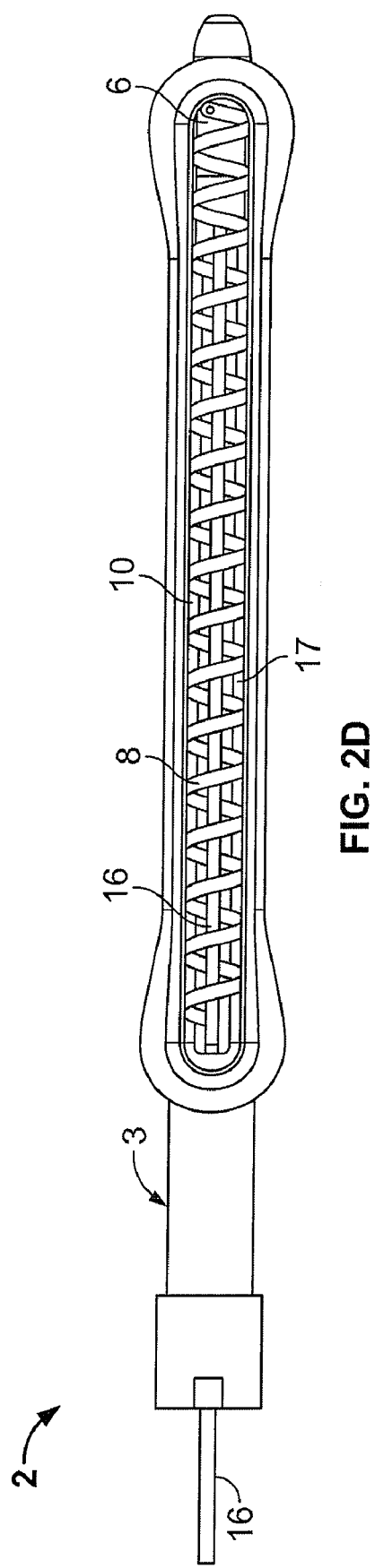
FIG. 2C
FIG. 2D

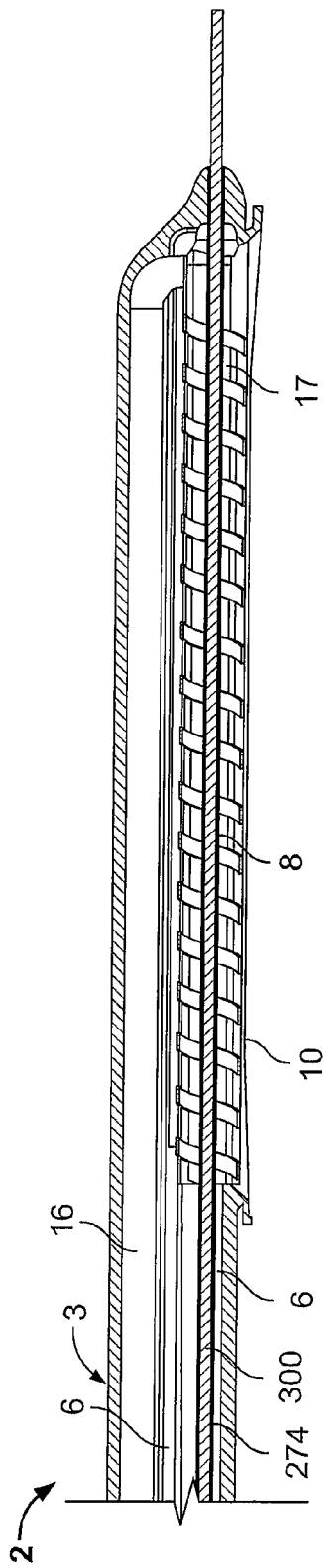
FIG. 2J
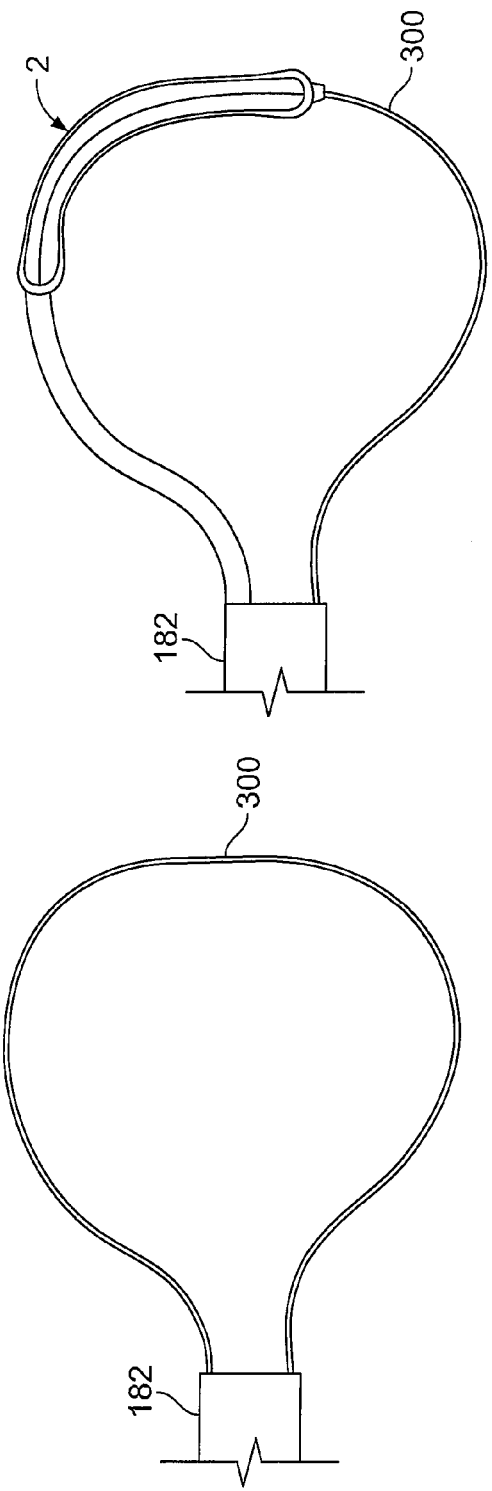
FIG. 2K
FIG. 2L

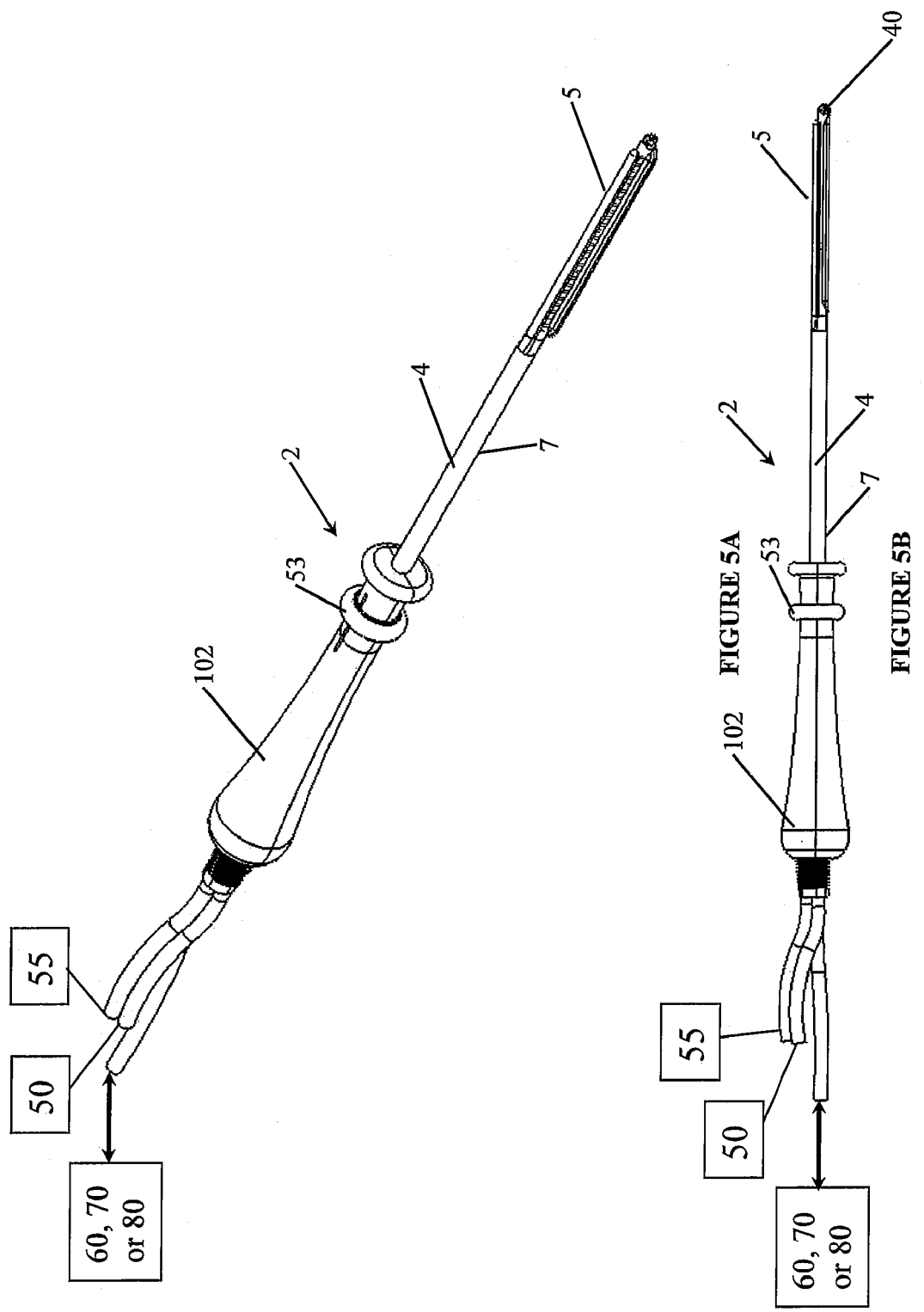

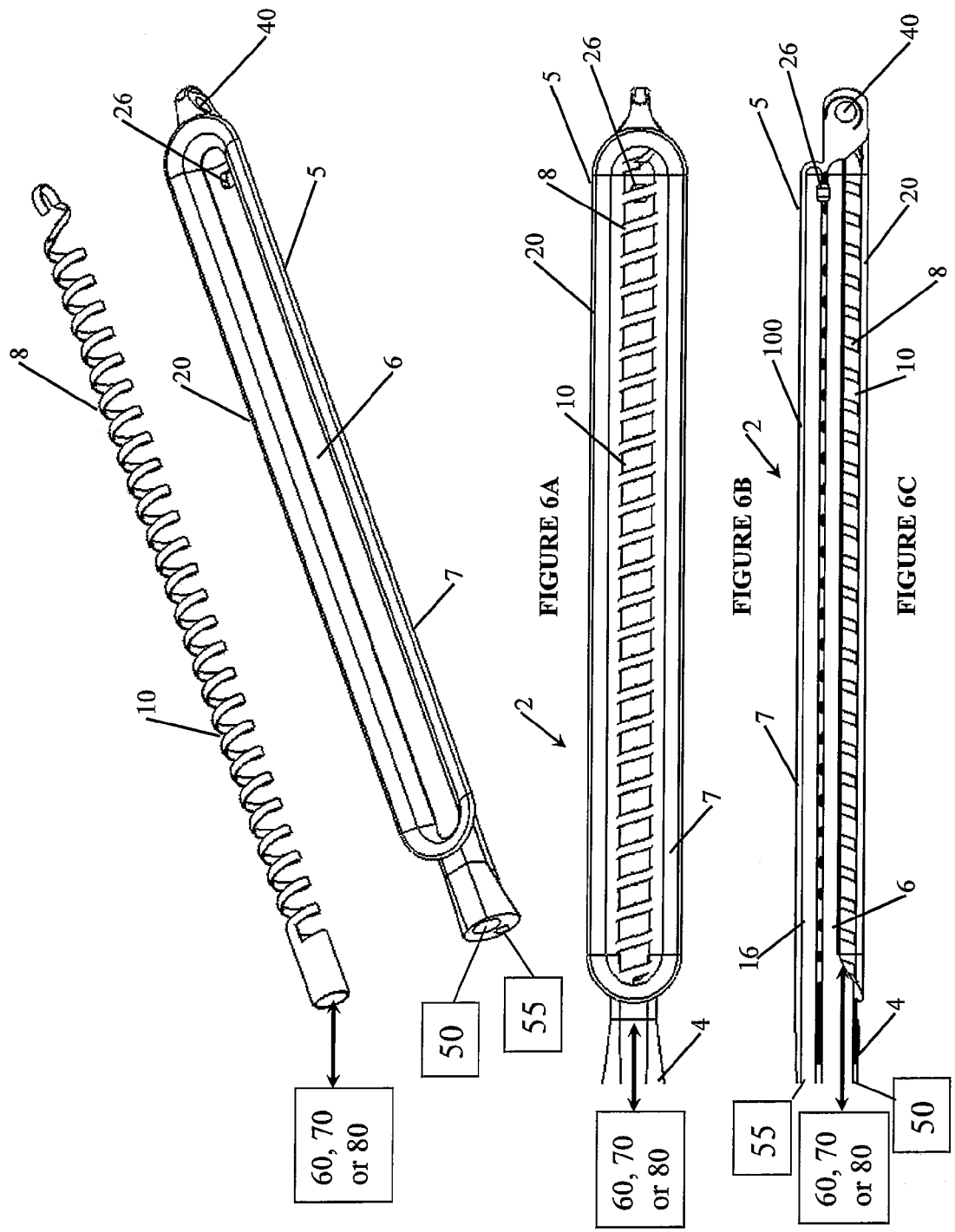

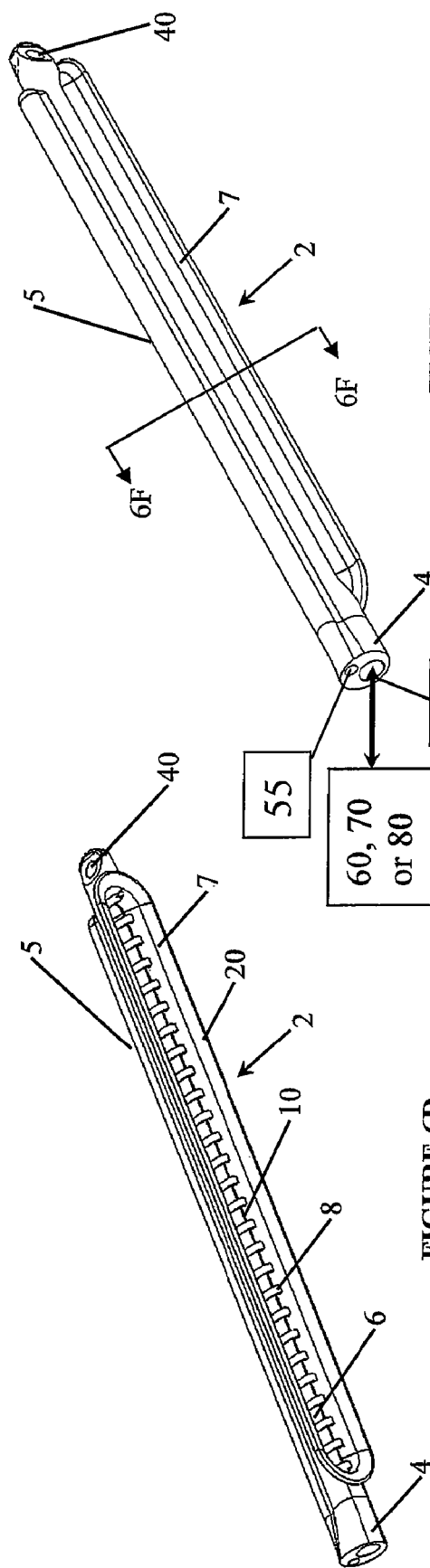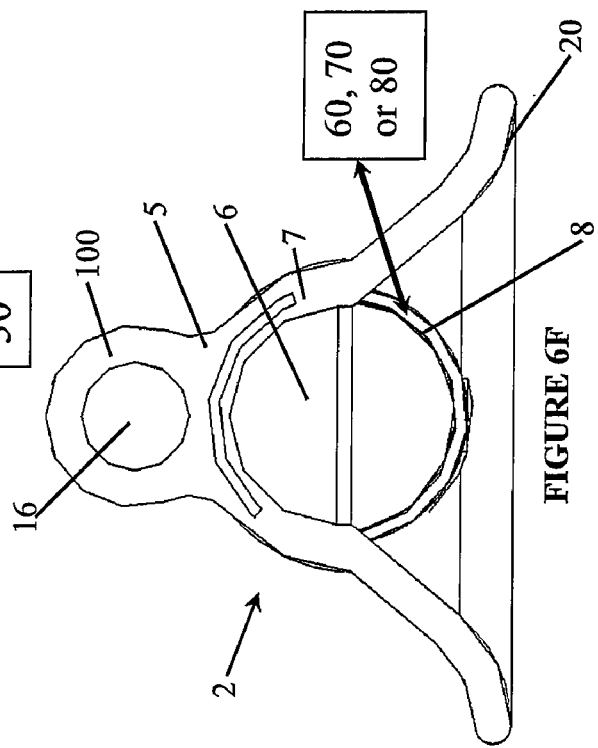

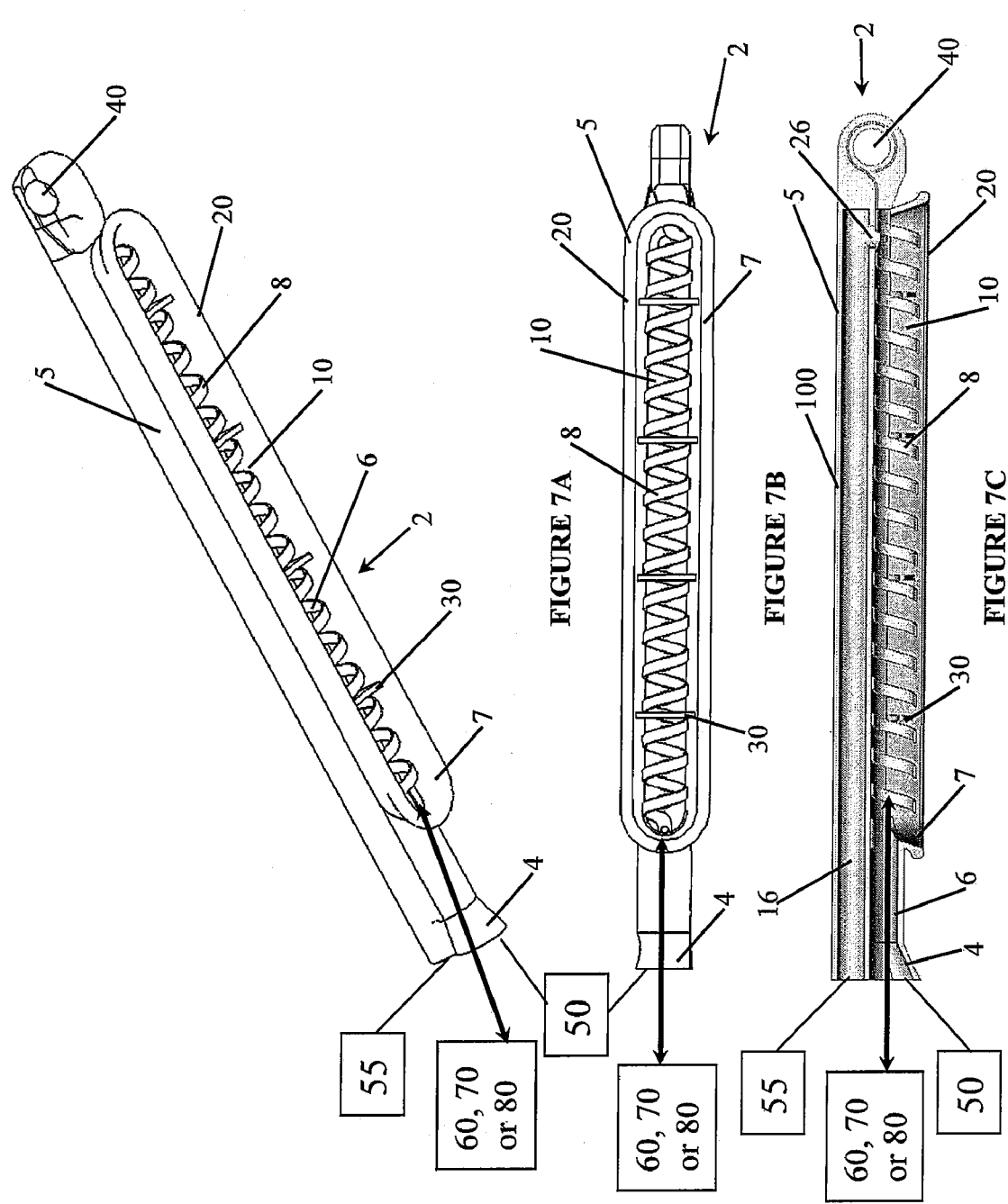

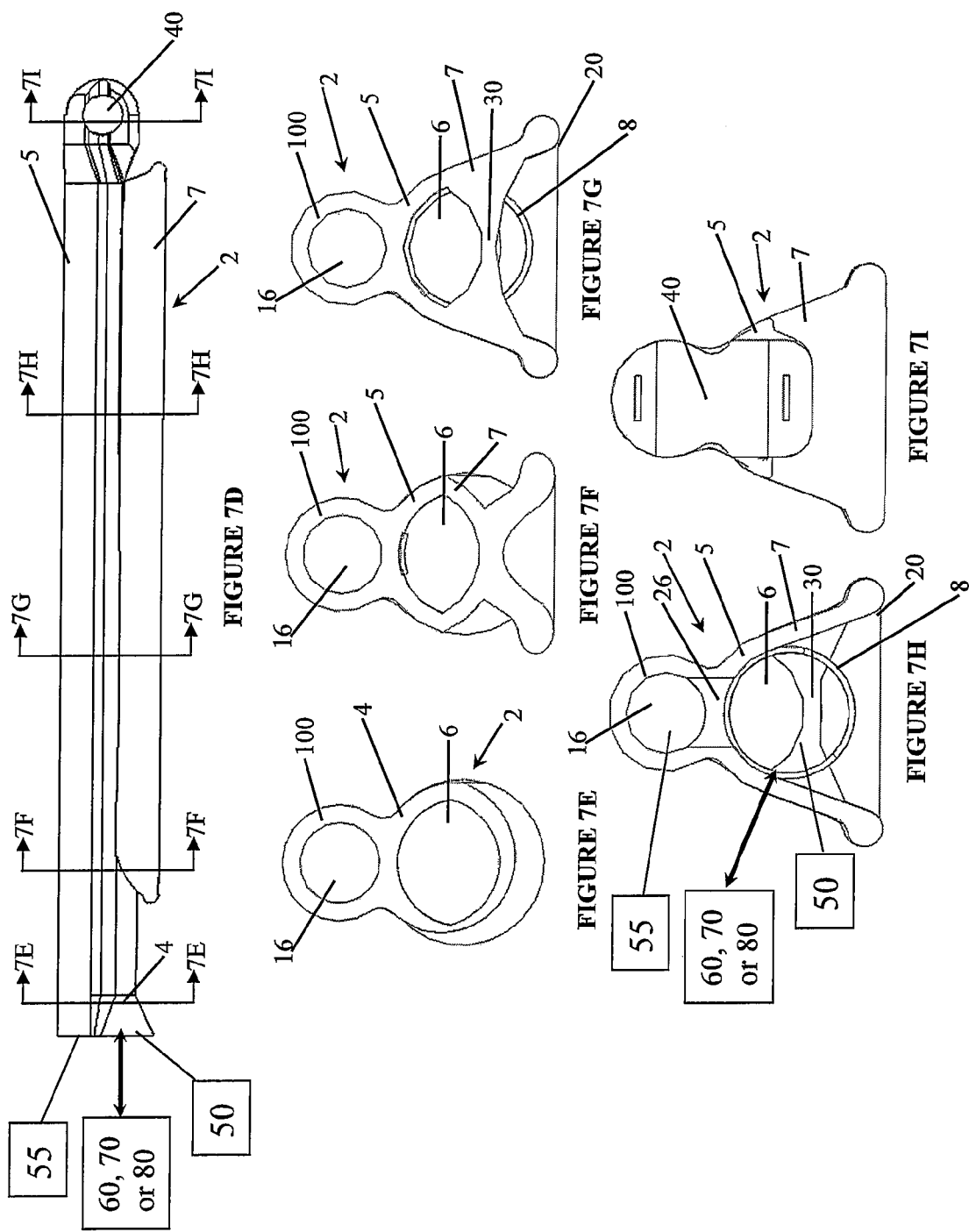

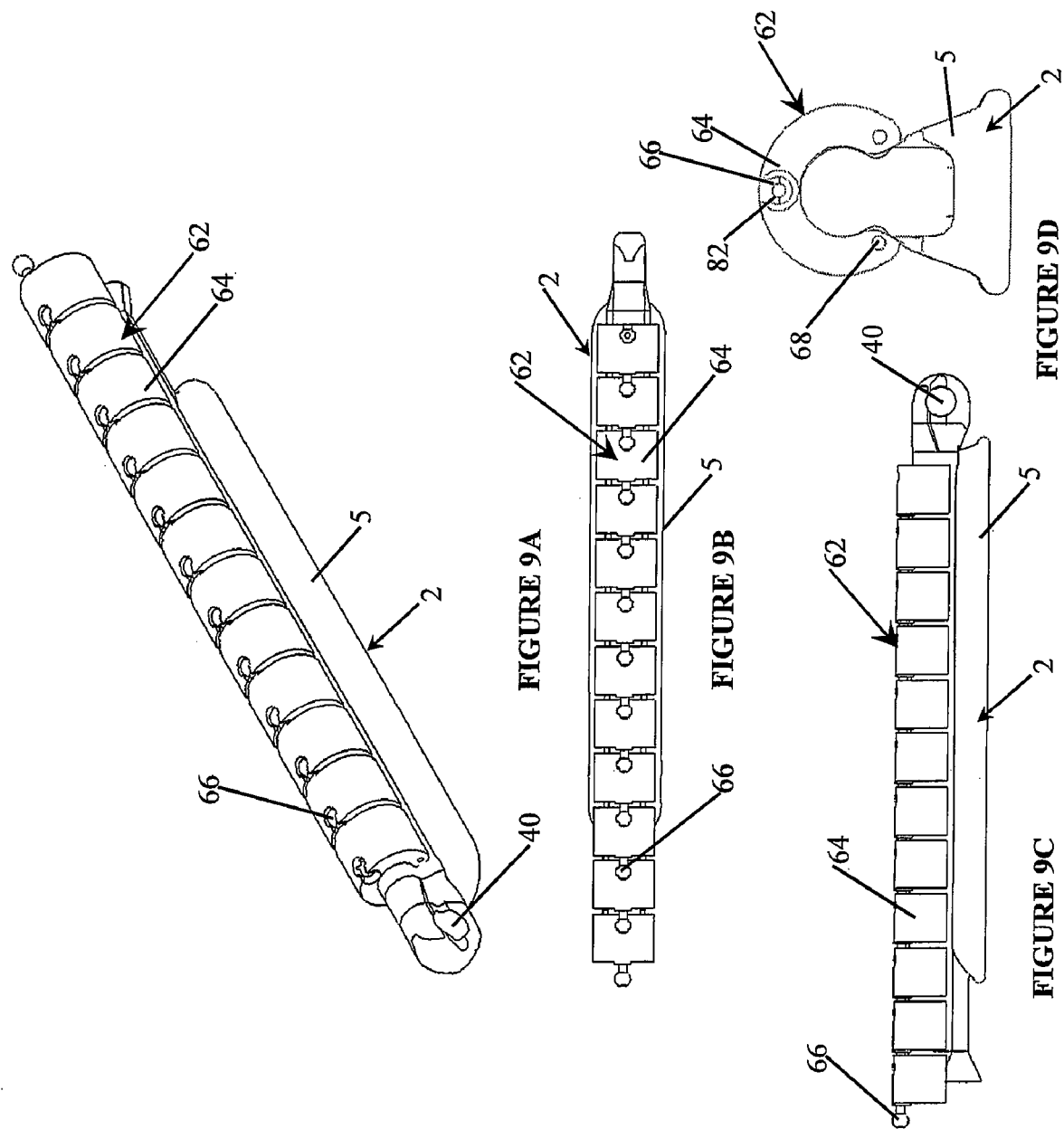

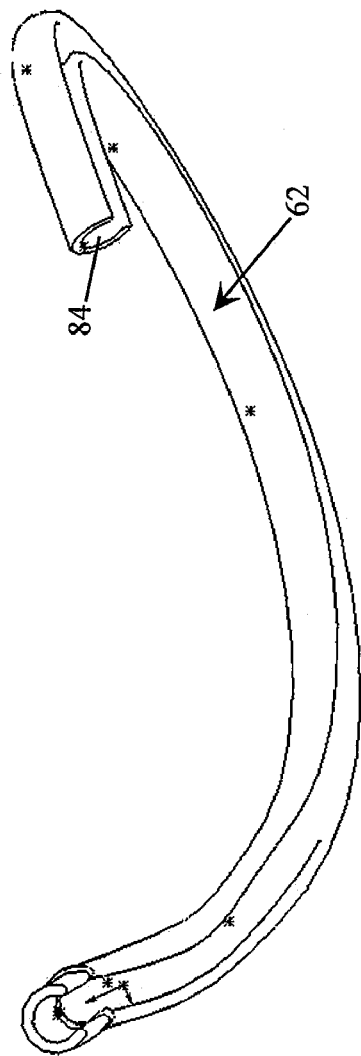
FIGURE 10
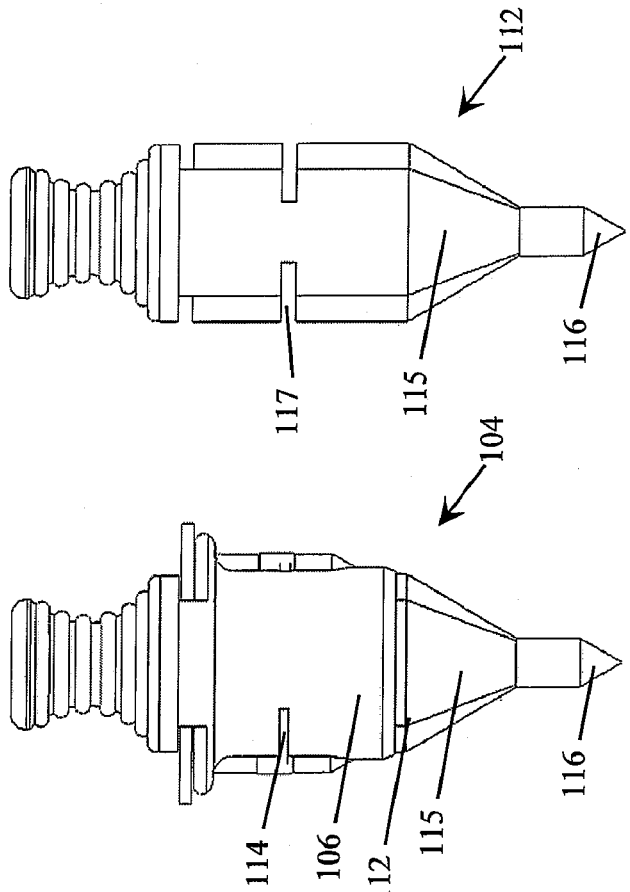
FIGURE 11A
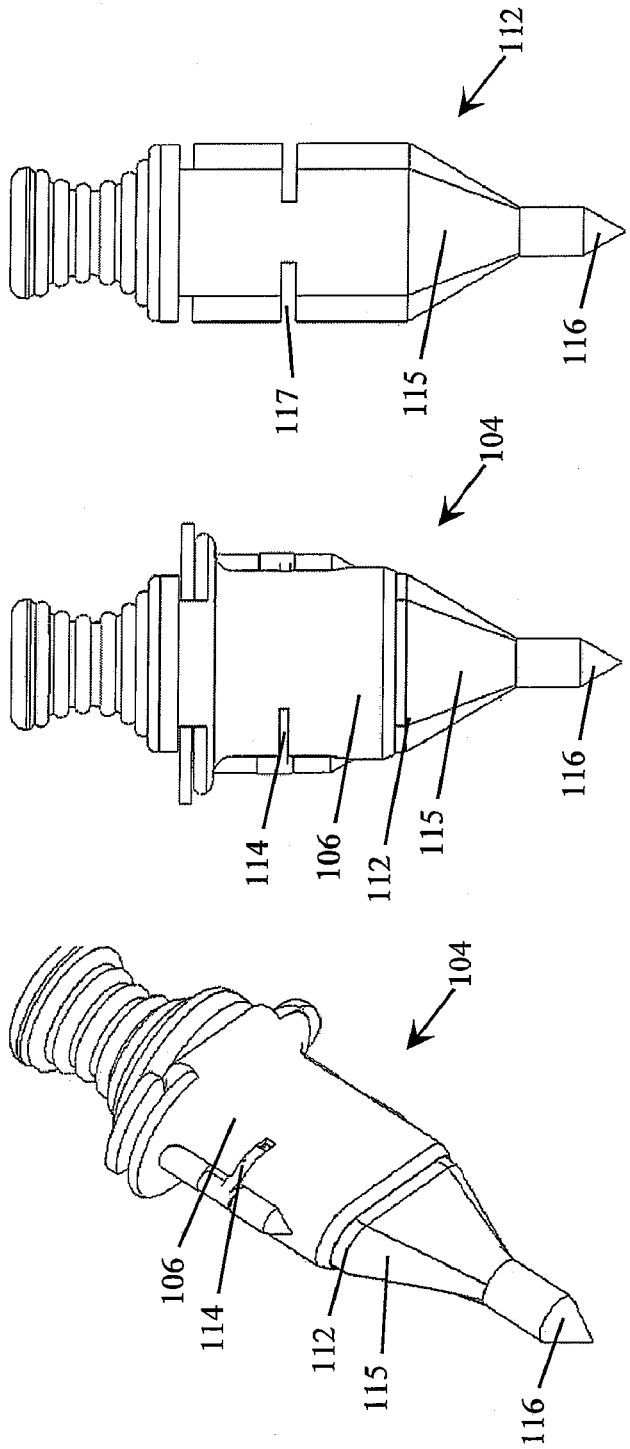
FIGURE 11B
FIGURE 11C

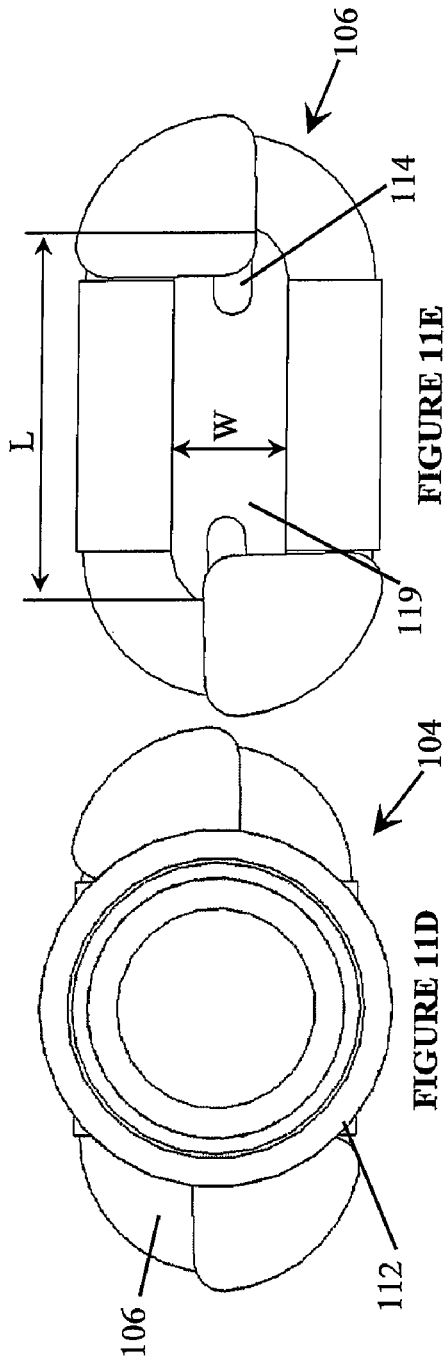
FIGURE 11D
FIGURE 11E
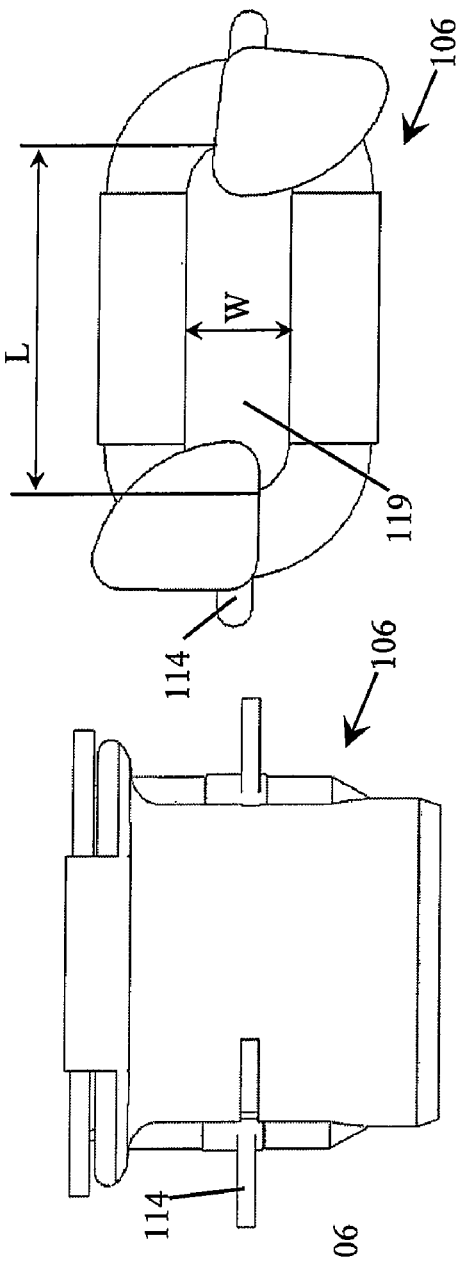
FIGURE 12C
FIGURE 12B
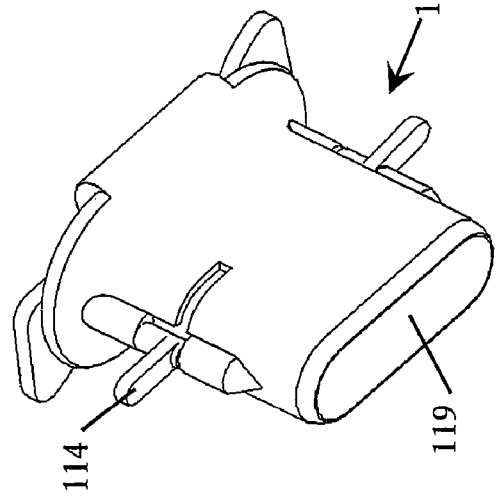
FIGURE 12A

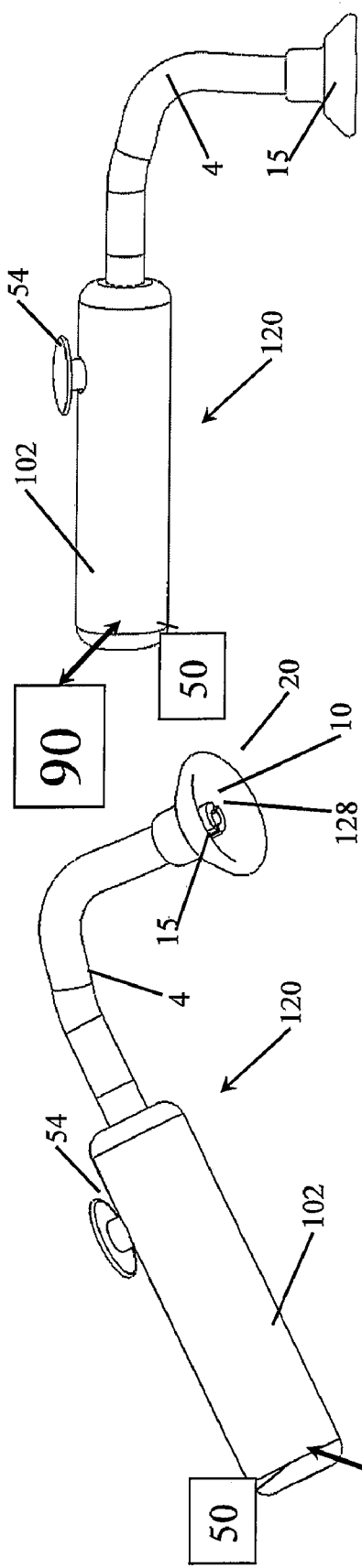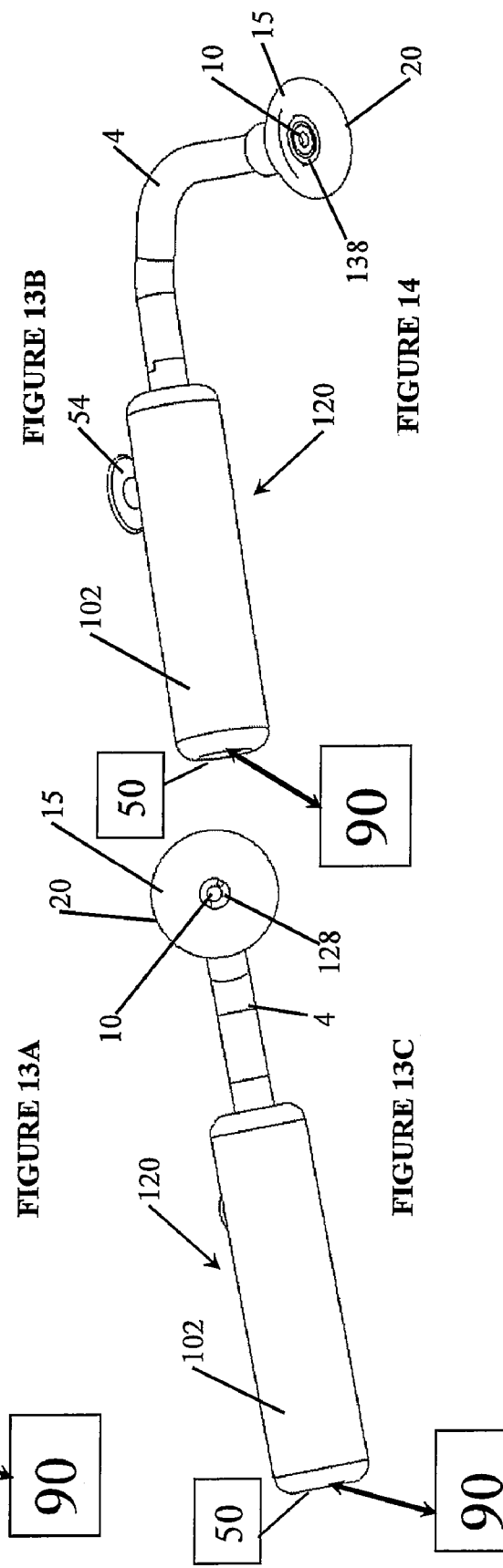

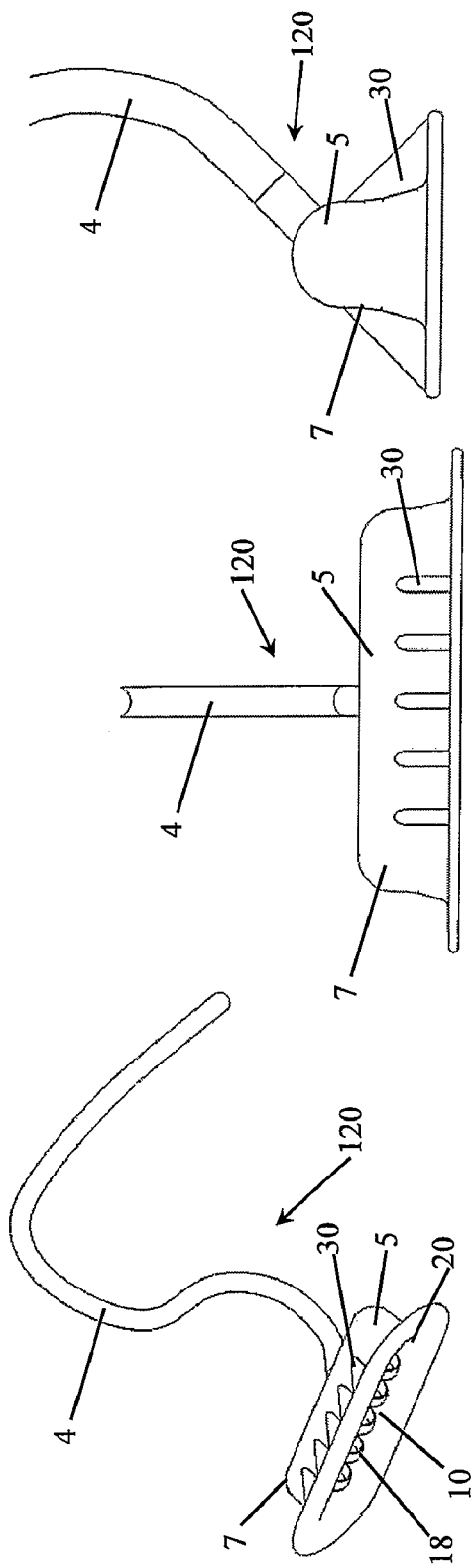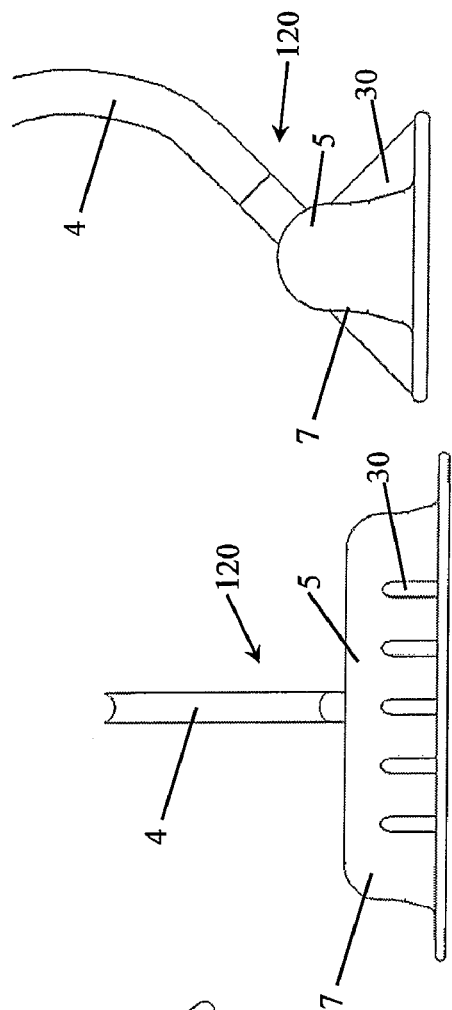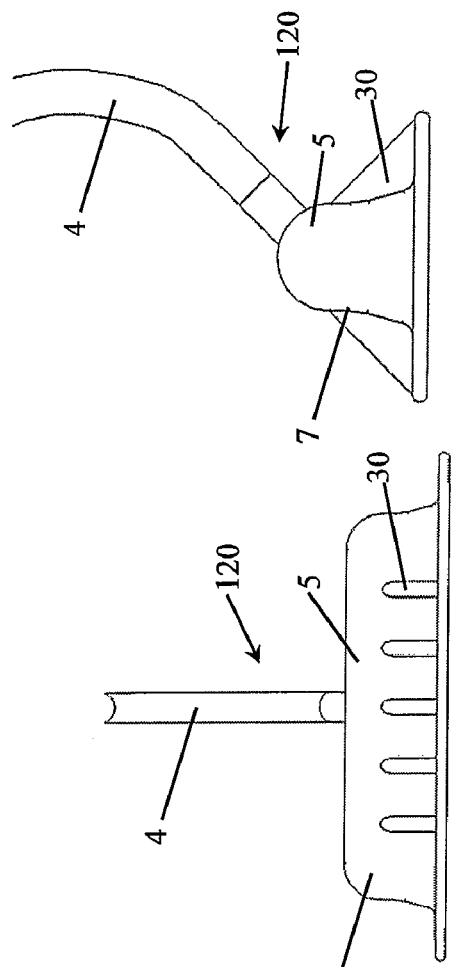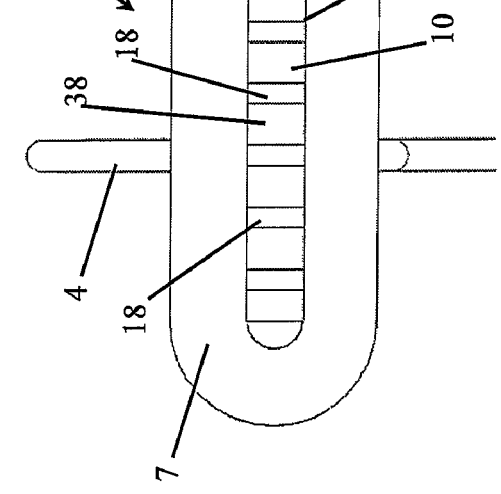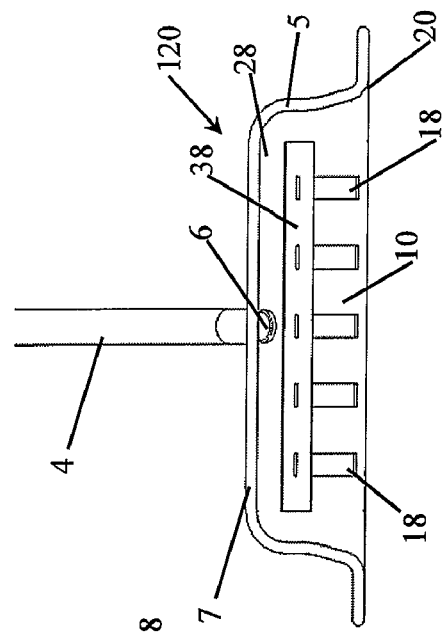

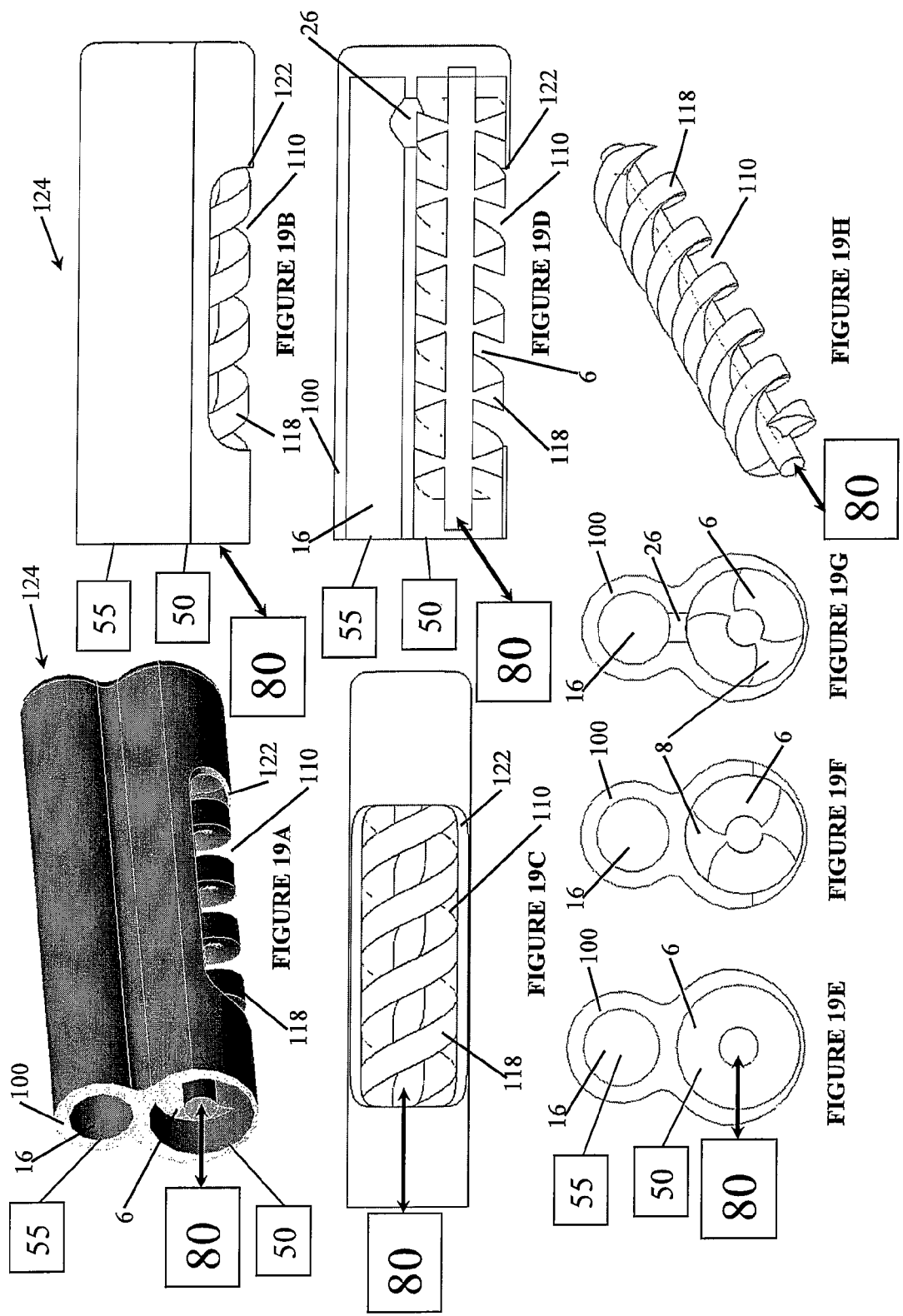

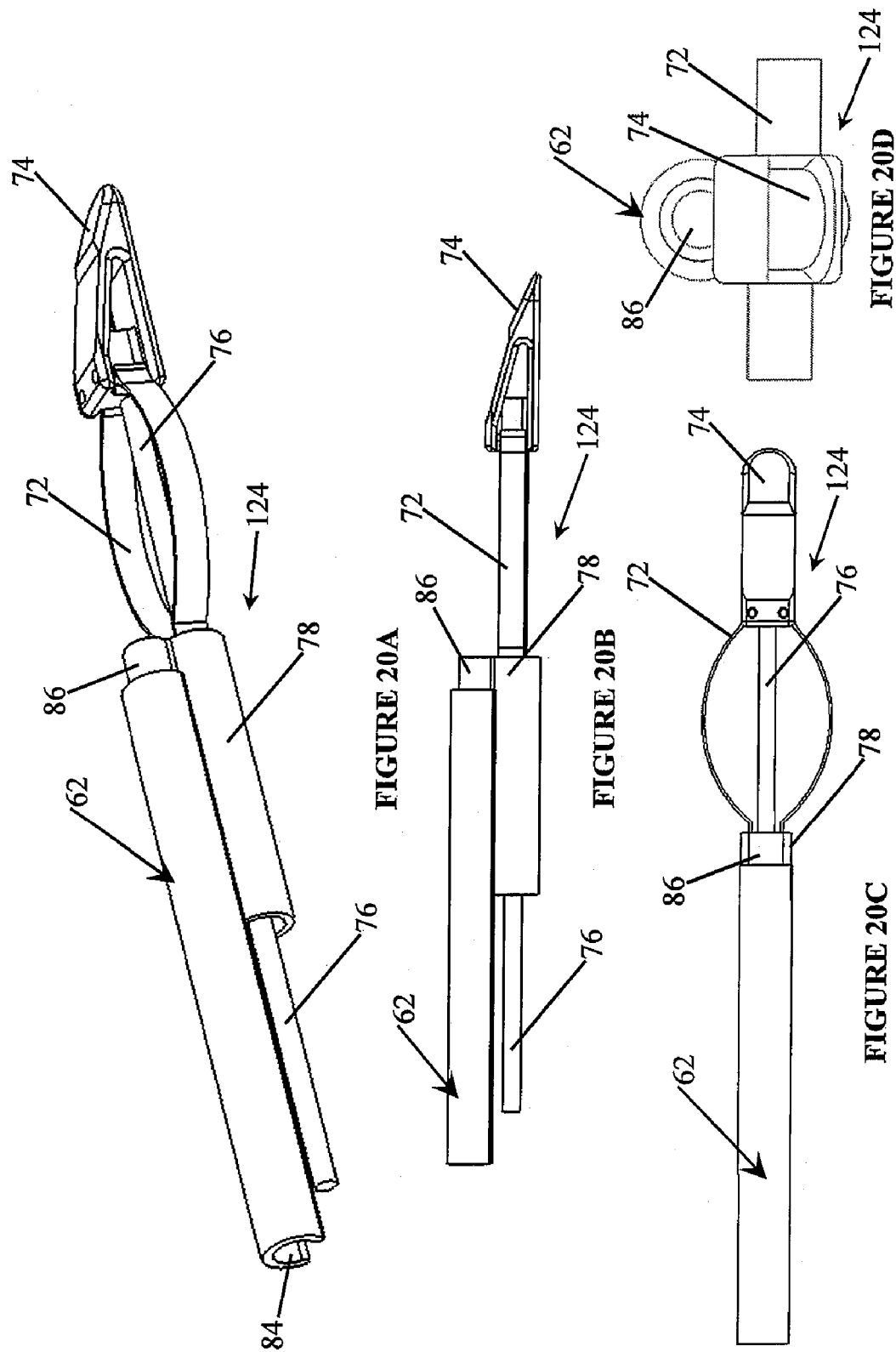

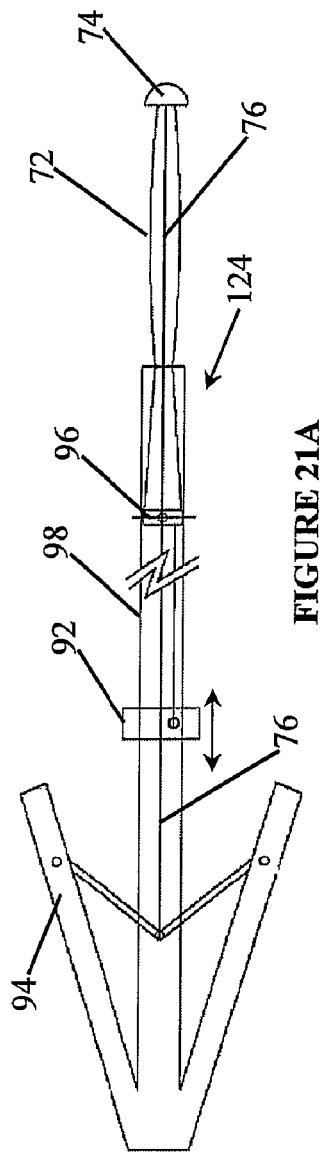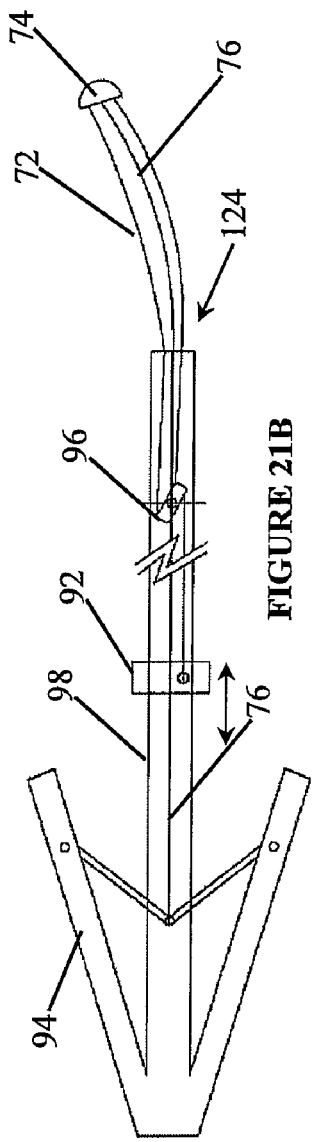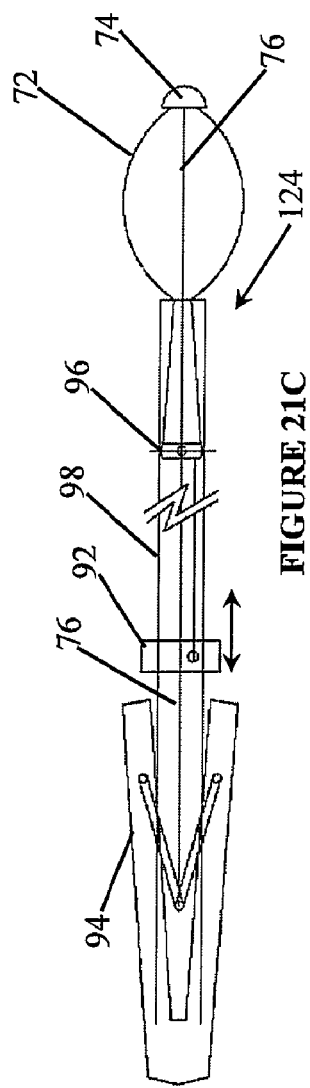

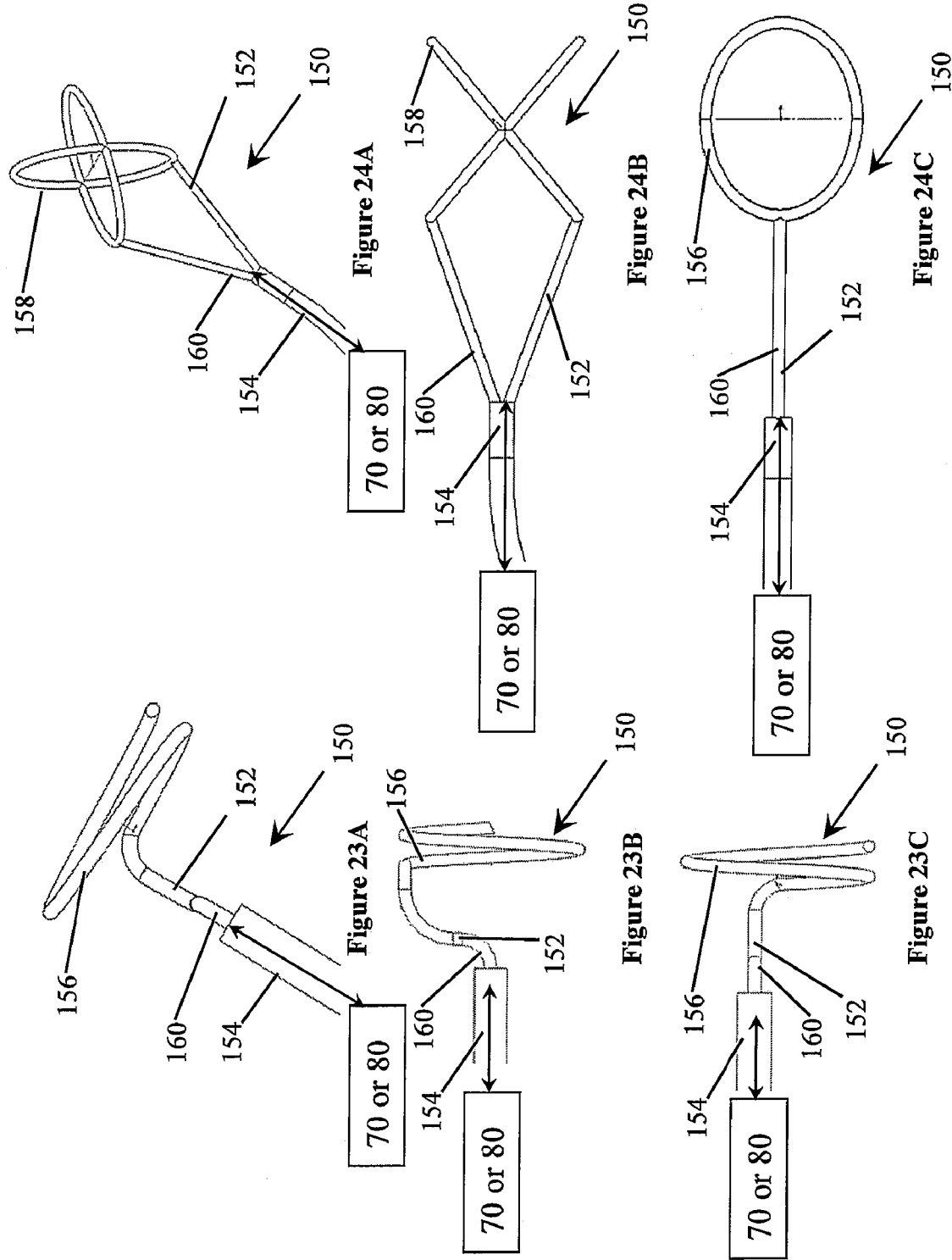

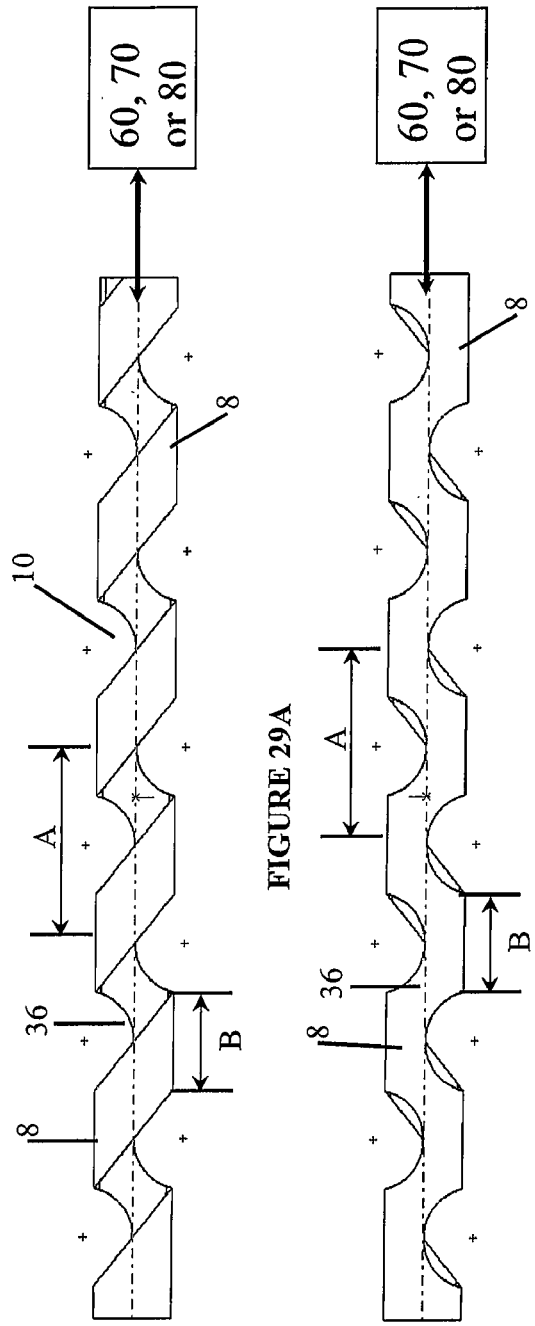
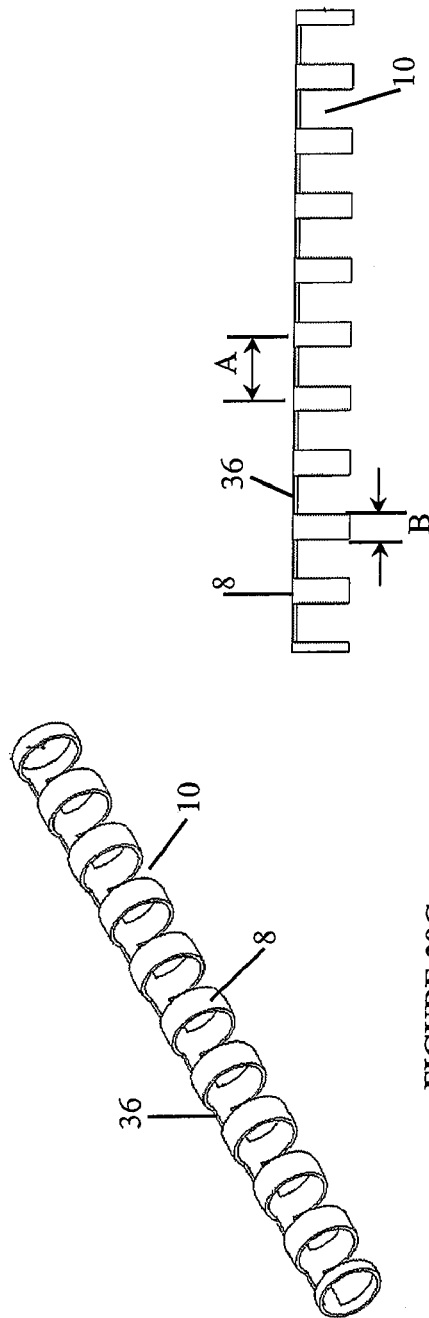
FIGURE 29A
FIGURE 29B
FIGURE 29C
FIGURE 29D

VACUUM COAGULATION PROBES

This application is a continuation-in-part of co-pending U.S. patent application Ser. No. 11/558,420, entitled, "Coagulation Probes", filed Nov. 9, 2006; this application is also a continuation-in-part of U.S. patent application Ser. No. 11/408,302 entitled "Vacuum Coagulation Probes" filed Apr. 21, 2006, which is a continuation-in-part of U.S. patent application Ser. No. 11/208,465 entitled "Vacuum Coagulation Probes" filed Aug. 18, 2005, now U.S. Pat. No. 7,572,257 which is a continuation-in-part of co-pending U.S. patent application Ser. No. 10/425,251 entitled, "Vacuum Coagulation Probes," filed Apr. 29, 2003 now U.S. Pat. No. 7,063,698, which is a continuation-in-part of U.S. patent application Ser. No. 10/172,296 entitled, "Vacuum Coagulation Probe for Atrial Fibrillation Treatment," filed Jun. 14, 2002, now U.S. Pat. No. 6,893,442. Each of the above filings is hereby incorporated by reference in their entireties

BACKGROUND

Atrial fibrillation surgery involving radiofrequency, D.C., microwave, or other thermal ablation of atrial tissue has a limitation in that tissue contact throughout the length of the electrode(s) is/are not consistent causing variability in the transmission of energy throughout the target length of ablated/coagulated tissue. This produces gaps of viable tissue that promote propagation of wavelets that sustain atrial fibrillation, or produce atrial flutter, atrial tachycardia, or other arrhythmia substrate.

Another influence in the inability of existing thermal ablation probes to create complete curvilinear, transmural lesions is the presence of convective cooling on the opposite surface of the atrium producing a heat sink that decreases the maximum temperature at this surface thereby preventing the lesions from consistently extending transmurally through the entire wall of the atrium. This is especially relevant during beating-heart procedures in which the coagulation/ablation probe is placed against the epicardial surface, and blood flowing along the endocardium removes heat thus producing a larger gradient between temperature immediately under the probe electrodes along the epicardium and that at the endocardium.

Another deficiency of current approaches is the inability to direct the coagulation of precise regions of soft tissue while avoiding underlying or nearby tissue structures. For example, atrial fibrillation ablation may involve extending a lesion to the annulus near which the circumflex, right coronary artery, and coronary sinus reside; another example involves ablating ventricular tachycardia substrates that reside near coronary arteries or coronary veins. Conventional approaches are unable to selectively ablate desired soft tissue structures and isolate preserved tissue structures from targeted regions.

Aspects of the invention address at least some of these deficiencies for atrial fibrillation and ventricular tachycardia ablation. In addition, the variations of the invention address similar deficiencies, which are apparent during other applications involving coagulation of a selected tissue region in a precise manner such as cancer ablation, soft tissue shrinking, and articular cartilage removal.

SUMMARY OF THE INVENTION

Aspects of the invention are directed to devices and methods for less invasive treatment of atrial fibrillation. The subject coagulation probes for ablation and/or coagulation integrate suction to the coagulation mechanism so as to ensure consistent and intimate tissue contact directly between the coagulation mechanism and soft tissue. The subject coagulation probes may also have features allowing for advancement or positioning of the probes using a track-member as described below.

Increased tissue contact relative to that which can be achieved with known devices is capable of reversing convective cooling effects effect noted above by evoking a compression of the tissue that shortens the wall thickness (e.g., of the atria), ensuring consistent contact throughout the length of the electrode(s), and increasing the efficiency of thermal conduction from the epicardium to the endocardium. As such a more consistent and reliable lesion is created.

As such, the integrated vacuum-assisted coagulation probes of the subject invention are capable of reliably creating transmural, curvilinear lesions capable of preventing the propagation of wavelets that initiate and sustain atrial fibrillation, atrial flutter, ventricular tachycardia, or other arrhythmia substrate.

The vacuum-assisted coagulation probes also facilitate minimally invasive surgery involving endoscopic or laparoscopic access and visualization to the target coagulation sites. Additionally, the vacuum-assisted coagulation probes of the invention are suitable for coagulating or ablating soft tissues (e.g., atrial tissue to treat atrial fibrillation, atrial flutter, or other supraventricular tachycardia; or ventricular tissue to treat ventricular tachycardia) through a median sternotomy, lateral thoracotomy, intercostals port-access, mini-sternotomies, other less invasive approaches involving subxiphoid access, subclavian access, inguinal approaches, or sub-thoracic approaches adjacent or through the diaphragm. Alternatively, the vacuum-integrated coagulation probes can be modified for catheter-based applications by elongating the shaft, altering the dimensions of the device, and incorporating other features tailored for intravascular access and manipulation.

The present invention includes systems comprising any combination of the features described herein. The probes may use any of an electrically resistive heated, RF, vibrational/ultrasonic transmission element or elements as described herein as a tissue heating element. The various structures described for applying energy to heat tissue may be regarded as the various means for tissue coagulation disclosed herein. Methodology described in association with the devices disclosed also forms part of the invention.

Such methodology may include that associated with coagulating other soft tissues for a variety of applications including cancer therapy (e.g., liver, prostate, colon, esophageal, gastrointestinal, gynecological, etc.); Gastro-esophageal Reflux Disease treatment; shrinking of collagen-based tissue structures such as skin, tendons, muscles, ligaments, vascular tissue during arthroscopic, laparoscopic, or other minimally invasive procedures; and/or coagulation of an upper layer of tissue without damaging underlying tissue structures, for example during articular cartilage removal.

Similar coagulation probes are disclosed in: U.S. patent application Ser. No. 11/408,302 entitled "Vacuum Coagulation Probes"; U.S. patent application Ser. No. 11/208,465 entitled "Vacuum Coagulation & Dissection Probes"; U.S. patent application Ser. No. 10/425,251 entitled "Vacuum Coagulation Probes"; U.S. Provisional application No. 60/726,342 entitled Diaphragm Entry for Posterior Access Surgical Procedures; and U.S. Pat. No. 6,893,442 the entirety of each of which is hereby incorporated by reference.

BRIEF DESCRIPTION OF DRAWINGS

Each of the figures diagrammatically illustrates aspects of the invention. Of these:

FIG. 1A shows an example of a coagulation probe;

FIG. 1B shows a side view of the coagulation probe of FIG. 1A;

FIGS. 2A to 2B show elongate housing members having a main lumen extending across a top of the housing;

FIGS. 2C to 2D show a perfusion or fluid supply lumen within the main lumen where both lumens extend across a top of the housing;

FIG. 2J shows a variation of a coagulation probe where a track extends through a main lumen, a main cavity and through a distal end of a housing;

FIGS. 2K to 2L show a method of using a probe and track to treat tissue;

FIGS. 5A and 5B show an isometric view, and a side view of an assembled integrated vacuum-integrated coagulation probe variation;

FIGS. 6A to 6F show an exploded view, a bottom view, a side sectional view, two isometric views, and a cross-sectional view of the distal end of the vacuum-integrated coagulation probe variation in FIGS. 5A and 5B;

FIGS. 7A to 7I show an isometric view, a bottom view, a side sectional view, a side view and five cross-sectional views of the distal end of another vacuum-integrated coagulation probe variation;

FIGS. 9A to 9D show an isometric view, a top view, a side view, and an end view of a vacuum-integrated coagulation probe variation supported by the rail mechanism in FIGS. 8A to 8C;

FIG. 10 shows a perspective view of an alternative external guide variation;

FIGS. 11A and 11B show an isometric view and a side view of a locking, elliptical trocar system;

FIG. 11C shows a side view of the puncturing dilator for the trocar in FIGS. 11A and 11B;

FIG. 11D shows a top view of the trocar system in FIGS. 11A and 11B;

FIG. 11E shows a top view of the trocar sheath in FIGS. 11A and 11B;

FIGS. 12A to 12C show an isometric view, a side view, and a top view of the trocar sheath in FIGS. 11A to 11E in a deployed and locked orientation;

FIGS. 13A to 13C show an isometric view, a side view, and a bottom view of a vacuum-integrated theranostic probe variation;

FIG. 14 shows an isometric view of an alternative vacuum-integrated theranostic probe;

FIGS. 17A to 17E show an isometric view, a front view, a side view, a bottom view, and a sectional view of another theranostic probe variation;

FIGS. 19A to 19G show an isometric view, a side view, a bottom view, a side-sectional view, and three cross-sectional views of the distal end of another vacuum-integrated dissecting tool/coagulation probe variation;

FIG. 19H shows an isometric view of the distal end of the rotating dissecting/coagulating component of the variation in FIGS. 19A to 19G;

FIGS. 20A to 20D show an isometric view, a side view, a top view, and an end view of a dissecting/tunneling instrument;

FIGS. 21A to 21C show sectional views of the dissecting/tunneling instrument in FIGS. 20A to 20D without the handle actuated, with the dissecting loops expanded, and with the integrated steering mechanism actuated respectively;

FIGS. 23A to 23C show an isometric view, a side view, and a top view of a mechanically vibrating ultrasonic ablation catheter variation;

FIGS. 24A to 24C show an isometric view, a side view, and a top view of another mechanically vibrating ultrasonic ablation catheter variation;

FIGS. 29A and 29B show a bottom view and a top view of another electrode variation for an integrated vacuum coagulation probe;

FIGS. 29C and 29D show an isometric view and a side view of another electrode variation.

DETAILED DESCRIPTION

Figure 1C:
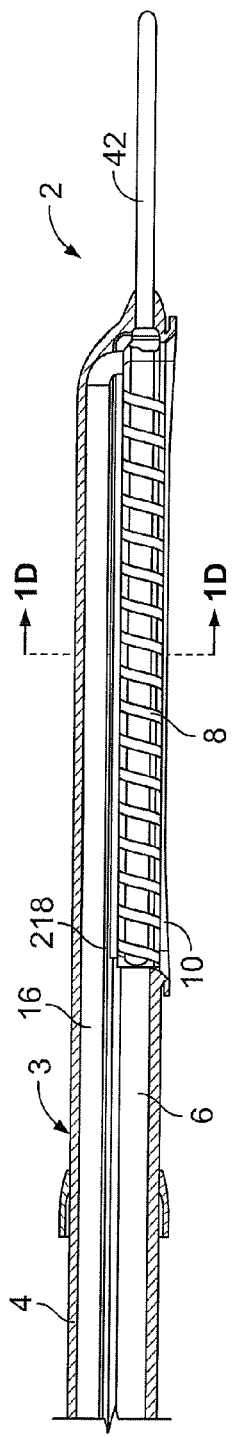
FIG. 1C shows a cross sectional view of the coagulation probe of FIG. 1A.

In light of this framework, a number of exemplary variations of the invention are disclosed—mainly in the context of soft tissue coagulation accomplished through less invasive approaches (e.g., thoracoscopic, arthroscopic, laparoscopic, percutaneous, or other minimally invasive procedures). The integrated vacuum coagulation probe variations disclosed herein produce intimate contact specifically between a soft tissue surface and the electrode(s) or vibration elements used to transmit energy (e.g., radiofrequency or ultrasonic) capable of heating the soft tissue until irreversible injury is achieved making the soft tissue non-viable and unable to propagate electrical impulses, mutate, or reproduce.

The integrated vacuum coagulation probe variations may also enable supporting and/or repositioning the soft tissue during coagulation to prevent or minimize shrinking or other change in the shape of the soft tissue associated with heat causing the collagen in the soft tissue to denature. Nevertheless, it should be appreciated that the integrated vacuum coagulation probe devices can be applied to other indications involving devices that are used to coagulate soft tissue where access to the tissue is limited by a small opening into the cavity, confined space at the soft tissue interface, difficult to reach locations, or other anatomic limitation.

An additional potential benefit the subject devices involves the ease of deployment and rapid healing post-procedure. The small incision used to access the soft tissue during such procedures accelerates the healing process and reduces the visible scar. The integrated vacuum coagulation probe devices can be capable of being deployed through a thoracostomy, thoracotomy, median sternotomy, mini-sternotomy, mini-thoracotomy, subxyphoid access, subthoracic access, arthroscopic, or laparoscopic approach, thereby potentially eliminating the need for long incisions to access the soft tissue and corresponding anatomic structures.

A need exists for integrated vacuum coagulation probe devices and methods that create lesions of structurally strong but electrically non-viable tissue in the atria to treat atrial fibrillation, atrial flutter, or other supraventricular tachycardia, or in the ventricles to treat ventricular tachycardia. In addition, such devices and methods could simplify and improve other soft tissue coagulation procedures by ensuring intimate tissue contact while precisely and effectively heating a region of soft tissue. For example, tendon shrinking during arthroscopic procedures and articular cartilage fragment removal from bony tissue are facilitated and controlled with the variations of the invention. In addition, ablation of cancer tissue in the lung, liver, kidney, or other anatomic structure is improved by the vacuum-integrated variations of the invention. The variations of the invention also enable pharmacologically modifying tissue structures with localized administration of pharmacological agents to cross-link, render nonfunctional, destroy, remove, or otherwise adapt tissue to specific needs.

The technology may also allow for certain procedures to be performed less invasively through limited incisions that previously required large, open incisions with inherent morbidity and risks to other anatomic structures. As such, patients how undergo such reparative or therapeutic surgical procedures may endure less pain, and enjoy expedited hospital stays and shorter rehabilitative and recovery times.

The present invention relates to methods and devices that enable reliable and controlled coagulation of soft tissue during less invasive procedures. To accomplish this, the coagulation probe incorporates vacuum conduits integrated with the electrode(s) and/or vibrational elements to urge the soft tissue into intimate contact with the strategically-located edges of the electrode(s) and/or vibrational elements and ensure efficient transmission of energy (thermal, radiofrequency or mechanically induced ultrasonic energy respectively) capable of consistently and completely rendering a desired region of soft tissue electrically nonviable. The suction force pulls the soft tissue into direct engagement with the electrode(s) or vibrational elements and induces a one-sided compression of the soft tissue structure by pulling sections of the soft tissue into the openings defined through the electrode(s) or vibrational elements causing soft tissue residing between the openings thus over the electrode or vibrational element component(s) to compress into a smaller wall thickness.

Electrode(s) are used when applying energy to tissue (e.g., when radiofrequency energy is transmitted into tissue, when a resistive electrode conducts heat energy to tissue, etc.) to cause the targeted soft tissue to heat thereby causing cellular responses that result in inhibiting conduction of electrical stimuli through the tissue cells but maintaining structural strength of the soft tissue. Vibrational elements emit an ultrasonic wave as a drive shaft is used to move the vibrational elements along the axis of the vibrational elements using a linear motor or radially around the axis using a rotary motor. This high frequency, small displacement movement causes the vibrational elements to move in such a fashion that an ultrasonic signal is emitted into soft tissue that is directly contacting the vibrational elements.

The integrated vacuum coagulation probe variations of the invention also enable passive convective cooling of the tissue surface by using the vacuum source to transport fluid along the tissue surface from a fluid source without the need for a separate injector or pump. Convective cooling of the surface helps avoid acute desiccation that leads to charring, thus allowing delivery of increased energy into the tissue and creating larger and deeper lesions by reaching maximum temperature below the tissue surface. The potential benefits of convective surface cooling in achieving better lesions are well known by those with skill in the art.

Supplemental or alternative to use of vacuum for passive cooling, the vacuum source may cycle the vacuum pressure applied between the electrode(s)/vibrational elements and directly contacted soft tissue at a high rate to vary the degree of tissue compression. Such variation can induce direct tissue vibration to develop a mechanically-induced ultrasonic wavefront capable of causing cavitation and heating of the soft tissue for ablating the targeted tissue surface.

The integrated vacuum coagulation probe, and corresponding components, can be fabricated from at least one rod, wire, band, bar, tube, sheet, ribbon, other raw material having the desired pattern, cross-sectional profile, and dimensions, or a combination of cross-sections. The rod, wire, band, bar, sheet, tube, ribbon, or other raw material can be fabricated by extruding, injection molding, press-forging, rotary forging, bar rolling, sheet rolling, cold drawing, cold rolling, using multiple cold-working and annealing steps, casting, or otherwise forming into the desired shape. The components of the integrated vacuum coagulation probe may be cut from raw material by conventional abrasive sawing, water jet cutting, laser cutting, ultrasonic cutting, EDM machining, photochemical etching, or other techniques to cut the lumens, pores, ports and/or other features of the vacuum coagulation probe from the raw material. Components of the integrated vacuum coagulation probe can be bonded by laser welding, adhesives, ultrasonic welding, radiofrequency welding, soldering, spot welding, or other attachment means.

For several of the integrated vacuum coagulation probe variations below, various components can be fabricated from at least one wire, tube, ribbon, sheet, rod, band or bar of raw material cut to the desired configuration and thermally formed into the desired 3-dimensional configuration. When thermally forming (e.g., annealing) components, they can be stressed into the desired resting configuration using mandrels and/or forming fixtures having the desired resting shape of the puncturing component, and heated to between 300 and 600 degrees Celsius for a period of time, typically between 15 seconds and 10 minutes. Alternatively, the components may be heating immediately prior to stressing. Once the volume of material reaches the desired temperature, the component is quenched by inserting into chilled or room temperature water or other fluid, or allowed to return to ambient temperature. As such, the components can be fabricated into their resting configuration. When extremely small radii of curvature are desired, multiple thermal forming steps can be utilized to sequentially bend the component into smaller radii of curvature.

When fabricating the integrated vacuum coagulation probe components from tubing, the raw material can have an oval, circular, rectangular, square, trapezoidal, or other cross-sectional geometry capable of being cut into the desired pattern. After cutting the desired pattern of lumens, ports, and pores, the components can be formed into the desired shape, stressed, heated, for example, between 300° C. and 600° C., and allowed to cool in the preformed geometry to set the shape of the components, as discussed above.

Once the components are fabricated and formed into the desired 3-dimensional geometry, they can be tumbled, sand blasted, bead blasted, chemically etched, ground, mechanically polished, electropolished, or otherwise treated to remove any edges and/or produce a smooth surface.

Holes, slots, notches, other cut-away areas, or regions of ground material can be incorporated in the components to tailor the stiffness profile or incorporate features that enhance performance of the devices. Cutting and treating processes described above can be used to fabricate the slots, holes, notches, cut-away regions, and/or ground regions in the desired pattern to taper the stiffness along, focus the stiffness along the length of, reinforce specific regions of, or otherwise customize the stiffness profile of the vacuum probe components.

Naturally, any number of other manufacturing techniques may be employed. Furthermore, it is to be understood that the exemplary device configurations may be varied.

Vacuum-Integrated Coagulation Probe Variations

FIG. 1A illustrates a variation of a coagulation device consisting of a probe 2 and a handle 102 (showing a cross-sectional view of the handle body). In this variation, the probe 2 includes a shaft 4 having a housing 9 at a distal section 5 of the shaft 4. Variations of the coagulation device may employ any variety of shapes and sizes for the handles. In the example shown, the handle 102 includes a plurality of, connectors 21, 22, 23 for connecting the probe to a power supply 60, a fluid source 55 and a vacuum source 50 respectively.

In a variation of the device, the fluid source 55 connection 22 incorporates a flow limiter to keep the perfusion rate through the perfusion lumen constant at different vacuum pressures and positions of the fluid source. In one example, the flow limiter comprises a constant diameter tubing that restricts flow therethrough along a large range of vacuum pressures or fluid source injection pressures. For example, a polyimide tubing having a 0.006" ID, 0.350" length, and a 0.003" wall thickness is capable of limiting the perfusion rate to 4 ml/min through the perfusion lumen despite vacuum pressures ranging from −200 mmHg to −600 mmHg.

Most variations of the devices described herein include a connector for a power supply and vacuum source. However, such connectors may be combined in a single connection and locked to the handle. Combining the vacuum and fluid source connectors into a single component interconnected by a bridge designed to provide stability ensures integrity of the connectors while rotating the mating connector into engagement or removing the mating connector. Alternatively, the device may include more connectors than that shown in FIG. 1A.

As illustrated, the shaft 4 may optionally include additional components (such as a strain relief 24) to increase the robustness of the device. The shaft 4 includes a housing 3 located at a distal end 5 of the shaft 4. As discussed below, the housing 3 includes an element 8 and an opening that expose the element 8 to tissue. The element 8 may be an electrode or vibration element as discussed herein. In the variation shown in FIG. 1A, the housing includes a lip 9 around at least a portion of the opening (in this case around the proximal and distal ends of the opening). The lip 9 includes a free portion 11 that is unattached to the housing 3. The free portion 11 of the lip 9 conforms to tissue when placing the housing 3 over an un-even surface. This feature improves the ability of the housing 3 to form a seal against tissue while drawing tissue into the opening to contact the element. The end of the housing 3 includes an opening for a tether 42 (a suture, vessel loop, combination of vessel loop and suture, or other similar structure may be substituted for the tether 42 for convenience, the term tether shall refer to any of these or similar structures). The tether 42 assists in directing the device to an intended site. Although the illustrated example shows a single tether 42, variations of such devices may include two or more tethers 42 to aid in manipulation of the device.

FIG. 1B shows a side view of a distal end of the shaft 4 having the housing 3. Typically, the shaft 4 comprises a multi-lumen tube or extrusion. In the present example, the shaft 4 comprises a three lumen extrusion. The housing 3 also includes an opening (not illustrated) on a bottom portion where the opening exposes an element (also not illustrated).

In use, the practitioner applies suction to the main lumen. The suction draws tissue within the opening, causing contact between the tissue and the element. As noted herein, the probe 2 is useful in creating coagulation lines around soft tissue. However, because the probe 2 may be advanced in contact with irregular tissue surfaces, curvature of the elongate housing 3 may prevent the formation of a vacuum when the opening is not flush against tissue. To address this situation, the probe includes one or more lips 9. The lip 9 may encircle the entire opening or may be located around a portion of the opening. The lip 9 includes a free portion 11 to increase the ability of the opening to form a seal about the tissue. The free portion 11 of the lip 9 provides an increased surface area that is able to flex independently of the housing 3. Accordingly, the free portion 11 of the lip 9 allows portions of the housing 3 to be spaced from the tissue surface without breaking the vacuum generated by the probe 2.

FIG. 1B also shows a tether extending from the housing 3 in a distal direction. The tether is useful to advance the probe around organs. Moreover, the use of two or more tethers may allow "back and forth" manipulation of the housing by pulling alternatively on each tether. The design of the illustrated probe 2 provides a tether 42 that is integral to the housing 3.

Such a feature reduces the size of the connection between the tether 42 and the housing 3 by eliminating the need for a knot or other fastening means to join a tether to the probe.

Figure 1D:
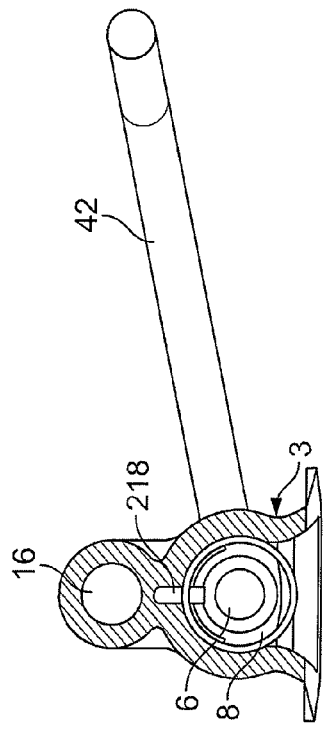
FIG. 1D shows a cross sectional view taken along lines 1D-1D of FIG. 1C.

FIG. 1C illustrates a side-cross sectional view of a probe 2. As illustrated, the elongate shaft 4 contains an elongate housing 3. The housing 4 includes an element 8 within the housing 3, where the element 8 is exposed at the bottom of the housing 3 via an opening 10 in a side wall. In this variation, the element 8 is located within the main lumen 6. A perfusion lumen 16 extends above and parallel to the main lumen 6 directly opposite to the opening. As shown in FIG. 1D, this configuration minimizes a width of the housing 3.

Typically, the fluid delivery lumen (or perfusion lumen) 16 is in fluid contact with the element 8 such that fluid may be delivered to the element and tissue while a suction is applied through the main lumen 6. This action causes tissue to be drawn in to the opening 10 and in contact with the element 8 while the fluid passes over the element and tissue.

Variations of the device where the fluid delivery element 16 is in fluid contact with the element 8 and main lumen 6 offer another benefit for ensuring contact between the target tissue and electrode. In such cases, drawing a vacuum through the main lumen 6 causes a drop in pressure in both the vacuum lumen and, the opening 10 housing the element 8. Placement of the opening 10 against the soft tissue creates a seal against the soft tissue that causes the fluid to flow in the fluid delivery lumen 16. Accordingly, fluid flows from a fluid source through the fluid perfusion lumen across the opening and back the vacuum lumen. If seal is not formed against the soft tissue, then fluid does not flow. Accordingly, the confirmation of fluid flow (or the audible noise confirming a closed fluid circuit) allows the medical practitioner to confirm adequate tissue engagement between the device and tissue. Once adequate engagement is confirmed, the practitioner can energize the electrode during the fluid flow to create the lesion. Breaking of the seal between the opening and the tissue will stop the fluid flow. Accordingly, the presence of fluid flow can serve as confirmation of sufficient engagement with tissue.

In the broadest sense, such device variations allow for a procedure of treating soft tissue where the treatment device forms a fluid circuit comprising the vacuum lumen (being fluidly coupled to a vacuum source), a perfusion lumen (being fluidly coupled to a fluid source), and an opening in the device fluidly coupled to both the perfusion lumen and the vacuum lumen, where the opening contains the electrode. When uncovered, the opening causes the fluid circuit to be an open circuit (i.e., the opening prevents pressure from dropping within the fluid circuit). Accordingly, without the pressure differential in the perfusion lumen, fluid will not flow in the circuit.

Placing the opening against soft tissue closes the fluid circuit and also serves to draw tissue into the opening and against the electrode located within the device. Closing the fluid circuit causes the pressure differential in the perfusion lumen to cause fluid from the fluid source to flow device. Accordingly, given the confirmation of fluid flow, the practitioner is assured that the electrode is in engagement with tissue and may energize the electrode creates the desired treatment in the soft tissue.

Figure 1E:
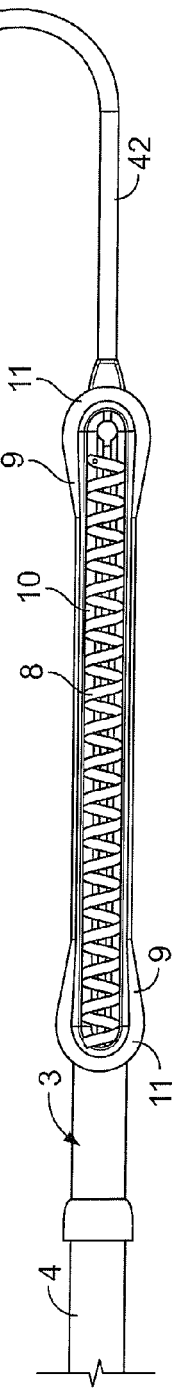
FIG. 1E shows a bottom view of a coagulation probe.

FIG. 1E shows a bottom view of the probe 2 of FIG. 1C illustrating the opening 10 in a side wall of the housing 3 that exposes the element 8. In addition, in the illustrated variation, lips 9 are located around the opening 10 where the proximal and distal ends of the opening 10 include lips 9 with free portions 11.

FIGS. 1C and 1D illustrate the housing 3 as further including a spine member 218. The spine member 218 may provide column strength for the probe 2 and/or housing 3. In some variations of the device, the spine member 218 is elastic or resilient. Alternatively, the spine member 218 may also be malleable, or shapeable to permit shaping of the elongate housing 3 and element 8 for creating coagulation lines having a predefined pattern.

Figure 1F:
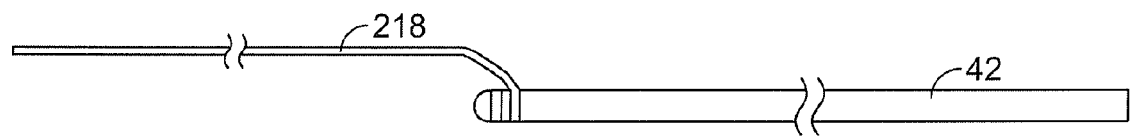
FIGS. 1F to 1G show a spine member attached to a tether and placement of the spine and tether in the elongate housing respectively.
Figure 1G:
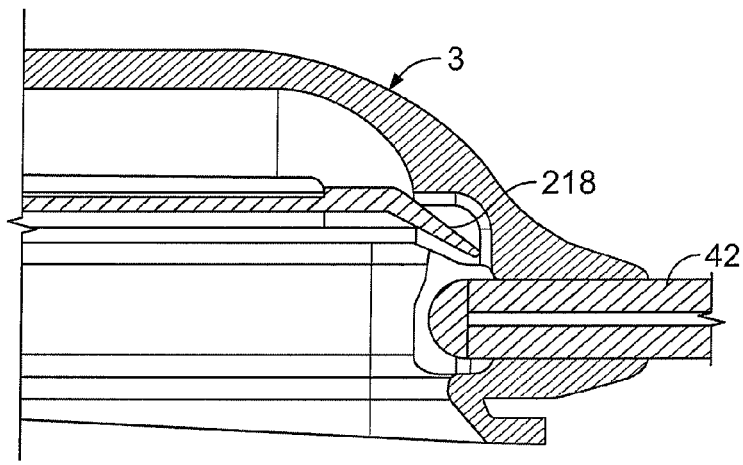

FIG. 1F illustrates a partial view of a spine member 218 connected to a tether 42. The spine member 218 is secured to the tether 42, which ensures that the tether is affixed within the housing. As illustrated in FIG. 1G, variations of the tether 42 may include a section of increased diameter to further assist in retaining the tether within the body.

Figure 1H:
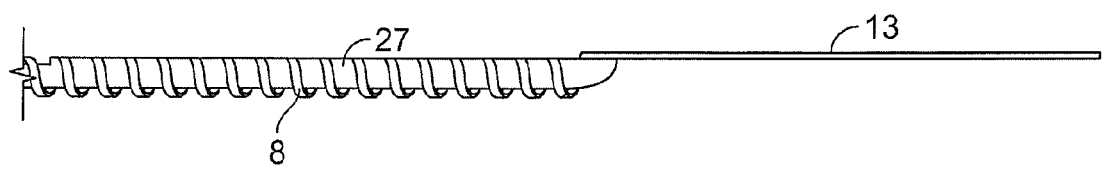
FIG. 1H shows a variation of an element for use with the coagulation probe.

FIG. 1H illustrates an example of an element 8 coupled to a conducting member or wire 13. In this variation, the wire 13 extends through the shaft (not shown) to connect the element 8 to the power supply. Furthermore, the element 8 may optionally include a coagulation sleeve 27. The coagulation sleeve 27 may be used as reinforcement for the element 8. The coagulation sleeve 27 may also serve as a return element such that when tissue contacts the element 8 and coagulation sleeve 27 the tissue completes a circuit allowing current to flow into through the tissue thus coagulating the tissue.

Figure 1I:
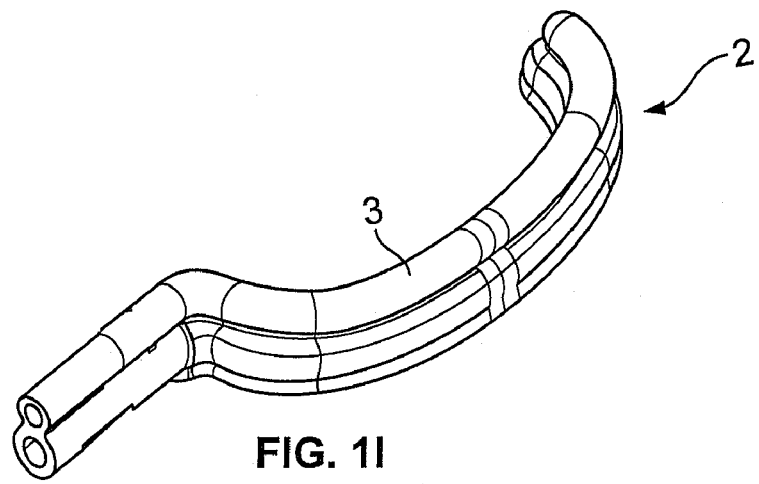
FIGS. 1I to 1K show various shapes of coagulation probes.
Figure 1J:
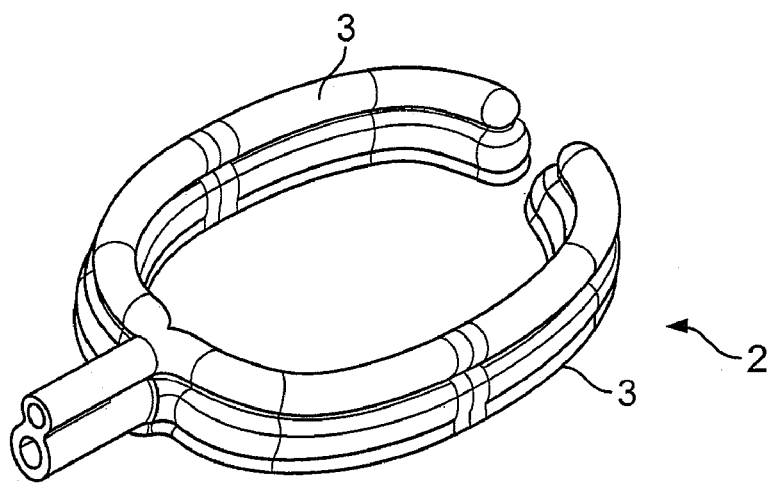
Figure 1K:
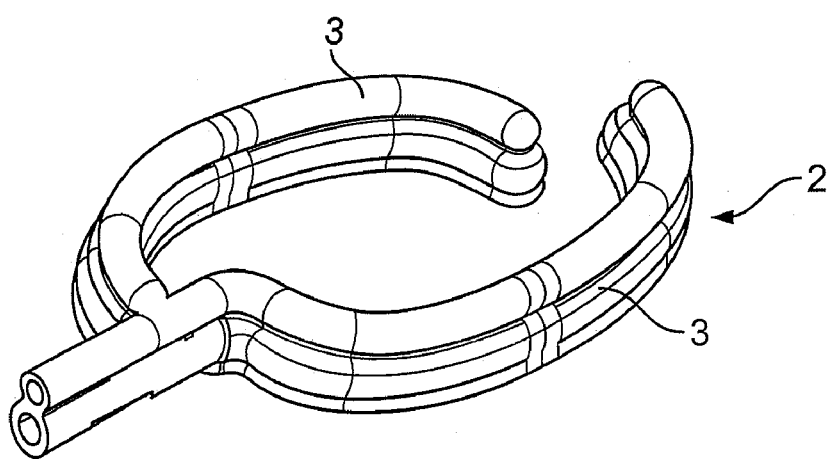

As noted above, variations of the coagulation probe 2 include shapeable spine members that permit the shaft and or housing member 3 to form a specific shape. FIGS. 1I-1K illustrates some examples of such configurations. As shown in FIG. 1I, the elongate housing member 3 may form a partial "C" shape. FIGS. 1J to 1K illustrate yet another variation of the probe 2 in which a single probe includes a branched shaft or elongate housing 2 to produce a probe 2 with dual housings 3 and elements. FIG. 1J shows a variation in which both elongate housing members 3 form similar curved shapes. Such a configuration may be useful when trying to coagulate around vessels or other body structures. FIG. 1K illustrates another variation in which both elongate housing members 3 form curved shapes. However, in this variation, the distal ends of the elongate housing members 3 are offset. Such a configuration is useful to avoid pinching of the vessel or body structure as the elongate members 3 assume the curved shape. For example, the elongate members shown may assume the curved shape via insertion of a stylet into the main lumen where the stylet has a pre-shaped curve.

FIG. 2A shows a perspective view of another variation of a probe housing 3. In this variation, the main lumen 6 extends through a top portion of the housing. The main lumen 6 can be used to provide fluids (e.g., via use of a fluid delivery lumen—not shown). The opening 10 is on the bottom of the housing 3 and contains the element (not shown). As noted above, the main lumen 6 (and any fluid delivery lumen) are in fluid communication with the element to allow simultaneous application of a vacuum and irrigation to the tissue adjacent to the housing 3. The housing 3 includes a lip 9 having a free portion 11 to assist in sealing the device against tissue. Use of this configuration, in which a single lumen runs along the top of the housing 3 allows the ease of incorporating a steering mechanism (as described herein) within the elongate housing 3.

FIG. 2B shows a side cross-sectional view of the housing 3 of FIG. 2A. As shown, the main lumen 6 is located on a top portion of the housing 3 while the perfusion lumen (not shown) is parallel to the main lumen 6. Both lumens are opposite to the opening 10 in a sidewall of the housing 3. In this variation, the element (not shown) is affixed within a separate cavity 17 that is in fluid communication with the main lumen 6 and perfusion lumen. The illustrated variation also includes a lip 9 having a free portion 11 to assist in formation of a seal against tissue.

FIG. 2C illustrates another variation of a probe 2 that is similar to that shown in FIGS. 2A to 2B. In this variation, there is a single main lumen 6 in a top portion of the housing 3. The main lumen 6 and cavity 17 are in fluid communication at the distal end of the housing 3. A separate fluid perfusion lumen 16 advances through the main lumen and into the proximal portion of the cavity 17. This configuration allows delivery of fluid at one end of an element 8 while aspiration is provided at the other end. The resulting action is the creation of a vacuum at the opening 10 and against tissue while fluid from the fluid delivery lumen 16 passes over the tissue and element 8. Although not shown, electrical connection for the element 8 may be passed through the main lumen 6. Furthermore, the shape of the elongate housing 3 may permit ease of positioning.

FIG. 2D shows a bottom view of the probe 2 of FIG. 2C. As shown, the perfusion lumen 16 extends to a first side of the element cavity 17 while the main lumen 6 terminates at an opposite side of the electrode cavity 17. Furthermore, the shape of the housing 3 containing the main lumen 6 may be circular to ease positioning of the housing 3.

FIGS. 2E-2L show another aspect for use with the probes 2 described herein. In this aspect, the probe 2 configuration accommodates a track 300. The track 300 may be any guide type member that operates as a track or rail for navigation, steering, or shaping of the probe 2. The track 300 includes a variety of devices such wires, steerable catheters, steerable guide-wires, shaped tubes or mandrels, etc. (where such guide devices will be referred to as "track" or "rail"). Optionally, the track 300 may be keyed, have a groove, or have any other feature that permits maintaining the orientation of the track 300 with the probe 2.

Figure 2E:
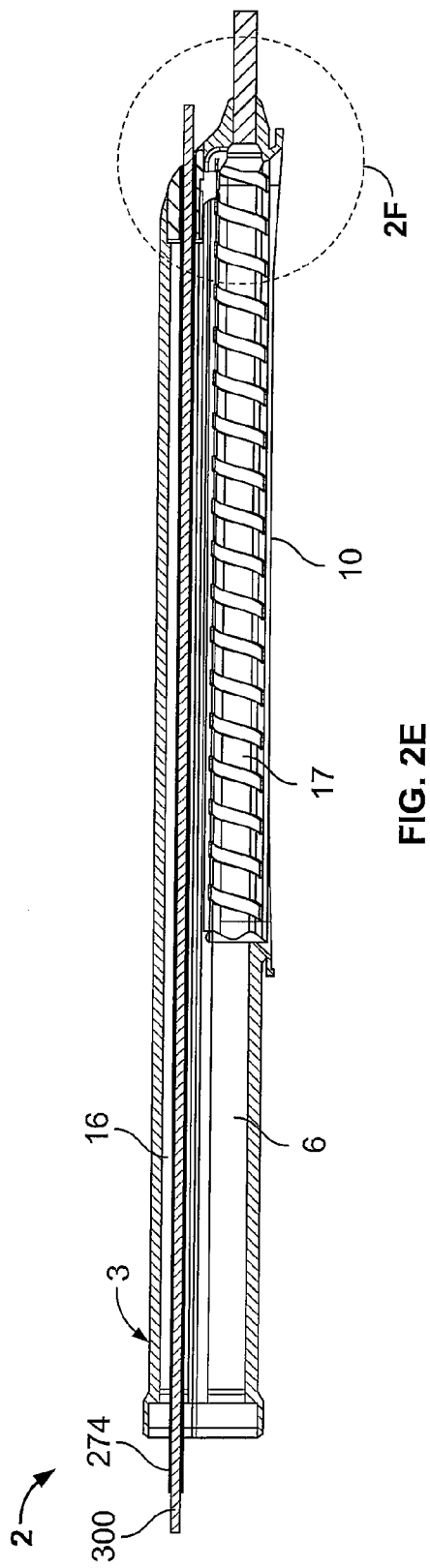
FIG. 2E shows a variation of a coagulation probe having features to accommodate a track member used to position the probe.

FIG. 2E illustrates a partial cross-sectional view of a probe 2 having a track 300 extending through a housing 3. In this variation, the probe 3 can include a track tubing 274 having a track lumen 276 for accommodation of the track 300. In certain variations of the probe 2, the track lumen 276 is fluidly isolated from other portions of the probe 2 and/or housing 3. For example, it may be desirable to fluidly separate isolate the track lumen 276 from fluid flow in a perfusion lumen 16, vacuum lumen 6, main cavity 17, shaft (not shown) or other portion of the device 2. Fluidly isolating the track lumen 276 provides a number of functional benefits such as preventing passage of current to the track 300, maximizing vacuum at an opening 10 of the housing 3, preventing perfusing fluid from escaping through the distal end of the probe 2. However, it is understood that variations of the probe 2 include use of track lumens that are not fluidly isolated from the remainder of the device. Moreover, in additional variations of the probe 2, a track lumen 276 may be integral with the housing 3 or shaft of the probe 3 and may not require the use of a separate track tubing 274.

Although not shown, the variation of FIG. 2E may include any number of openings in the top of the housing 3. Such openings can allow for increased flexibility of the probe housing. In such a case, the perfusion lumen serves to function as the track lumen.

Figure 2F:
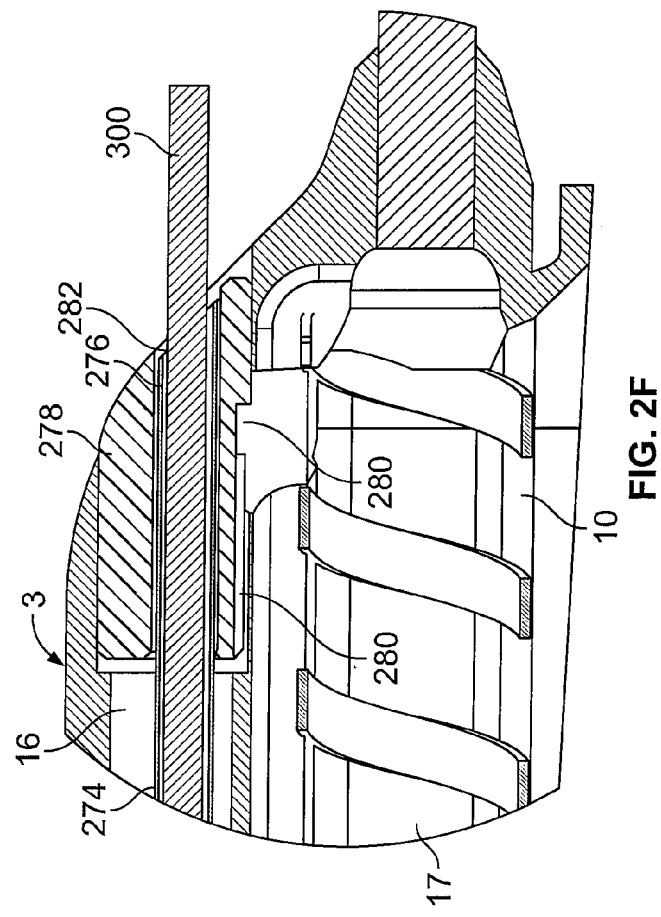
FIG. 2F shows a detail view of a probe housing with a track extending out of a track lumen of the housing.

FIG. 2F illustrates a magnified view of section 2F from FIG. 2E. As shown, the track 300 extends through the track lumen 276 and through a distal end of the probe housing 3. In this example, the track tubing 274 extends through the perfusion lumen 16 of the probe 2. Accordingly, one or more channels 280 can be used to fluidly couple the perfusion lumen 16 to the main cavity 17. A separate channel 282 can be used to allow the track lumen 276 to exit the device. While the channels 280, 282 may be integrally formed with the housing 3, a simpler alternate approach may include the use of a plug 278.

Figure 2G:
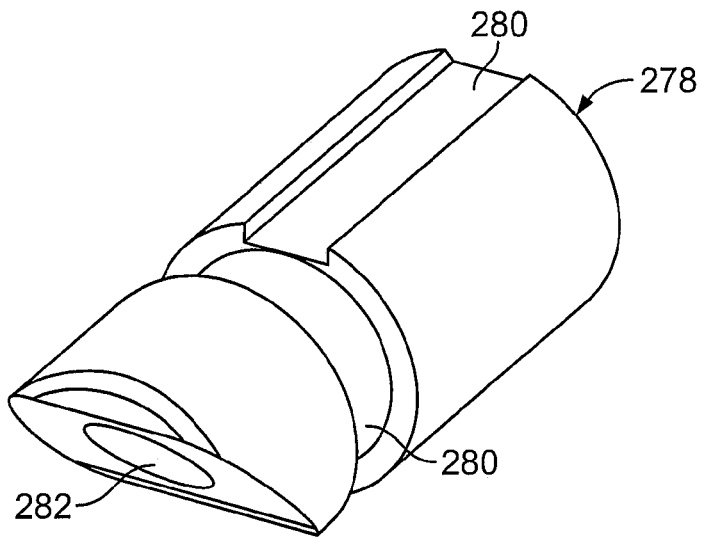
FIGS. 2G to 2I show a variation of an optional plug used to couple a perfusion lumen with a main cavity.
Figure 2H:
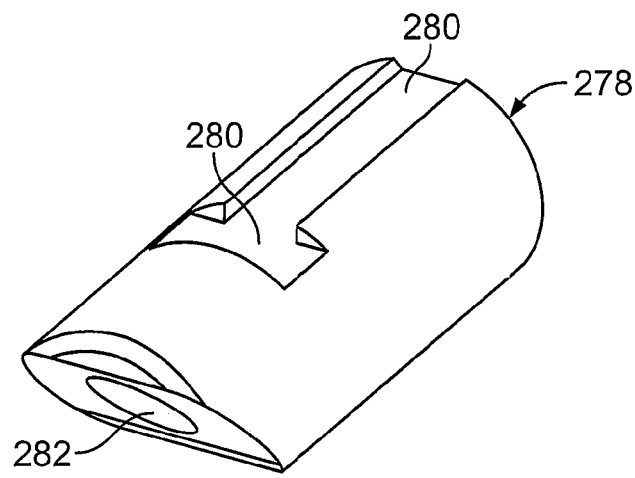
Figure 2I:
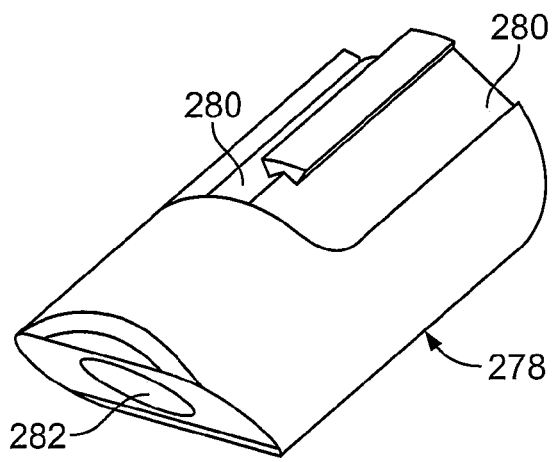

FIGS. 2G to 2I show variations of plugs 278 for use as described above. It is understood that any number of variations of such a plug are within the scope of the invention. The illustrated plugs 278 are rotated to more clearly illustrate a first, channel 280 that allows for fluidly coupling a perfusion lumen to the main cavity of the probe. A second channel 282 extends through the plug 278 to allow passage of the track lumen. Such plugs 278 can provide additional structural improvements for the probe. For example: the second channel 282 can be sized to closely fit any track tubing and/or serve as a location for an adhesive to retain the track tubing; the plug 278 can isolate the perfusion fluid from exiting the device at the distal end; the plug 278 can also act as a strain relief against the track 300 and prevent inadvertent cutting or damage to the housing by the track; etc.

FIG. 2J illustrates a partial cross sectional view of another variation of a probe 2 having a track 300 extending through a housing 3. In this variation, the track 300 extends through a vacuum or main lumen 6 and main cavity 17 rather than through the perfusion lumen 16. This variation may or may not use a track tubing 274.

FIGS. 2K to 2L show one example of a method of using a probe 2 with a rail 300 and rail lumen. As shown in FIG. 2K, a track 300 is placed proximate to tissue or the area to be treated. Although a track 300 may be used by itself, the track 300 may also be used with or be a part of an access device 182. Examples of such access devices may be found in: U.S. Patent Provisional Ser. No. 60/726,342, filed Oct. 12, 2005, entitled "Diaphragm Entry for Posterior Access Surgical Procedures"; U.S. patent application Ser. No. 11/408,315, filed Apr. 21, 2006, entitled "Diaphragm Entry for Posterior Surgical Access"; U.S. patent application Ser. No. 11/408,307, filed Apr. 21, 2006, entitled "Diaphragm Entry for Posterior Surgical Access"; U.S. patent application Ser. No. to be assigned, filed on the same day as this application, entitled "Diaphragm Entry for Posterior Surgical Access", Ser. No. 11/737,493, the entirety of each of which is hereby incorporated by reference.

In addition, while the track 300 is shown as forming a loop, the track 300 may form any open or close shape or profile whether 2 dimensional or 3 dimensional as required by the particular procedure. For example, the track 300 may be a shapeable or pre-shaped mandrel that forms an open "J" type profile. In another example a track 300 may have a 2 dimensional shape but through manipulation by the surgical practitioner, the track 300 and probe 2 may conform to the surface of the tissue being treated.

FIG. 2L shows a probe 2 advancing over the track 300 and conforming to the profile of the track 300 As noted herein, when properly positioned, the probe 2 may apply suction to engage the tissue against the probe's element. The probe 2 simultaneously, or sequentially, apply a perfusing fluid to the area being treated.

Figure 3A:
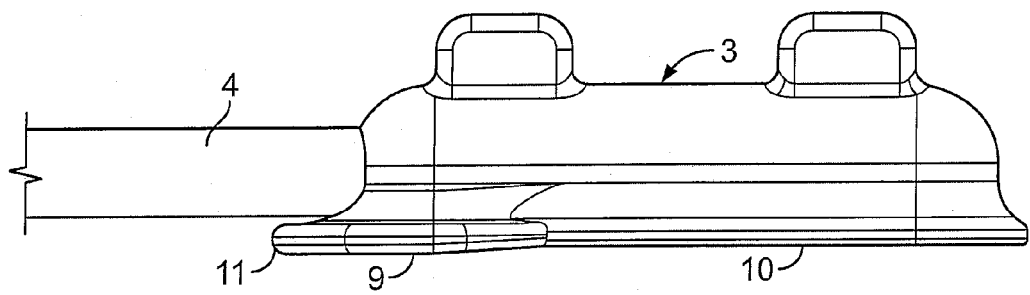
FIGS. 3A to 3C illustrate a variation of a sensing probe having features described herein.
Figure 3B:
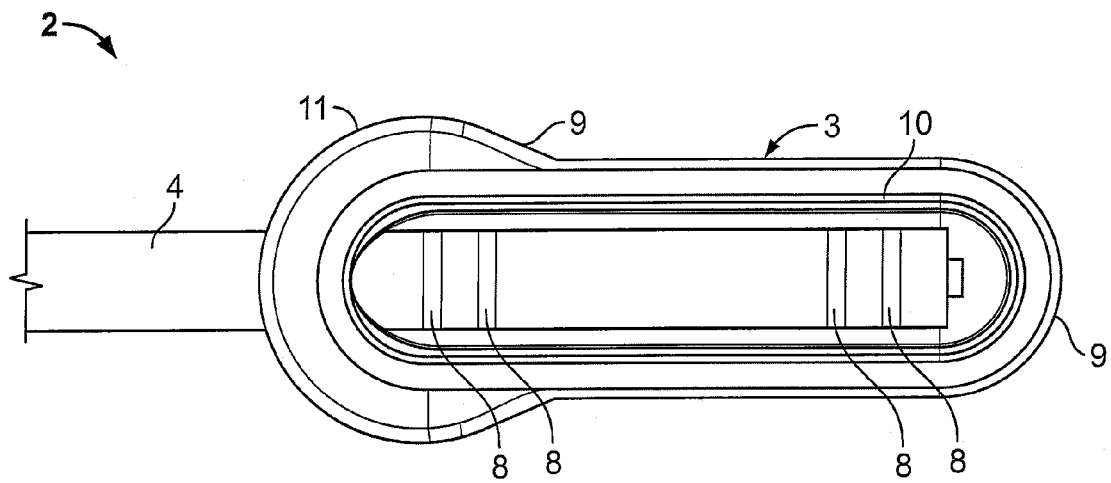
Figure 3C:
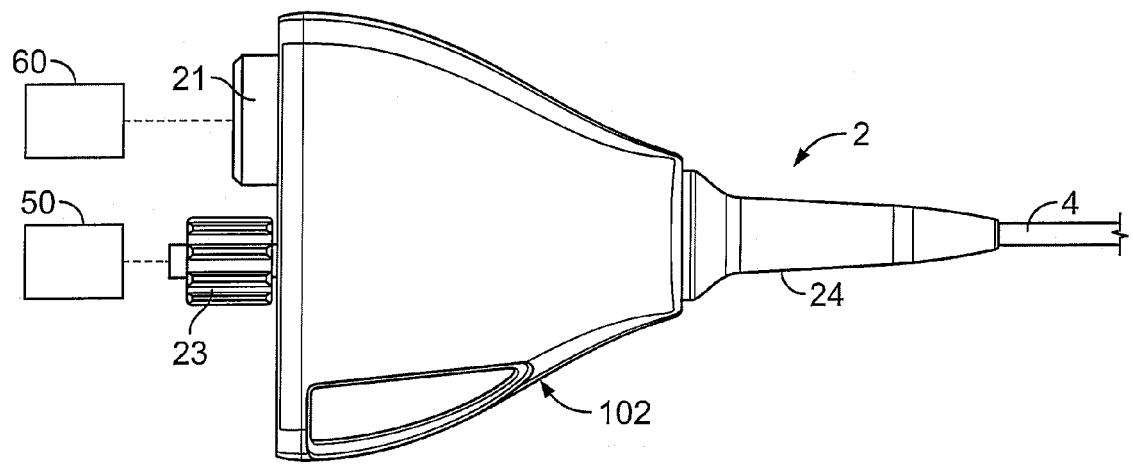

FIGS. 3A to 3C illustrate another variation of a vacuum probe 2. FIG. 3A illustrates a side view of a housing 3 of the vacuum probe 2 located at the end of a shaft 4. As described herein, the housing 3 of the probe will be flexible to accommodate maneuvering of the probe 2 to the site and to conform to tissue surfaces for formation of a seal. In this variation, the elongate housing 3 includes a lip 9 around an opening 10 where the lip 9 has a free portion 11 at a proximal end of the opening. However, variations of the device include an opening having the free end of the lip extending around the perimeter of the opening.

FIG. 3B illustrates a bottom view of the probe 2 of FIG. 3A. The housing 3 comprises an opening 10 in a sidewall to expose two pairs of electrodes 8. Such a combination may be used to map electrical pathways within tissue to determine the proper areas to form coagulation lines. The electrodes 8 can be affixed to the shaft 4 within a main lumen 6 of the housing 3. Moreover, the shaft 4 may have a lumen in fluid communication with the main lumen 6 such that when coupled to a vacuum source, the opening 10 and lip 9 forms a seal against tissue drawing the tissue into contact with the electrodes 8.

FIG. 3C shows a top view of a handle 102 for use with the probe of FIGS. 3A and 3B. In this variation, because the probe 2 is useful for mapping, the handle 102 comprises a connector 21 for a power supply 60 and a vacuum connector 23 for coupling the device 2 to a vacuum source 50. Though not shown, variations of the device include a handle 102 with an additional fluid supply connector.

Figure 4A:
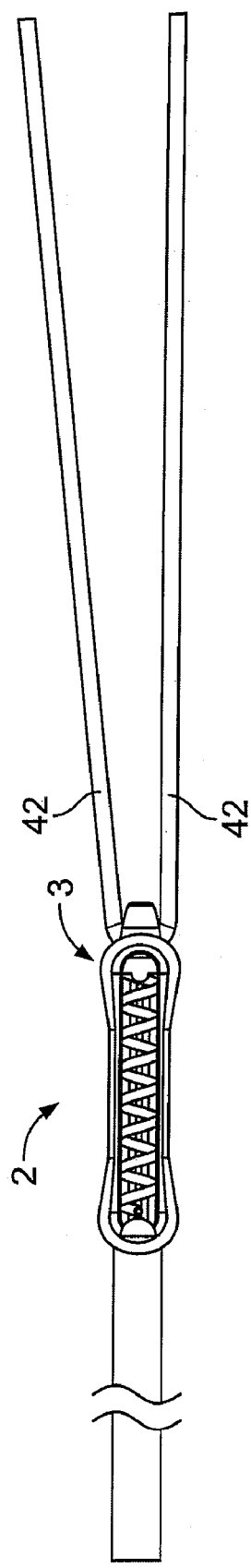
FIG. 4A shows a variation of a double tether affixed to an elongate housing.

FIG. 4A illustrates a sample probe 2 having multiple tethers 42 attached to the distal end of the housing 3. As noted herein, the multiple tethers 42 permit a manipulation of the housing 3 by alternatively pushing and pulling on either tether 42.

Figure 4B:
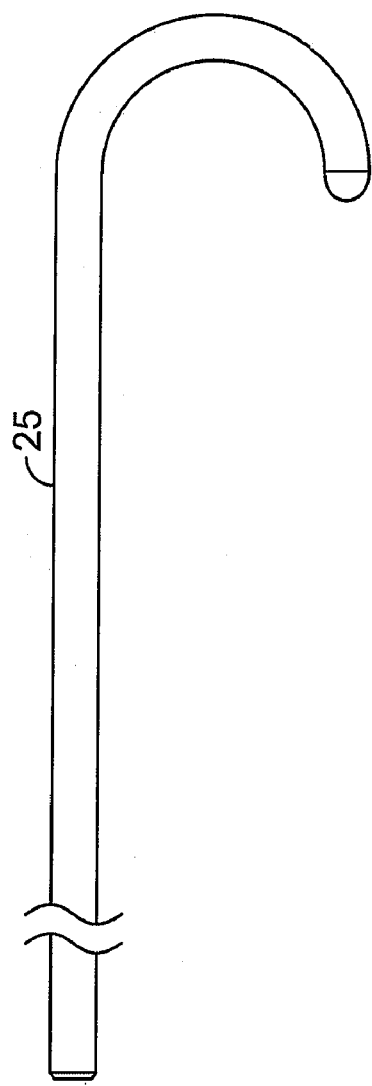
FIG. 4B shows an example of a guiding stylet for use with various probes.

FIG. 4B shows a curved or shapeable stylet 25 as mentioned herein. When used, the stylet 25 is typically inserted into the main lumen to shape the distal end of the probe into a desired shape. In some variations, the stylet 25 will be flexible and the shaft of the probe sufficiently rigid such that the does not affect the shape of the probe until it reaches the housing portion. Alternatively, or in combination, a variety of steerable members may be used in place of the stylet.

Variations of shaft 4 described herein may be fabricated from a polymer such as PEBAX®, polyester, polyurethane, urethane, silicone, polyimide, other thermoplastic, thermoset plastic, or elastomer. Alternatively, the shaft 4 may be a metal (e.g., titanium, etc.), or metal alloy (e.g., stainless steel, spring steel, nickel titanium, etc.) fabricated as a cut tube, braided wires, a mesh, one or more helically wound wires, or other configuration encapsulated in or covered by a polymer. When using polymer coverings/insulation 7 over tissue heating electrode(s) or vibrational element(s) 8 and/or the shaft 4, the covering/insulation 7 may be extruded, injection molded (especially when incorporating discrete features such as the opening without requiring another step of cutting the covering/insulation around the defined electrode, vibrational element), dipped, or applied using another manufacturing process involving embedding or covering the electrode, vibrational element, and/or shaft support structures with the polymer covering.

As discussed herein, the element 8 may comprise an electrode or a vibrational element. When transmitting radiofrequency energy in unipolar fashion between at least one electrode 8 and a large surface area, a reference electrode (not shown) is placed on the subject's body remote from the electrode 8 and a single wire is routed to each electrode and connected to a radiofrequency generator 60. When transmitting D.C. or radiofrequency energy in bipolar fashion between pairs of electrodes 8, individual wires are connected to each of two or more individual, closely-spaced electrodes 8 and RF or DC energy is applied between the electrodes using a radiofrequency or direct current generator 60.

When utilizing resistive heating of the electrode 8 and relying on conduction to transfer heat to contacted tissue, wires are connected to each electrode 8 (e.g., resistive element in this case) separated by a length defining the region to be heated so the tissue contacting length of the electrode 8 heats to the desired temperature and the heat is conducted to contacted tissue. In a resistive heating approach, the electrode(s) may advantageously be constructed from Nichrome wire or other stock material as this material is commonly used in resistance heaters.

When mechanically vibrating the vibrational element(s) 8 axially or radially at a high rate (e.g., 5 kHz to 1 MHz and preferably 15 kHz to 30 kHz) and small displacements (preferably <1 mm in each direction), vibrational element(s) 8 are connected to a drive shaft that is coupled to a linear motor 70 or a rotary motor 80 that causes the cyclic micro-displacement and invokes an ultrasonic signal from the movement of the vibrational element(s) 8 relative to the contacted soft tissue. The ultrasonic signal propagates through the soft tissue structures causing cavitation that induces heating of the soft tissue and renders the soft tissue electrically nonviable.

Temperature sensors may be associated with each electrode/vibrational element 8 with temperature sensor wires routed along the shaft to the handle where they are connected to another electrical connector capable of transmitting the temperature signal to a radiofrequency generator 60 with temperature monitoring or control capabilities or a separate temperature monitor. U.S. Pat. No. 5,769,847, entitled "Systems and methods for controlling tissue ablation using multiple temperature sensing elements" which is incorporated herein by reference, describes tissue coagulation systems utilizing multiple electrodes and temperature sensors associated with each electrode to controllably transmit radiofrequency energy and maintain all electrode(s) essentially at the same temperature. The vacuum coagulation probe electrode(s) or vibrational element(s) and associated temperature sensors may be connected to such a mechanism to control transmission of radiofrequency or mechanically-induced ultrasonic energy to each electrode/vibrational element to control the heating of contacted soft tissue.

Variations of the integrated vacuum coagulation probes described herein exposes electrode/vibrational element 8 only along one side of the vacuum-integrated coagulation probe and insulates the opposite side against transmission of radiofrequency or ultrasonic energy, and heat to collateral, non-targeted tissue structures These openings 10 enable producing a vacuum attachment with the probe 2 against the soft tissue throughout the length of electrode(s) 8, thereby ensuring intimate and direct tissue contact between the electrode(s)/vibrational element(s) 8 and the soft tissue. The openings 10 also orient the edges of the electrode(s)/vibrational element(s) 8, commonly associated with high current densities (when using radiofrequency energy) transmitted into the soft tissue, to create a continuous, consistent lesion throughout the length of the electrode(s) 8 without producing hot spots that interfere with creating lesions having consistent depth and width. The combination of creating intimate tissue contact and directing the current density profile creates controlled and efficient heating of the soft tissue required when coagulating tissue to produce defined lengths of transmural lesions in atrial tissue (or other soft tissue).

When using mechanically-induced ultrasonic energy, the openings 10 define edges along the electrode(s)/vibrational element(s) 8 that produce friction as the vibrational elements move relative to the soft tissue surface and cause vibration of the soft tissue and surrounding fluid which induces an ultrasonic waveform that propagates throughout the soft tissue causing cavitation that results in heating of the soft tissue. The pore(s)/opening(s) 10 may have a constant width or vary along the length of the electrode/vibrational element 8 to adjust contact forces throughout the length of the electrode(s)/vibrational element(s) 8.

The vibrational element(s) 8 may be moved via a drive shaft that is coupled to a linear motor for axial displacement or a rotary motor for radial angular displacement (each, referenced above). When utilizing a linear motor to induce the displacement of the vibrational element(s) relative to the soft tissue, the windings are advantageously oriented substantially perpendicular to the probe axis or at an acute angle from this perpendicular plane to enhance the transmission of high frequency mechanical displacement into ultrasonic propagation waves capable of causing cavitation of soft tissue and the resulting heat. When utilizing a rotary motor to induce angular displacement of the vibrational element(s) relative to the soft tissue, the windings are advantageously oriented substantially parallel to the probe axis or at an acute angle from the probe axis.

Figure 28A:
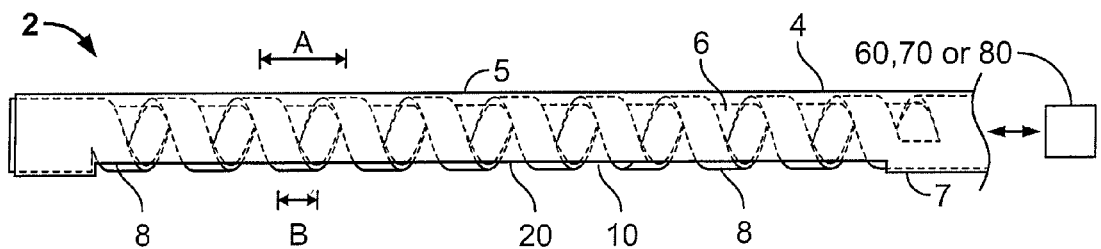
FIGS. 28A to 28C show a side view, a perspective view, and a bottom view of the distal section of an integrated vacuum coagulation probe variation.
Figure 28C:
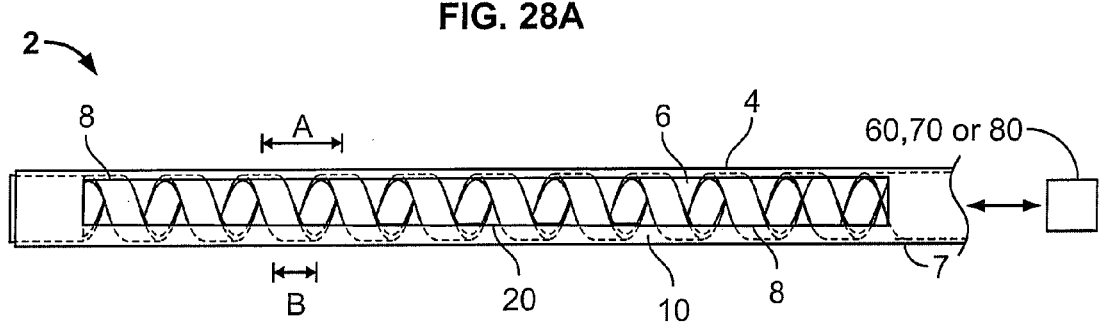

The electrode(s)/vibrational element(s) 8 may be fabricated from metal (e.g., tungsten, titanium, tantalum, platinum, gold, silver), metal alloy (e.g., stainless steel, spring steel, nickel titanium, platinum iridium, silver chloride, etc.), metals deposited over a carrier (e.g., gold-plated stainless steel, gold deposited polyimide, platinum deposited polyester, etc.) or a combination of materials fabricated, with methods described previously, to define the shape, the coil/winding width B, the coil pitch A (e.g., as shown in FIGS. 28A, 28C) or separation/gap (for non-helical configurations as shown in FIGS. 29A to 29D), shaft 4 attachment features (e.g., threads, slots, etc.) or other features. The electrode(s)/vibrational element(s) 8 may be fabricated from elastic or superelastic conductive materials so they can be deflected upon exposure to an external force (e.g., actuation of the vacuum, manual bending, etc.). Alternatively, they may be fabricated and treated such that the electrode(s)/vibrational element(s) 8 is/are malleable so the operator may tailor the electrode(s)/vibrational element(s) 8 to the anatomic structures. Similarly, the shaft 4, described above, may be adapted to be malleable.

The perfusion tube 100 or lumen 16, disclosed herein, can serve multiple functions. The perfusion tube 100 or lumen 16 may be fabricated from a malleable metal or alloy to enable the operator to impart a shape to the distal section 5 that contains the electrode/vibrational element 8 and/or shaft 4 and maintain that shape during placement and/or coagulation. Alternatively, the perfusion tube 100 or lumen 16 may be fabricated from a polymer tube or a braided polymer tube, or be integral to or embedded into the covering/insulation using an injection molding or extrusion process that defines a separate lumen. Stylets having discrete shapes and/or malleability may be inserted through the perfusion tube 100 or lumen 16 to adjust the shape of the probe during placement or coagulation. Alternatively, a separate steering mechanism may be inserted through the perfusion tube 100 or lumen 16 to remotely maneuver the probe. Such remote manipulation features are especially relevant during less invasive procedures. The perfusion tube 100 or lumen 16 incorporates at least one outlet, aperture, or cut-out 26 along the distal end and is routed to a port at the handle 102 of the probe to enable passive fluid cooling of the tissue during lesion creation. The suction force applied by a vacuum source 50 through the shaft vacuum lumen 6 may be used to pull fluid (e.g., saline, Ringer's solution, plasmalite, etc.) from a fluid source 55 (e.g., saline bag) through the perfusion tube 100 past the distal outlets, or cut-outs 26 and along the lumen 6 of the probe conducting heat away from the soft tissue surface directly engaged against the electrode/vibrational element 8. The known/constant diameter and length of the perfusion tube 100 or lumen 16 combined with the known/constant pressure applied through the probe (e.g., −200 mmHg to −1400 mmHg; preferably −400 to −600 mmHg) will then produce a constant fluid perfusion through the probe without the need for a separate pump/injector.

The principle factor considered important in the improvement in the lesion creation capability observed in these integrated vacuum probe variations is the integration between the electrode/vibrational element 8 and the vacuum coupling 6. In the variations of the invention, the vacuum source 50 applies suction directly through openings 10 in the electrode(s)/vibrational element(s) 8 to force soft tissue directly in contact with the electrode(s)/vibrational element(s) 8. As opposed to alternative, inferior approaches which contain suction means and ablation structures that are independent and separated where suction is applied to tissue adjacent to and separate from tissue that contacts the electrode, by applying suction to soft tissue directly contacting the electrode/vibrational element 8 according to variations of the invention, the soft tissue is forced into the openings 10 between windings of the electrode(s)/vibrational element(s) 8 and into engagement with the electrode(s)/vibrational element(s) throughout the length consistently. Furthermore, variations of the present invention may tailor the pitch (A) and winding width (B) so the probe electrode/vibrational element 8 contacts the soft tissue at spaced intervals (either consistent or varied) thereby optimizing the current density profile (when transmitting RF energy) or the vibrational waveform (when mechanically inducing ultrasonic energy) along the length of the electrode/vibrational element and reducing the disparity in current density or ultrasound waveform observed throughout the length of the conventional ablation probes. These factors enable the variations of the invention to create consistent lesions having defined dimensions without the need for several lesion monitoring tools (e.g., temperature sensors, etc.).

FIGS. 5A and 5B show an assembled vacuum-integrated coagulation probe 2. FIGS. 6A to 6F show the distal section 5 of the vacuum-integrated coagulation probe 2 in FIGS. 5A and 5B. The assembled vacuum-integrated coagulation probe incorporates a distal section 5 that comprises at least one electrode/vibrational tissue heating element 8 encapsulated in a covering 7 that has an aperture 20 along a segment, that exposes the conductive windings and openings 10 between winding that are coupled to the vacuum lumen 6, which defines the electrode/vibrational element 8. The electrode/vibrational element 8 provides structural integrity of the distal section 5 while defining a central vacuum lumen 6 and openings 10 between individual, separated windings. The distal section 5 is coupled to a handle 102 by a shaft 4 that comprises an extension of the electrode/vibrational element 8 or a tubular (single or multiple lumen) member containing electrical wires or a drive shaft that are secured to the electrode/vibrational element 8 and routed to an electrical connector or mechanical coupler at the handle. A vacuum port that is coupled to the vacuum lumen 6 is connected toga vacuum source 50. A fluid perfusion port is coupled to the perfusion tube/channel 100 and is connected to a fluid source 55. The electrical wires (for variations involving transmission of radiofrequency energy) are connected to a radiofrequency generator 60. For variations involving mechanically-induced ultrasonic energy, the drive shaft is coupled to a linear motor 70 or rotary motor 80 that imparts high frequency, small displacement cyclic movement of the drive shaft thus the vibrational element relative to contacted soft tissue.

As shown in FIGS. 6A to 6F, this example of a vacuum-integrated coagulation probe 2 comprises a dual lumen tubing fabricated from a non-conductive polymer 7 extruded or injection molded into a dual lumen tubing having a side wall with at least one aperture 20, a distal tip that caps the distal end of the lumens 6 and 16 and defines an opening 40 through which another separate tubing, tape, or suture can be secured to manipulate the probe; and an electrode/vibrational element 8 partially encapsulated in or otherwise secured to the dual lumen tubing. The at least one electrode/vibrational tissue heating element 8 comprises at least one pore or opening 10 coupled to the first lumen 6 of the multilumen tubing, as shown in FIGS. 6A to 6F. The fluid perfusion tube 100 (which may also function as a channel for inserting a steering mechanism or preshaped stylets that enable maneuvering the device) defines a lumen 16 that is coupled to the vacuum lumen 6 through an outlet 26.

As shown in FIGS. 6A to 6F, the perfusion lumen 16 defined by the multi-lumen tubing routes fluid from a fluid source 55 through a fluid perfusion port at the handle, through a outlet 26 between the fluid perfusion lumen 16 and the vacuum lumen 6, along the electrode/vibrational element 8, along the proximal region of the shaft 4, and through a vacuum port at the handle, and to the vacuum source 50 to enable hydrating and fluid cooling of soft tissue contacting the electrode/vibrational element 8. Perfusion of fluid through the multilumen vacuum probe enables cooling soft tissue during coagulation to enable transmitting more energy into the soft tissue thereby conducting the heat further into the tissue and creating deeper lesions.

FIGS. 7A through 7I show an alternative multilumen vacuum-integrated coagulation probe 2 variation. FIGS. 7A to 7D show an isometric view, a bottom view, a side-sectional view, and a side view of the multilumen vacuum-integrated coagulation probe 2. FIGS. 7E to 7I show cross-sectional views of the probe. As shown in FIGS. 7B, 7C, 7G, and 7H, this vacuum-integrated coagulation probe 2 variation incorporates ribs 30 that reinforce the covering 7, especially at the aperture 20 in the covering 7, without blocking a substantial cross-section of the vacuum lumen 6 (as shown in FIGS. 7G and 7H). These ribs 30 maintain separation between opposing sides of the covering 7, especially along the aperture 20, as the distal section 5 of the probe 2 is deflected or positioned into curved shapes. In addition, the ribs 30 do not interfere with the ability of the electrode/vibrational element 8 that is exposed through the aperture 20 to contact soft tissue. As such, the ribs 30 ensure the aperture 20 maintains it's geometry where the width C of the aperture exceeds the offset D between the plane of the aperture to the surface of the electrode/vibrational element to ensure soft tissue is forced into the aperture and into contact with the electrode/vibrational element as vacuum is applied from a vacuum source 50 to the vacuum lumen 6. The number and/or width of the ribs may be varied as well as their geometry. However configured to avoid interference as discussed above, the purpose of the ribs, braces or struts 30 is to limit or prevent either one or both of outward buckling of the covering wall when bending or otherwise manipulating the body, or wall collapse (laterally and/or vertically) once a vacuum seal has been established between tissue and the device.

Figure 27A:
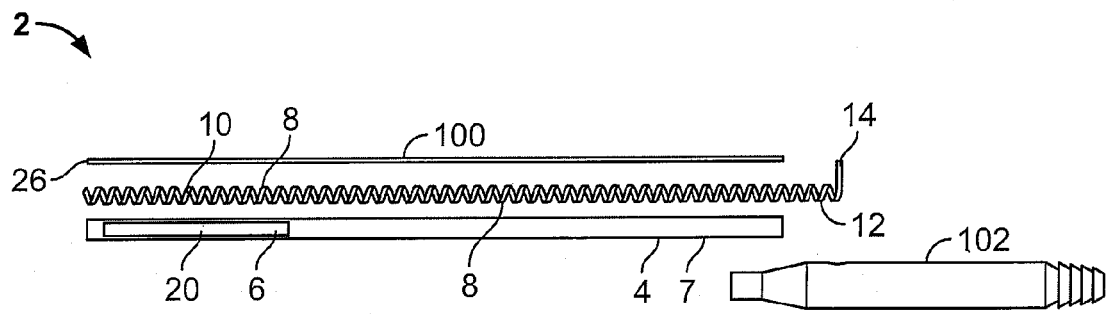
FIGS. 27A to 27C show an exploded view, a bottom view, a close-up view, respectively, of an integrated vacuum coagulation probe variation of the invention.
Figure 27B:
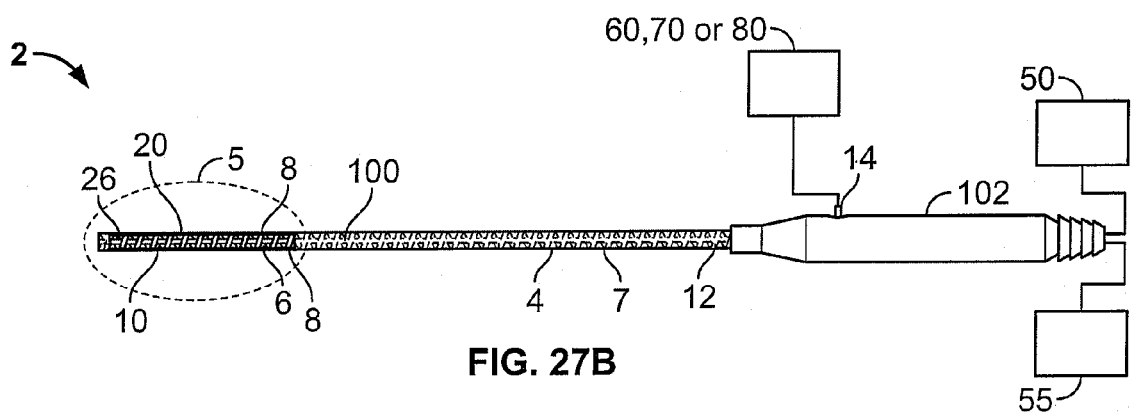
Figure 27C:
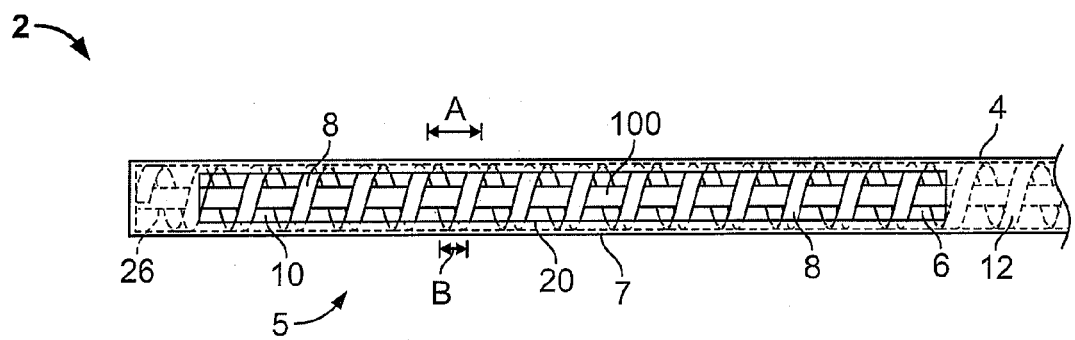

FIGS. 27A to 27C show an exploded view, a side view, and a close-up view of another integrated vacuum coagulation probe 2 variation of the invention. Probe 2 incorporates a shaft 4 that defines a lumen 6, as shown in FIG. 27A.

Shaft 4 shown in FIGS. 27A to 27C comprises of a polymer, such as listed above, covering or encapsulating a rectangular (or elliptical or circular, etc.) wire wound into a helix (alternatively, a mesh, intersecting helices, or other configurations of windings can be utilized) throughout a majority of the probe length with a section of the polymer removed to create an aperture 20 through which the suction pore(s) or opening(s) 10 between windings of electrode/vibrational element 8 are coupled to lumen 6, and the conductive surface of electrode/vibrational element 8 is exposed.

As such, the inventive variation in FIGS. 27A to 27C comprises a vacuum-integrated coagulation probe fabricated from four components: 1) a fluid perfusion tube 100 that incorporates at least one aperture 26 at its distal end; 2) an electrode/vibrational element 8 and integral shaft support coil connected to a small diameter electrical conduit or a larger diameter drive shaft 12 that contains sufficient column strength to rapidly move the electrode/vibrational element axially or radially; 3) a shaft 4 and a covering 7 that defines at least one aperture 20 along the electrode/vibrational element 8 and coupled to the opening(s) 10 between windings of the electrode/vibrational element 8; where the shaft 4 is connected at the handle 102; and 4) a handle 102 that houses at least one electrical connector 14 for electrodes, or at least one mechanical coupler 14, for vibrational elements, and ports that couple the lumen 6 of the shaft 4 to a suction device 50 and the lumen of the fluid perfusion tube 100 to a fluid source 55. The electrical connector/mechanical coupler 14 is routed to a radiofrequency or direct current generator 60, when energy is transmitted to electrodes, or a mechanical vibration mechanism (e.g., linear motor 70 or rotary motor 80), when mechanically-induced ultrasonic energy is transmitted to vibrational elements. Alternatively, the section of the probe containing the exposed segment of the electrode/vibrational element 8 and the cut-out region(s)/aperture(s) 20 of the covering 7 that exposes the suction pore(s)/opening(s) 10 through the electrode(s)/vibrational element(s) 8 may be fabricated from one or more separate component(s) than the shaft.

The shaft 4 and/or distal section 5 of the probe housing the electrode/vibrational element 8 and suction pore(s)/opening(s) 10 may have a circular cross-section, elliptical cross-section, rectangular cross-section, or other geometry depending on the stiffness requirements, access characteristics, and other considerations. The shaft 4 may be fabricated as a single lumen tubing as shown in FIGS. 27A to 27C or alternatively multi-lumen tubing having two or more separate lumens serving specific functions. At its proximal end, a portion of the shaft 4 is bonded to a handle 102 that optionally incorporates at least one port that feeds the shaft lumen(s) 6 and the lumen 16 of the perfusion tube 100. The port(s) may incorporate luer adaptor(s) or other tubing connector(s) to facilitate attaching IV tubing, surgical tubing, or other tube capable of connecting to a vacuum source 50.

The handle 102 may also house at least one electrical connector or mechanical coupler 14 to which the electrical wire(s) or drive shaft(s) 12 are attached at the proximal end. The wire(s) or drive shaft(s) 12 will then be routed to the electrode(s) or vibrational element(s) 8 to enable transmitting energy (radiofrequency, or mechanically-induced ultrasonic energy respectively in these examples).

In the variation in FIGS. 27A to 27C, the helical wire functions both as an electrode or vibrational type tissue heating element 8, and the signal wire or drive shaft 12. When the electrode or vibrational element is not integral to the shaft, discrete signal wire(s) or drive shaft(s) 12 are typically secured to the electrode or vibrational element 8 and are routed to the electrical connector or mechanical coupler 14, respectively, at the handle 102.

As shown in FIGS. 27A to 27C, at least one aperture 20 is created along one side of the coagulation probe through the side wall of the covering/insulation 7 to expose the conductive surface of the conductive windings 8 and pores/openings/gaps 10 between windings, and coupling the lumen 6 of the shaft 4 to the exposed surface of the helical wire thereby defining the integrated electrode(s)/vibrational element(s) 8.

Figure 28D:
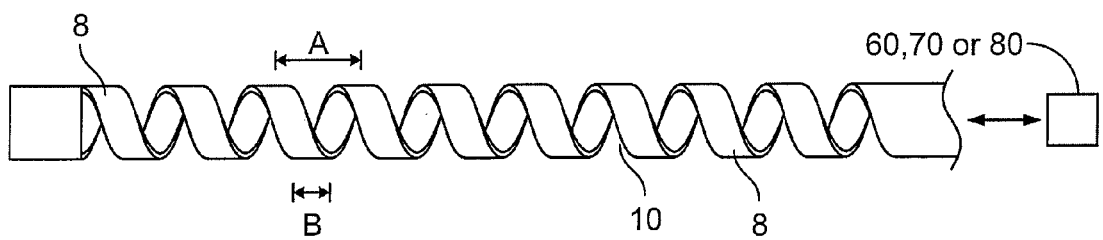
FIGS. 28D and 28E show bottom views of the electrode and covering components of the vacuum coagulation probe variation in FIGS. 28A to 28C.
Figure 28E:
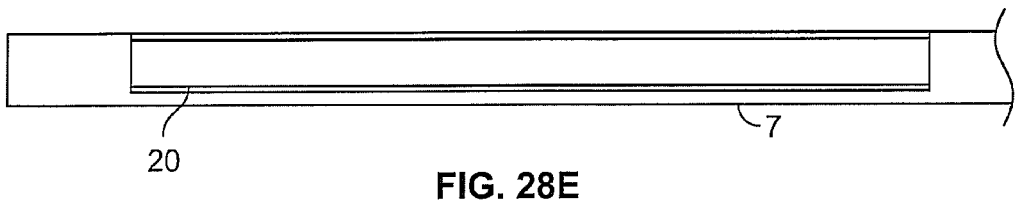
Figure 28B:
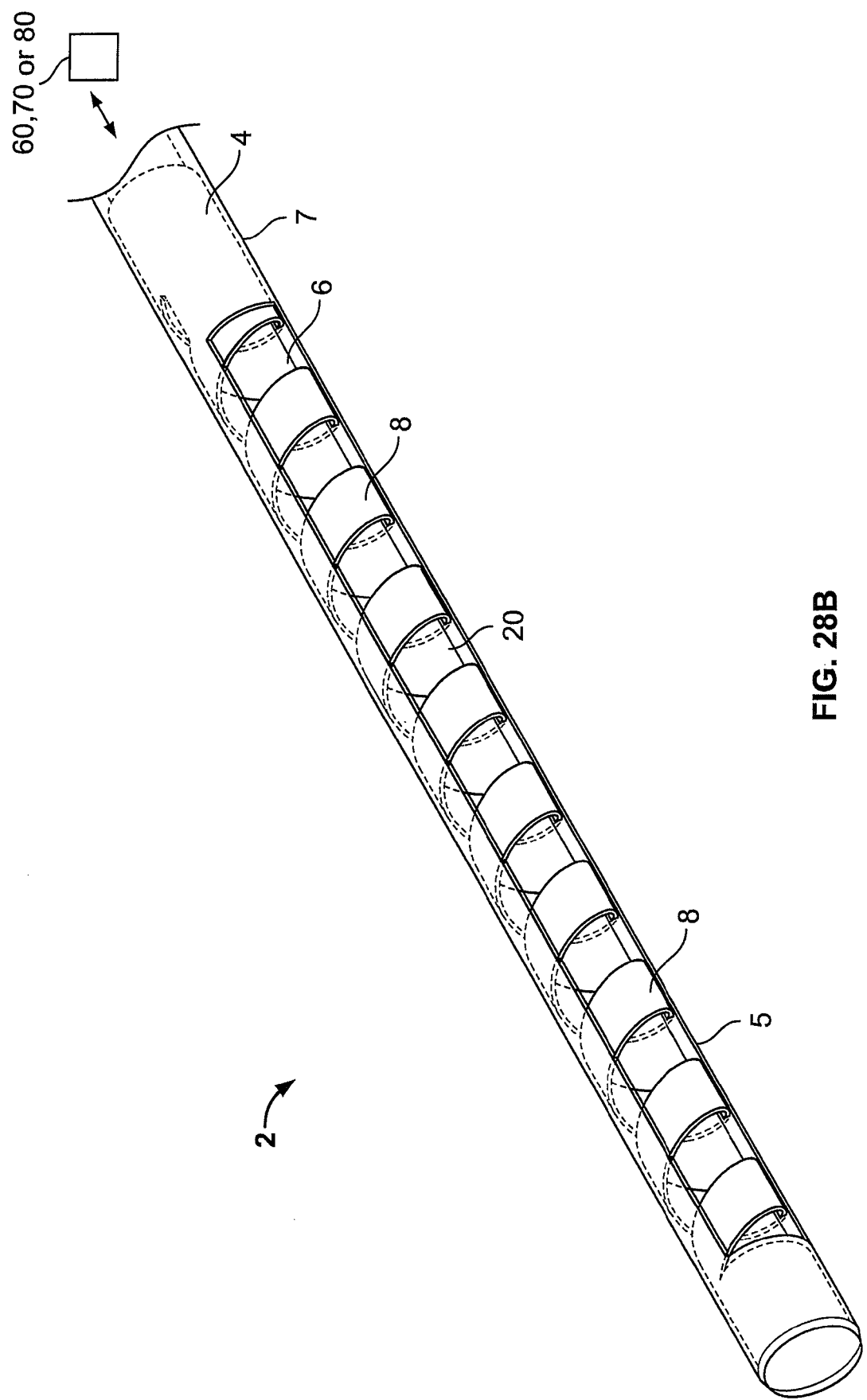

FIGS. 28A to 28C show the distal section 5 of another vacuum coagulation probe 2 variation used to coagulate soft tissue during open surgical and/or minimally invasive access (e.g., thoracoscopic, endoscopic, arthroscopic, laparoscopic, or other approach) into the body cavity. FIGS. 28D and 28E show two components (the electrode/vibrational element 8 and the covering or insulation 7 over the electrode/vibrational element) of the vacuum coagulation probe in FIGS. 28A to 28C. FIG. 28D shows the cut tube that defines conductive windings of the electrode/vibrational element 8 and in this configuration the support of the shaft 4 with a lumen 6 therethrough. FIG. 28E shows the covering/insulation 7 that overlays or covers the cut tube and incorporates an aperture 20 that exposes the electrode/vibrational element 8 and openings 10 between windings of the electrode/vibrational element 8. The covering/insulation extends along the shaft 4 of the probe and terminates at the handle.

The integrated vacuum coagulation probe 2 variation in FIGS. 28A to 28E incorporates a flexible polymer shaft 4 that has a side wall, and covers or encapsulates an electrode/vibrational element 8 fabricated from a cut (laser cut, waterjet cut, chemically etched, etc.) tube (e.g., metal or alloy). The cut tube incorporates an uncut distal tip extending into windings cut into the raw tubing having a pitch (A) and width (B). The pitch (A) is the center-to-center distance between windings. The windings extend a length coincident with the electrode/vibrational element 8 that is defined by exposing the conductive surface of the windings and the openings 10 between windings to tissue by at least one aperture 20 in the side wall of the covering/insulation of the shaft 4. The cut tube may extend further beyond the at least one aperture 20 in the covering that defines the at least one electrode/vibrational element 8 such that the cut tube continues along the entire shaft terminating at the handle attachment point.

Alternatively, the cut tube may be limited to the electrode/vibrational element 8 region and terminate just past the aperture 20 of the covering/insulation 7; this dedicated cut tube electrode/vibrational element 8 is then secured to a separate shaft 4. The inner diameter of the shaft is advantageously greater than or equal to the inner diameter of the electrode/vibrational element region to optimize the suction force applied along the opening and prevent tissue that is pulled into the electrode/vibrational element lumen from lodging in the shaft lumen. In the continuous winding (integral electrode/vibrational element and shaft) configuration, the electrode/vibrational element and shaft sections of the cut tube are covered or encapsulated by an insulative polymer 7 with an aperture 20 in the side wall of the polymer covering to define the electrode/vibrational element 8.

The winding configuration in this configuration may incorporate a single pattern of windings or adjust the pitch, winding width, and/or cut tube geometry from the electrode/vibrational element 8 region to the shaft region. In the separate electrode/vibrational element and shaft configuration, the covering/insulation 7 along the electrode/vibrational element 8 distal section 5 may be integral with the shaft 4 covering/insulation or may comprise separate polymer coverings or insulations secured to the electrode/vibrational element 8 and the shaft 4.

As shown in FIGS. 28A to 28D, the pitch (A) between and the width (B) of individual windings determine the open space (e.g., opening or gap 10) for tissue to be urged into the lumen 6 of the probe and into contact with the conductive windings by the external force of the suction originating from a vacuum source 50. The pitch (A) is at least greater than or equal to 2 times the winding width (B) and is preferably greater than or equal to 3 times the winding width (B) to optimize the efficiency of engaging tissue to the electrode/vibrational element via the suction. In two representative variations, the pitch of the probes were 0.160" and 0.120" respectively, the electrode/vibrational elements 8 winding width were 0.040" for both devices, the widths of the openings between each winding were 0.120" and 0.0080" respectively, and the average length of the electrode/vibrational elements defined by the overall aperture of the covering was 1.5" (range 0.5" to 2.5"). Configured thusly, the probes (when transmitting radiofrequency energy from a RF source 60) were able to consistently create transmural, continuous lesions in soft tissue spanning the length of the electrode/vibrational element and having a depth greater than the width of the opening. In addition, no hot spots were observed and the lesions demonstrated consistent tissue damage throughout the lengths. These results were dramatically different to non-suction based approaches that observe hot spots in regions of intimate contact and shallow lesions in regions of lesser tissue contact.

FIGS. 29A and 29B show an alternative cut tube variation that, along with the covering/insulation and corresponding aperture(s) 20 therethrough (as described above and shown in FIG. 28E) that expose the conductive windings of the cut tube comprising the electrode/vibrational element 8 of the probe. If the windings of the cut tube further extend axially beyond the aperture 20 of the covering, then the cut tube may also comprise a portion or the entirety of the shaft 4 of the probe 2. This electrode/vibrational element 8 variation comprises multiple windings that emanate from an axially extending backbone 36. The windings have at least one pitch (A) and at least one width (B), as shown in FIGS. 29A and 29B.

FIGS. 29C and 29D show an alternative variation where windings extend from a backbone and define openings between individual windings wherein the windings define the conductive element of the electrode. The backbones 36 in these variations assist in maintaining the shape of the deformed electrode/vibrational element 8 when pre-shaped to compliment, interface with or relatively match the soft tissue contours to be treated and provide stiffness to the probe during placement and positioning of the electrode/vibrational element 8 against the soft tissue surface. The backbone 36 alternatively provides increased column strength to improve the micro-motion caused by axial or radial displacement of the vibrational element 8 via the drive shaft coupled to a linear motor or rotary motor 70 when using mechanically-induced ultrasonic ablation.

Furthermore, is noted that alternative cutout tube geometries may be used for the electrode/vibrational element(s). Any geometry may suffice so long as it defines windings (e.g., individual segments of electrode/vibrational element) extending from the probe axis between 0 and 90 degrees that include openings 10 through which, in cooperation with the aperture(s) 20 incorporated in the insulative covering 4, vacuum can be applied to force soft tissue between the openings 10 and into direct engagement with the exposed windings.

Figure 30A:
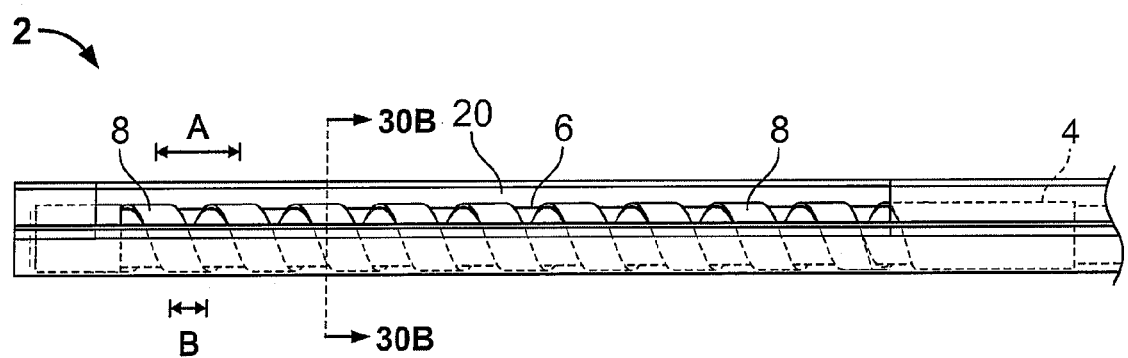
FIGS. 30A to 30B show a perspective view, a bottom view, a side view, and a cross-sectional view of an integrated vacuum coagulation probe variation that incorporates an offset between the active electrode and the surface of the probe, and multiple lumens for injection of cooling or therapeutic media.
Figure 30B:
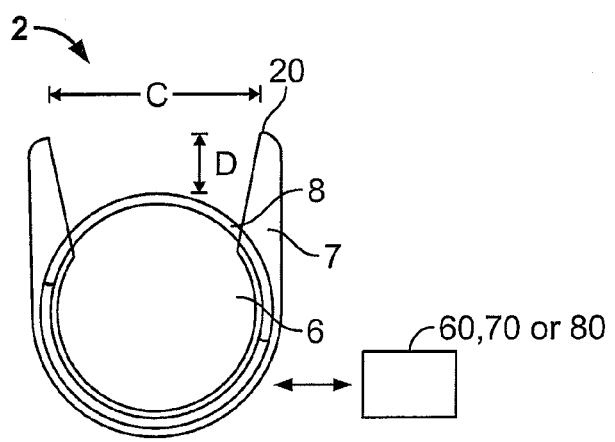

FIGS. 30A and 30B show the distal section 5 of another integrated vacuum coagulation probe 2 variation. This probe 2 incorporates at least one electrode/vibrational element 8 fabricated as a series of windings (in a helix as shown, a backbone with associated windings/ribs, a mesh, or other configuration) from a cut tube or wound wire having at least one pitch or winding center-to-center separation (A) and at least one winding width (B). The cut tube defines a vacuum lumen 6 for providing a suction path from a vacuum source 60 coupled to the handle. A polymer covering/insulation 7 is extruded, injection molded, or dipped over the cut tube to preserve the lumen 6 and provide at least one aperture 20 that exposes the at least one opening 10 between individual electrode/vibrational element 8 windings and the conductive surface of segments of individual electrode/vibrational element windings (as shown in FIG. 30B as a blackened section of the conductive windings). The proximal region of the polymer covered cut tube defines the shaft 4. As shown in FIG. 30B, the tissue contacting surface of the covering/insulation along the opening 10 is offset from the electrode/vibrational element 8 by a distance (D). The openings 10 also comprise at least one width (C) into which soft tissue is directly urged into engagement with the at least one electrode/vibrational element 8 via suction.

The ratio between the offset (D) and the width (C) produces a coagulation response dependent on the application. For integrated, direct soft tissue coagulation, such as required during atrial fibrillation ablation or tendon shrinkage, C>2D to maximizes the contact between uneven or creased soft tissue surfaces and the exposed surface of the electrode/vibrational element winding(s). However, D is preferably >0 for all variations (e.g., the covering/insulation extends beyond the at least one electrode/vibrational element) to enhance the suction response of the vacuum coagulation probe.

By incorporating an offset D using the flexible polymer covering/insulator 7, the ability for the vacuum-integrated coagulation probe 2 to contact soft tissue and produce a vacuum seal required to engage the soft tissue and bring it into engagement with the at least one electrode/vibrational element 8 is dramatically improved. This is especially important in applications where the soft tissue surface is creased or uneven. The flexible covering/insulation 7 forms an extension about the at least one aperture 20 that fills the creases or uneven anomalies thereby preserving the suction force of the soft tissue to the vacuum-integrated coagulation probe 2 and ensuring the entire length of soft tissue engages the at least one electrode/vibrational element 8.

In addition, this offset D also has the ability to lift the tissue layer separating it from underlying tissue layers. For example, during tendon shrinking applications of the shoulder, the tendon is engaged against the at least one electrode/vibrational element 8 via the suction and is lifted from underlying nerves, or blood vessels thereby directly heating the tendon tissue while preserving the integrity and functionality of the underlying nerves and blood vessels. This feature is also important during atrial fibrillation treatment where underlying vessels such as the circumflex artery, the right coronary artery, and the coronary sinus reside in the interatrial groove. When coagulating tissue completely to the valve annulus to use the annulus as a barrier to electrical wavelet propagation, soft tissue along the interatrial groove is coagulated. By lifting the atrial tissue along the interatrial groove and cooling underlying tissue layers, the atrium is coagulated up to the interatrial groove yet the underlying blood vessels, if any, are preserved.

For applications where the target tissue that the medical practitioner wants to heat resides between a definite soft tissue surface that needs to be preserved and the at least one electrode/vibrational element 8, a greater offset (D) is incorporated into the vacuum coagulation probe. Even so, C>D. This configuration addresses articular cartilage removal where jagged cartilage above the bony surface is heated and removed via the vacuum without thermally damaging the underlying bony surface. The integrated electrode/vibrational element 8 and vacuum transmission of the vacuum coagulation probe variations of the invention enable directly heating the target tissue by pulling the target tissue into engagement with the edges of the electrode/vibrational element 8. The fluid perfusion mechanism enables cooling underlying tissue that is offset from the electrode/vibrational element 8 to preserve that soft tissue layer while evoking the desired effect on the contacted tissue layer.

As described above, the multilumen vacuum-integrated coagulation probe incorporates a distal tip opening 40 through which a suture, umbilical tape, or flexible tube can be tied to apply tension against the distal end of the probe. In addition, a perfusion channel 100 integral to the multilumen covering 7 allows passage of fluid from a fluid source 55 past the outlet 26 between the perfusion lumen 16 and the vacuum lumen 6 to hydrate and cool soft tissue directly contacting the electrode/vibrational element 8 and improve the transmission of energy to create deeper lesions required to ensure continuous, transmural lesions. As previously stated, a separate injector is not required to force fluid through the perfusion lumen since the normally open perfusion passage is blocked only when a vacuum source 50 applies suction to the vacuum lumen 6 and forces soft tissue into engagement with the electrode/vibrational element 8 along the aperture(s) 20 through the covering 7; in that situation, the suction force pulls the fluid from the fluid source 55, along the perfusion lumen 16, past the outlet 26, and along the vacuum lumen 6.

As previously discussed, the electrode(s)/vibrational element(s) 8 at the distal section 5 of the probe 2 will be routed to a signal generator 60 via signal wires positioned within the shaft 4 (for transmission of radio frequency energy to at least one electrode), or to a linear motor 70 or a rotary motor 80 via at least one drive shaft located within the shaft 4 (for mechanically-induced generation of ultrasonic energy).

These integrated, multilumen vacuum-integrated coagulation probe variations enable directly heating unwanted tissue superficial to healthy tissue that needs to be preserved (e.g., articular cartilage removal without damaging the underlying bone cells). The offset D of electrode 8 from the soft tissue surface and the passive injection of cooling fluid provides a buffer from which only tissue urged into contact via the suction is heated and removed without conducting heat deeply into the underlying tissue. As such articular cartilage may be heated and removed while preserving the bony cells.

In this and other applications, the multilumen vacuum probe may perfuse therapeutic, pharmacologic solutions (e.g., gludaraldehyde, other cross-linking agents, hydrochloride, ethanol, heparin, rapamycin, paclitaxel, or other drug) from a fluid source 55 through the fluid perfusion lumen 16 and along tissue pulled into direct contact with the probe 2 at aperture 20 via the vacuum. As such, toxic yet potentially therapeutic substances such as gludaraldehyde, etc. may be used to invoke a tissue response while being quickly removed to avoid adversely affecting adjacent anatomy. As such the vacuum probe may cause tissue shrinkage by engaging tendons, or other soft tissue with a therapeutic cross-linking agent that is removed after exposing only a specific region of tissue. Alternatively, drug solutions may be locally transmitted to specific tissue regions to kill cells, alter cellular structure, prevent a biological reaction, or other purpose. The isolated injection of therapeutic solutions may be augmented by the delivery of radiofrequency or direct current energy (continuous or pulses) or mechanically-induced ultrasonic energy to cause electroporation or other tissue response to augment the impact of the therapeutic solution injection.

The variations described above may be treated so they are malleable and may be deformed into a desired shape required to access the desired coagulation location and/or create the desired lesion length, and shape. An alternative approach to position the probe at the target anatomic location is to incorporate a steering mechanism in the vacuum coagulation probe. The steering mechanism may be used to deflect the entire electrode/vibrational element relative to the shaft and/or a portion of the electrode/vibrational element. At least one pull-wire can be secured to the electrode/vibrational element at the electrode/vibrational element to shaft junction if the electrode/vibrational element is to be deflected as a unit relative to the shaft, or along the electrode/vibrational element up to the distal end of the probe if the electrode/vibrational element is to be deflected. The opposite end of the pull-wire(s) may then be routed to the handle and secured to an actuation knob (not shown) to manually deflect the vacuum coagulation probe into a curve. The curve shape, angle and radius is defined by the distance along or from the electrode(s)/vibrational element(s) at which the pull-wire(s) is/are secured and the stiffness relationship between the shaft and the electrode(s)/vibrational element(s). A guide-coil or other radially restraining component can be housed around the pull-wire(s) in the shaft to specify the stiffness of the shaft and further define the radius of curvature and angle of deflection of the distal region of the probe as the pull-wires are actuated.

Existing atrial fibrillation coagulation or other soft tissue coagulation treatment applications performed thoracoscopically, endoscopically, arthroscopically, laparoscopically, or with other less invasive approach tend to create incomplete curvilinear lesions because the desired lesion sites are inaccessible, contact to the tissue is poor, and/or the temperature gradient from the contacted tissue surface to the opposite tissue surface is dramatic. These conditions limit the creation of continuous, transmural, curvilinear, lesions. Such limitation is especially the case when blood is flowing along the opposite tissue surface producing a heat sink that cools that tissue surface further affecting the temperature gradient and limiting the lesion depth. As such, the existing techniques can be inferior and have a higher rate of arrhythmia persistence than the vacuum coagulation probe devices of the invention.

In addition, incomplete lesion creation during atrial fibrillation treatment has been demonstrated to generate substrates for persistent atrial flutter and/or atrial tachycardia. For some other applications, the inability to create consistent and complete lesions allows cancerous cells, or other disease substrates to prevail. For applications such as tendon shrinkage or articular cartilage removal, the inability to direct coagulation to a specific region of tissue without affecting underlying layers of tissue indiscriminately damages tissue structures (e.g., nerves, blood vessels, bone cells, or other untargeted tissue) that need to be preserved. The same concern holds true for atrial fibrillation ablation in which lesions extend to the interatrial groove where the circumflex, right coronary artery and coronary sinus reside near the valve annulus and must be preserved. The variations of the invention mitigate these risks by engaging isolated, target tissue regions and enabling direct coagulation of a specific region of tissue without damaging unwanted tissue' structures.

Rail Mechanisms for Manipulating Vacuum-Integrated Coagulation Probes

Figure 8A:
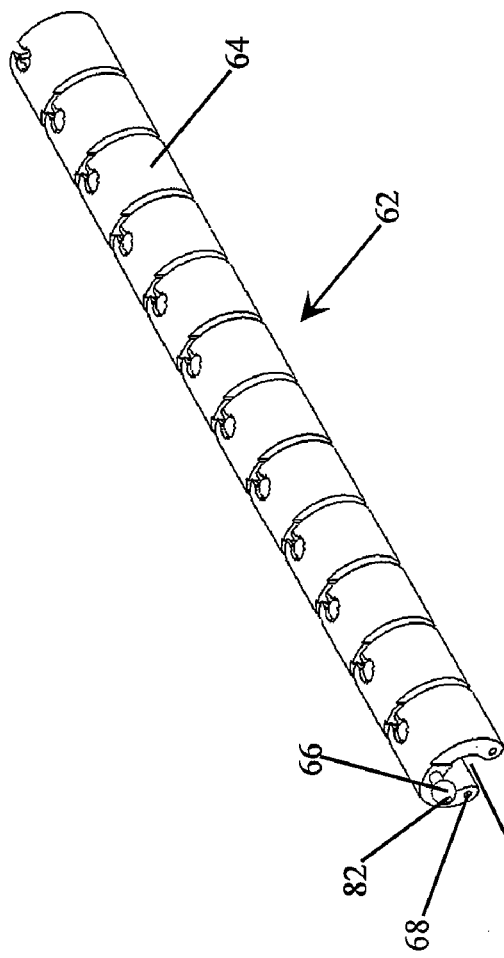
FIGS. 8A to 8C shows an isometric view, a side view, and an end view of a modular, lockable, external rail mechanism that is able to lock and maneuver the vacuum-integrated coagulation probe along a directed path.
Figure 8B:
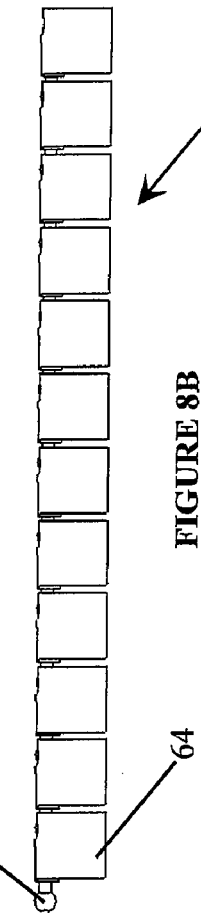
Figure 8C:
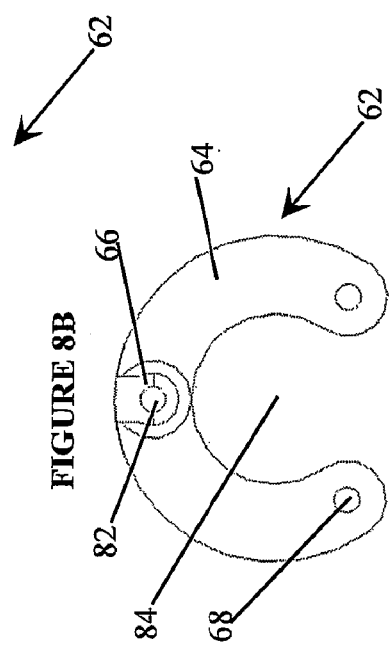

Remote access may be important for placing the vacuum-integrated coagulation probe at the desired locations along the heart surface (epicardial or endocardial) to ensure therapeutic lesion sets are created. FIGS. 8A to 8C show an isometric view, a side view, and an end view of a rail mechanism 62 that directs the vacuum-integrated coagulation probe variations along a defined path without the need for steering mechanisms or stylets inserted through the perfusion channel, described above. As such, the flexibility of the vacuum-integrated coagulation probe can be preserved and the rail mechanism 62 can address all access requirements for the probe. As shown in FIGS. 8A to 8C, individual rail components 64 pivot relative to each other by sequential ball 66 and socket joints that permit rotation in 3-dimensions of individual rail components 64 to each other. The ball 66 and socket joints incorporate a central lumen 82 through which a flexible rod can reside. A nut incorporated at the handle end (not shown) of the rail mechanism 62 can be coupled to the flexible rod and tightened to further engage the individual ball features 66 of the rail components 64 against the mating sockets to lock the rail mechanism in the shape the rail mechanism was manipulated at the time the nut was used to tighten the rail components along the flexible rod. Two pull-wires are inserted along the lateral channels 68 of individual rail components to help manipulate (e.g., steer) the rail components by actuating the two pull-wires relative to each other and relative to the flexible rod to maneuver the rail mechanism into various 3-dimensional shapes. Once the pull-wires are used to position the rail mechanism 62, the rail components 64 are tightened along the flexible rod to maintain the desired shape. After positioning and locking the rail mechanism 62, the vacuum-integrated coagulation probe 2 can be advanced along the rail lumen 84 of the rail mechanism 62, as shown in FIGS. 9A to 9D.

As shown in FIG. 9D, the perfusion channel/tube 10 outer profile along the distal section 5 of the probe matches the inner shape of the rail mechanism and locks within the rail components 64 lumens 84 so the rail mechanism 62 maintains the position of the probe 2 distal section 5 while allowing the probe to be advanced along the rail mechanism. Once the vacuum-integrated coagulation probe 2 is advanced into position along the rail mechanism 62, the rail mechanism can be further manipulated (e.g., steered) and locked into a new position thereby repositioning the distal end of the vacuum-integrated coagulation probe. Further, it should be noted that the lumen 84 of the rail mechanism 62 can be configured to match another cross-sectional segment of the vacuum-integrated coagulation probe 2 including the entire cross-section to lock the probe to the rail mechanism while preserving the ability to advance and retract the probe relative to the rail mechanism.

FIG. 10 shows an alternative rail mechanism 62 that comprises a unitary tubular structure that incorporates an opening along one side of the tubular structure and defines a lumen 84. The opening and lumen geometries ensure the perfusion channel/tube or the entire distal section 5 cross-section of the vacuum-integrated coagulation probe 2 to lock the probe 2 within the rail mechanism 62 but preserves the ability to readily advance and retract the vacuum-integrated coagulation probe along the rail mechanism.

The rail mechanisms described above can support dissecting/tunneling tools (described below) and/or endoscopic optics/cameras to facilitate positioning the rail mechanism at the desired location around the heart or other anatomic structure. As described below, a dissecting/tunneling mechanism can pass along the lumen of the rail mechanism to facilitate placement of the rail mechanism as fat tissue is dissected and the dissecting/tunneling tool is positioned at the desired location. The rail mechanism can also house an endoscopic camera (through the lumen 84 of the rail mechanism 62, the ball and socket lumen 82, or another lumen 68 incorporated in the individual rail components 64) to directly visualize placement of the rail mechanism, dissecting/tunneling, or coagulation processes. In addition, the flexible rod and/or pull-wires can comprise fiberoptics to incorporate a light source to assist visualization of tissue approximate the distal end of the rail mechanism.

Atrial Fibrillation Treatment Using Vacuum-integrated Coagulation Probes

An approach for treating atrial fibrillation with the vacuum-integrated coagulation probe of the invention is described. In one method, the probe is inserted into the thoracic cavity through incisions, trocars, or other access aperture placed in intercostal spaces, a thoracotomy, a thoracostomy, a median sternotomy, a mini-sternotomy, a subxyphoid access port, a lateral subthoracic access site, or other less invasive surgical procedure. As such, the distal section and shaft of the probe have low profiles to facilitate advancing through small cavities associated with limited access applications.

FIGS. 11A, 11B, and 11D show an isometric view, a side view, and a top view of a trocar assembly 104 variation that incorporates an elliptical or oval cross-section and a locking feature that engages the interior surface of the chest once inserted into the thoracic cavity. FIG. 11C shows the dilator component 112 of the trocar assembly that is positioned into the trocar sheath 106 during insertion through the chest wall. The dilator component 112 incorporates notches 117 through which the movable locking legs 114 of the trocar sheath (FIG. 11E) can rotate. During insertion, as shown in FIGS. 11A, 11B, and 11D, the dilator component 112 (FIG. 11C) resides through the lumen 119 of the trocar sheath 106 (FIG. 11E) and the locking legs 114 of the trocar are closed to provide a smooth transition from the pointed tip 116 of the dilator component 112, along the tapered distal section 115 of the trocar, and along the outer surface of the trocar sheath 106.

Once the trocar assembly 104 has been inserted through the skin and past the chest wall such that the distal end of the trocar sheath resides inside the thoracic cavity, the locking legs 114 are rotated relative to the trocar sheath 106 releasing the dilator component 112 from the trocar sheath 106 and preventing retraction of the trocar sheath 106 from the chest. FIGS. 12A to 12C show an isometric view, a side view, and a top view of the deployed trocar sheath 106 with the locking legs rotated into a locking position such that they engage the interior surface of the chest wall. As shown in FIGS. 11E and 12C, the cross-section of the trocar sheath 106 is elliptical or oval having a lumen 119 length (L) at least three times the lumen width (W). The lumen 119 width (W) ranges from 2 mm to 12 mm and the lumen length (L) ranges from 6 mm to 60 mm. Alternatively, the cross-section may be rectangular or substantially rectangular with radiused corners as long as the lumen 119 length (L) is at least three times the lumen 119 width (W). The elongated cross-sectional geometry of the trocar sheath 106 supports the opening through the chest wall to allow passage of the vacuum coagulation probe or other instruments and facilitates manipulation of the device since rotation along the length (L) of the trocar sheath 106 lumen 119 increases the range of movement of the device within the trocar sheath 106 without applying excess pressure on the chest wall. The trocar sheath will be fabricated from a polymer (e.g., polycarbonate, PTFE, polyimide, polyurethane, other polymer, or braided tubing having the desires cross-section and geometry) that supports the opening to the chest wall and will not deform easily while the device is manipulated within the trocar sheath lumen.

Once inserted into the thoracic cavity (e.g., through the elongated cross-section trocar), the probe may be deflected or deformed into the desired lesion pattern, comprising slight curves passing along the surface of the heart, for example between the left pulmonary vein and right pulmonary vein. As described above, the vacuum-integrated coagulation probe may incorporate steering or preshaped stylets to manipulate the position within the thoracic cavity. Alternatively, a rail mechanism, as shown in FIGS. 8A to 8C, 9A to 9D, and 10 and described above, may be positioned at the target lesion location and used to lock and advance the probe into position along the rail mechanism. Once placed, the vacuum source is actuated to apply a suction force through the vacuum opening(s) of the electrode(s)/vibration element(s) and through the covering aperture to urge the epicardium of the left atrium 36 into intimate contact with the electrode(s)/vibrational element 8. It should be noted that the vacuum-integrated coagulation probe can instead be placed against the endocardium of the atria during cardiopulmonary bypass procedures where the atria are open for valve (mitral, tricuspid, and/or atrioventricular) repair or replacement procedures or beating heart procedures where an introducer into the atrium is obtained through an atrial appendage, the atrial free wall, the ventricle, a pulmonary vein, a vena cava, or other conduit that may be closed upon completion of the coagulation procedure.

Given the flexibility for application of the subject devices, any pattern of curvilinear, transmural lesions may be created along the epicardial surface or the endocardial surface with the vacuum coagulation probe variations of the invention. One left atrial lesion pattern involves creating a "C" that passes from the mitral valve annulus adjacent the left atrial appendage (where the great vein and the circumflex do not parallel the atrioventricular annulus but have curved towards the apex of the left ventricle) above the superior pulmonary vein and back towards the mitral valve annulus adjacent the right pulmonary veins; or below the inferior pulmonary veins and towards the anterior mitral valve annulus. Another left atrial lesion pattern involves creating a "V" where the intersection resides at the mitral valve annulus adjacent to the left atrial appendage and each segment passes on opposite sides of the pulmonary veins and ends adjacent to the interatrial septum. A stretched "B" with each curved segment extending around either the left pulmonary veins or the right pulmonary veins and the central links separated by a distance wherein the top line of the "B" connects to the mitral valve annulus adjacent the left atrial appendage. A stretched "S", reverse "S", or figure eight with the initiating point occurring at the mitral valve annulus adjacent to the left atrial appendage and curving from that base point to encompass the left and right pulmonary veins as pairs within the curved segments. In addition to the various left atrial lesion patterns above, right atrial lesions may be created along the cristae terminalis, from the inferior vena cava to the superior vena cava, from the cristae terminalis to the tricuspic annulus, from the superior vena cava to the tricuspid annulus, or other geometry capable of preventing atrial flutter along the right atrium. Alternative potential lesion patterns capable of treating atrial fibrillation, which the vacuum coagulation probe may replicate, are described in U.S. Pat. No. 6,071,279 entitled "Branched structures for supporting multiple electrode elements" and incorporated herein by reference.

Advantageously, the entire length of the exposed electrode(s)/vibrational element is used to apply suction through the at least one opening 10 to apply a vacuum force against the epicardium (or endocardium) and urge the tissue into engagement with the electrode(s)/vibrational element. For electrical heating of soft tissue, radiofrequency (or D.C.) energy is transmitted to tissue heating electrode(s) in unipolar or bipolar mode such that the current density is transmitted into tissue adjacent the at least one electrode and ohmic heating causes the tissue adjacent the at least one electrode to heat and conduct the heat further into depths of tissue. Alternatively, the electrode(s) may be fabricated from a resistive element (e.g., tantalum, tungsten, Nichrome, etc.) in which radiofrequency (or D.C.) energy applied along the resistive element, between wire connections at opposite ends of the resistive element, heats the element and the intimate tissue to electrode(s) contact enables thermal conduction of the heat from the electrode into the target soft tissue.

Alternatively for mechanically-induced ultrasonic heating, a drive shaft is secured to the vibrational element(s) and a linear or rotary motor is used to cycle the displacement (linear or angular) of the vibrational element(s) at a high frequency and small displacement (linear or angular). As such, a mechanically-induced ultrasonic wave is transmitted from the vibrational element(s) into soft tissue directly contacting the vibrational element(s) or coupled to the vibrational element(s) via a fluid path. The mechanically-induced ultrasonic wave causes cavitation which imparts heating of the soft tissue above a threshold where the soft tissue becomes electrically non-viable but structurally strong.

The transmission of radiofrequency energy in unipolar or bipolar mode, or of mechanically-induced ultrasonic energy causes the soft tissue to heat which conducts further into adjacent soft tissue; alternatively the heating of a resistive element causes the resistive electrode(s) to heat which is then conducted into adjacent, contacted soft tissue. As cardiac cells (and any muscle tissue) are heated above 50° C., irreversible conduction block occurs and the cells become non-viable (Nath, et al. Cellular electrophysiologic effects of hyperthermia, on isolated, guinea pig papillary muscle: implications for catheter ablation. Circulation. 1993; 88:1826-1831). As such, a consistent, continuous length of atrial tissue extending from the epicardial surface to the endocardial surface must be heated above 50° C. to treat atrial fibrillation.

Additional Applications Utilizing the Vacuum-Integrated Coagulation Probes

For other applications involving coagulation of soft tissue to shrink collagen rich tissues or prevent shrinking of collagen tissues, heating of the soft tissue must be controlled which the vacuum coagulation probe variations of the invention enable. Published studies evaluating the response of vessels (arteries and veins) to heat have focused on the ability to permanently occlude vessels. Veins have been shown to shrink to a fraction of their baseline diameter, up to and including complete occlusion, at temperatures greater than 70° C. for 16 seconds; the contraction of arteries was significantly less than that of veins but arteries still contracted to approximately one half of their baseline diameter when exposed to 90° C. for 16 seconds (Gorisch et al. Heat-induced contraction of blood vessels. *Lasers in Surgery and Medicine.* 2:1-13, 1982; Cragg et al. Endovascular diathermic vessel occlusion. *Radiology.* 144:303-308, 1982). Gorisch et al explained the observed vessel shrinkage response "as a radial compression of the vessel lumen due to a thermal shrinkage of circumferentially arranged collagen fiber bundles". These collagen fibrils were observed to denature, thus shrink, in response to heat causing the collagen fibrils to lose the cross-striation patterns and swell into an amorphous mass.

Variations of the invention prevent or limit the heat-induced contraction of such structures as the pulmonary veins by applying a vacuum force capable of maintaining the position (e.g., diameter) of the vessel while heating the soft tissue. As such, the vessel is stented or supported from the external surface as the tissue is heated above the required 50° C. threshold without concern that the vessel may accidentally become stenosed due to the heat-induced contraction.

Alternatively, the vacuum coagulation probe variations direct heat-induced contraction of such structures as tendons, ligaments, skin or other anatomy in which the therapy is designed to heat thereby denature the collagen and shrink the tissue until the desired shape or effect is achieved. In addition, the vacuum coagulation probe can reposition the soft tissue while heat is applied to the soft tissue to direct the shrinking and cause the collagen fibrils to reorganize reforming the soft tissue into a desired shape.

The integrated vacuum coagulation probe variations above can also be utilized in shrinking tendons, ligaments, or otherwise modifying such collagen-based tissue structures either by locally heating the target tissue layer as described above or transporting cross-linking agents (e.g., gludaraldehyde) or other pharmacological substances specifically to the region of soft tissue engaged against the opening(s) 10 of the probe. As such these typically toxic materials are also removed after invoking their desired tissue response. Cross-linking agents have been demonstrated to cause collagen-induced shrinking of tissue structures and increase the strength of such structures; therefore, they are highly suited, despite their toxicity, to strengthening and shrinking damaged tendons. As such these integrated vacuum coagulation probe variations enable treated the tissue with such agents without concern for their toxicity since they are immediately removed by the vacuum.

The integrated vacuum coagulation probe variations of the invention also enables treating a tissue surface without damaging underlying tissue structures (e.g., nerves or vascular tissue) by slightly lifting the target tissue surface away from the underlying layers via the vacuum while coagulating the target tissue layer. As such, the underlying tissue is preserved.

Theranostic Probe Variations

The term "theranostic" refers to the ability to determine the outcomes of a therapeutic procedure by using diagnostic devices and methods. In the variations described below, theranostic devices refer to intraoperative diagnostic devices that determine whether a therapeutic minimally invasive surgical procedure has been effective at accomplishing its task.

The vacuum-integrated coagulation probes described above and shown in FIGS. 1A to 1C, 2A to 2E, 3, 4A to 4C, 5A and 5B, 6A to 6F, and 7A to 7I may be used as theranostic probes. In adapting those vacuum-integrated coagulation probes to theranostic devices, a stimulator/pacemaker is connected to the electrical connections 14 at the handle of the theranostic probe. The stimulator delivers, pacing pulses to the electrode(s) 8 that is/are held into engagement with the soft tissue surface (e.g., pulmonary vein, atrial wall, or ventricular wall) via the vacuum-integrated features to stimulate electrical propagation throughout the atria or ventricles and determine if the therapeutic procedure achieved the desired results.

These adapted theranostic probe variations do not require perfusion tubes, as shown in some of the vacuum-integrated coagulation device variations, but would require at least one electrode that defines openings and a covering that incorporates an aperture to expose the openings and the electrode windings. The vacuum source is coupled to the vacuum lumen and the openings between the electrode windings such that upon activation of the vacuum source, soft tissue is pulled into direct engagement with the electrode(s) 8 whereby manual pressure is not required to maintain the device into contact with the soft tissue surface. Once the electrode is urged into engagement with soft tissue, pacing pulses are transmitted into soft tissue to stimulate the soft tissue and determine conduction characteristics and/or determine whether an arrhythmia substrate is inducible. By stimulating one region of tissue (e.g., near or on the pulmonary veins)

conduction to the atrial wall can be evaluated to determined whether adequate conduction block or pathways have been created. To induce an arrhythmia, various programmed stimulation protocols can be utilized to determine the ability to initiate an arrhythmia. Alternatively, rapid pacing involving transmitting pacing pulses at a rate faster than sinus rhythm may be utilized to determine whether the arrhythmia can be initiated. Those same electrodes may also be used to transmit electrical signals produced by the soft tissue to a mapping system or signal acquiring instrument capable of conditioning, displaying, and/or recording the electrogram signals.

FIGS. 13A to 13C and 14 show two alternative theranostic probe 120 variations. In each of these variations, the electrode comprises two conductive segments 128 or 138 separated and bonded with an insulative layer to provide transmission of pacing stimuli in bipolar fashion between the discrete, separate conductive segments without the need for a large reference ground pad. The conductive segments 128 or 138 define at least one opening 10 through which the vacuum lumen is coupled. A covering 15 defines an aperture 20 that exposes the conductive segments 128 or 138 of the electrode and the opening(s) 10. The distal segment is connected to a shaft 4 that is routed to a handle 102. A vacuum control knob 54 determines when vacuum is being applied by the vacuum source 50. The electrodes conductive segments 128 or 138 are routed to a stimulator 90 with signal wires contained within the shaft 4 and attached to a connector in the handle to which the stimulator 90 can be connected.

Figure 15B:
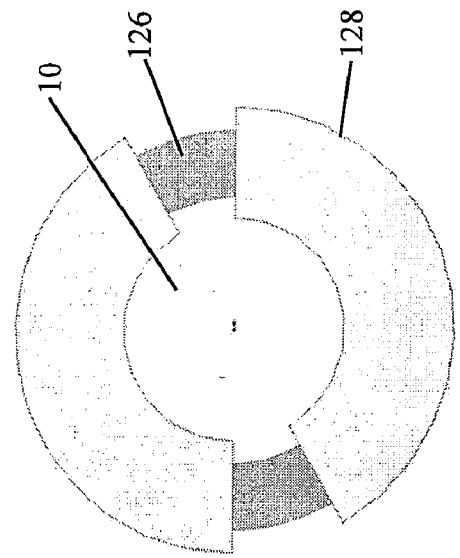
FIGS. 15A and 15B show an isometric view and an end view of the integrated electrode of the theranostic probe in FIGS. 13A to 13C.
Figure 15A:
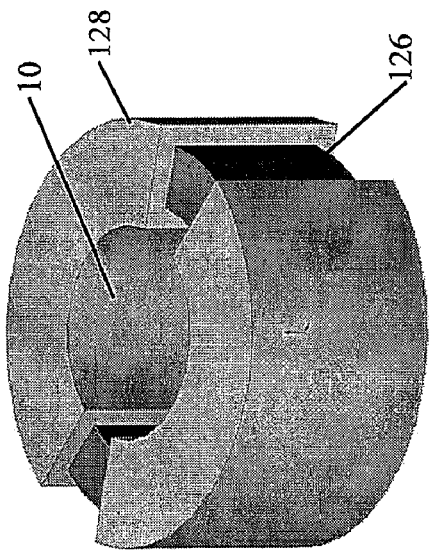

FIGS. 15A and 15B show an isometric view and an end view of the electrode assembly for the theranostic probe variation in FIGS. 13A to 13C. In this electrode assembly, two conductive segments 128 that each extend less than 180 degrees are attached together with insulative adhesives or mechanical insulative structures 126 such that they face each other to define an opening 10 but are electrically insulated from each other. Each conductive segment 128 is connected to a separate wire, each of which is routed to a connector, which is coupled to the stimulator.

Figure 16B:
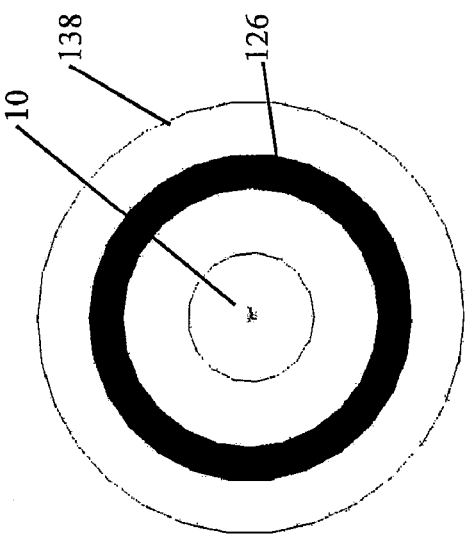
FIGS. 16A and 16B show an isometric view and an end view of the integrated electrode of the theranostic probe in FIG. 14.
Figure 16A:
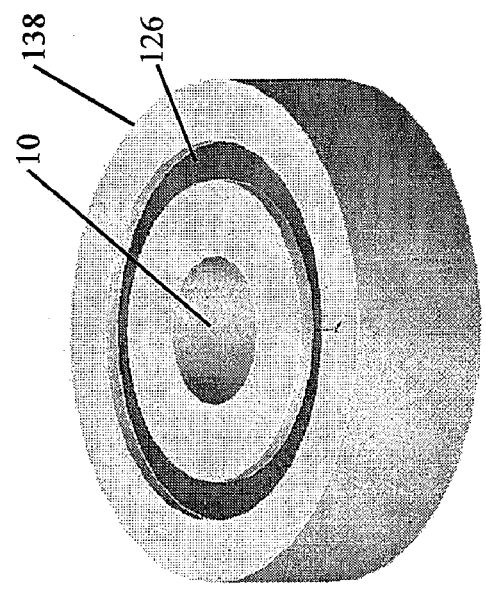

FIGS. 16A and 16B show the electrode subassembly for the theranostic probe variation in FIG. 14. This electrode subassembly incorporates two ring conductive segments 138 having different diameters such that one fits within the other and is separated by a electrically insulative adhesive or structure 126, again to ensure mechanical stability that defines a central opening 10 and electrical insulation of the discrete conductive segments. The electrode subassemblies are housed in a flared covering 15 that defines an aperture 20, as shown in FIGS. 13A to 13C and 14. Each electrode subassembly includes a central opening 10 through which the vacuum lumen is coupled in order to pull soft tissue into direct engagement with the electrode while transmitting pacing stimuli. An elongated, flexible shaft connects the electrode subassembly to the handle and preserves the vacuum lumen to ensure the electrode subassembly engages soft tissue without manually pushing the probe against the tissue surface, which could cause damage to the tissue surface or perforation of the tissue structure. The electrodes are connected to a stimulator/pacemaker 90 via an electrical connector housed in the handle 102 of the device.

FIGS. 17A to 17E show an isometric view, a front view, a side view, a bottom view, and a sectional view of an alternative theranostic probe 120 variation. This theranostic probe variation incorporates discrete ring electrodes 18 that are separate from each other to define at least one opening 10 and are individually insulated 38 to ensure signals received by each electrode 18 are individually transmitted through dedicated signal wires, contained within the shaft 4, to an electrophysiology recorder, electrogram mapping system, or other device capable of acquiring, conditioning, displaying, and/or recording biological signals.

Similarly, pacing stimuli may be transmitted from a pacemaker/stimulator, along individual signal wires, through individual electrode rings 18, and into contacting soft tissue in monopolar mode (between a discrete ring electrode and a large surface area ground pad) or bipolar mode (between individual electrodes). An insulative covering 7 is located along the distal section 5 of the probe to define at least one aperture 20 the exposes the electrodes 18 and the opening(s) 10 between discrete electrodes. Since this configuration orients the distal section 5 perpendicular to the shaft 4 axis (as opposed to previous configurations that were oriented axially), the covering 7 in the distal section 5 defines a conduit 28 that couples the vacuum lumen 6 to the opening(s) 10 and the aperture 20. The covering also contains external ribs 30 that aid in maintaining the aperture 20 side-separation as the distal section 5 is manipulated into a curved shape.

Dissecting/Tunneling Variations

FIGS. 18A to 18C, 19A to 19H, 20A to 20D, and 21A to 21C show dissecting/tunneling tool 124 variations of the invention that are designed to remove or separate adipose tissue (e.g., fat) and/or interconnective tissue from the heart. The purpose of such action is to expose muscle layers and permit maneuvering the vacuum-integrated coagulation probe into engagement with heart tissue at any location, whether or not previously covered by fat or interconnective tissue.

Figures 18A, 18B, 18C:
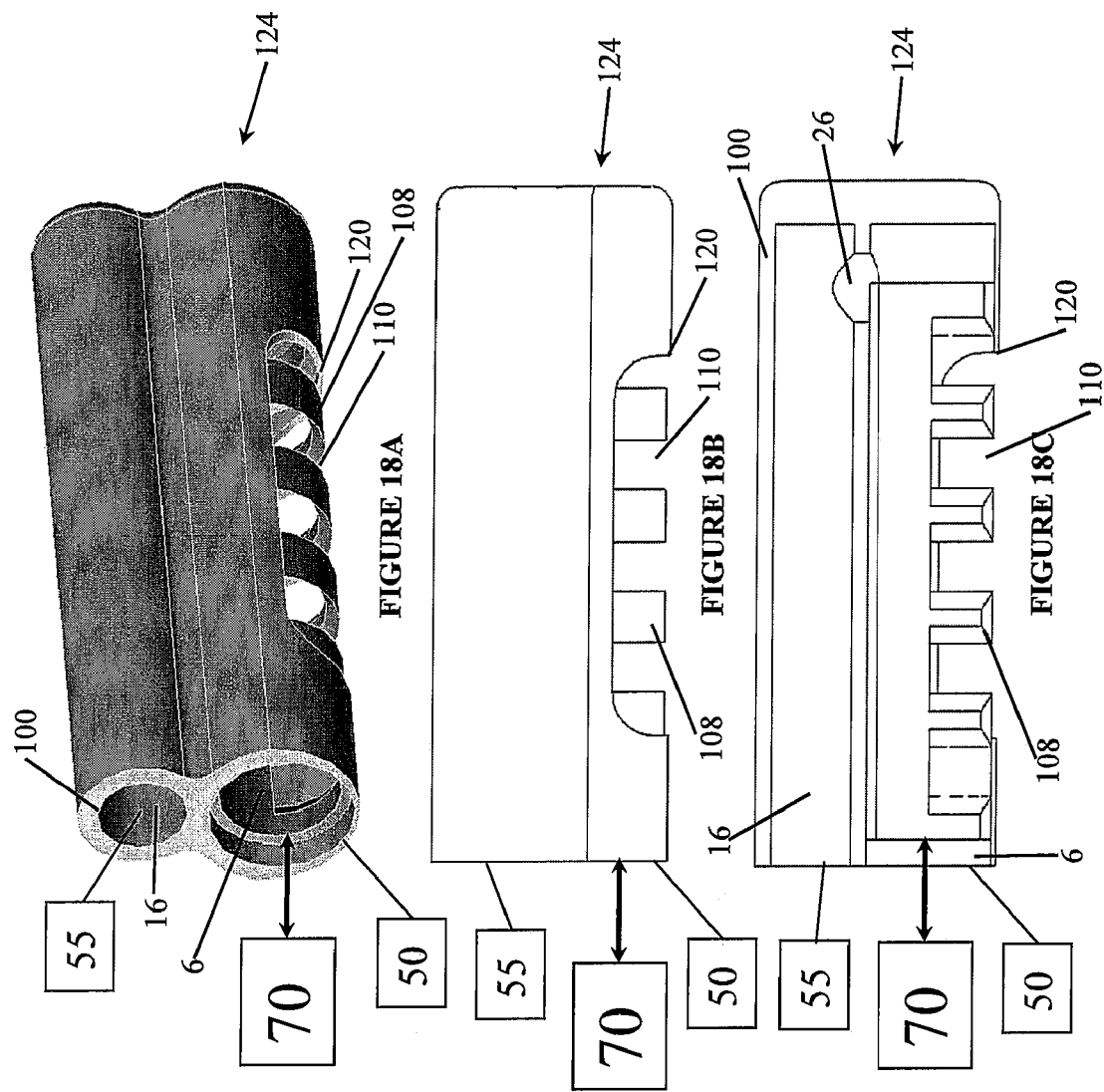
FIGS. 18A to 18C show an isometric view, a side view, and a side-sectional view of the distal end of a vacuum-integrated dissecting tool/coagulation probe variation.

As shown in FIGS. 18A to 18C, an outer covering comprising a multiple lumen tubing defines a vacuum lumen 6 housing a moveable vibrational element 108 that contains windings oriented substantially perpendicular, or at a 45 to 90 degree angle from the axis of the device. The covering maintains adequate rigidity to stabilize the moving vibrational element 108 but is flexible to follow tortuous pathways around the heart and position the aperture 120 through the covering that exposes the windings of and openings 110 between individual windings of the vibrational element 108 against the heart epicardial wall. The vibrational element(s) 108 are couple to a drive shaft that passes along the vacuum lumen 6 and is coupled to a linear motor 70 via a mechanical coupler. The vacuum lumen 6 is coupled to a vacuum source 50. A fluid perfusion lumen 16 defined by the perfusion channel or tube 100 incorporated in the dissecting/tunneling tool is coupled to the vacuum lumen 6 at an outlet 26 to enable passing fluid from a fluid source 55 and along soft tissue contacting the vibrational element(s). This fluid source 55 can comprise a detergent or other pharmacologic agent that facilitates emulsification of adipose (e.g., fat) tissue.

In use, the dissecting/tunneling tool is positioned against fat tissue and the linear motor is activated causing the vibrational element(s) to move axially at a high cycle rate (e.g., 5 kHz to 1 MHz and preferably 15 kHz to 30 kHz) and small displacement (e.g., <5 mm and preferably <1 mm). As such, the fat is locally heated and separated from heart muscle tissue to facilitate removal. The vacuum source 50 is used to constantly pull the separated fat tissue through the vacuum lumen 6 and into a reservoir that collects the fat remnants. This dissecting/tunneling tool 124 is able to adequately remove or separate fat tissue to permit contacting the vacuum-integrated coagulation probe electrode(s)/vibrational element 108 into direct engagement with muscle.

FIGS. 19A to 19G show an isometric view, a side view, a bottom view, a side-sectional view, and three cross-sectional views of an alternative dissecting/tunneling tool 124 that utilizes a rotational vibration element 118 (shown in FIG. 19H) that is coupled to a rotary motor 80 via a drive shaft. The rotary motor 80 produces a high frequency (e.g., 5 kHz to 1 MHz and preferably 15 kHz to 30 kHz) angular displacement (e.g., <90 degrees and preferably <30 degrees) of the rotational vibrational element to separate and remove fat deposits from around the heart. As discussed above, the vibrational element 118 resides within the vacuum lumen 6 defined by the covering such that it engages soft tissue along the aperture 122 created in the side wall of the covering.

Openings 110 between individual windings allow vacuum force to be applied directly to the soft tissue surface and pull soft tissue into engagement with the vibrational element 118. Also, fat tissue that is separated is pulled into the vacuum lumen 6 and is transported into a reservoir coupled to the vacuum source 50. Optional perfusion lumen 16 defined by a perfusion channel or tube 100 allows fluid from a fluid source 55 to pass through an outlet 26 between the perfusion lumen 16 and the vacuum lumen 6, and along soft tissue contacting the dissecting/tunneling tool 124 at the aperture 122 and along the vibrational element 118.

FIGS. 20A to 20D show an isometric view, a side view, a top view, and an end view of another dissecting/tunneling tool 124 variation capable of separating fat tissue. In this variation, two laterally expandable legs 72 oriented along each side of the central drive shaft 76 are connected to a distal segment that incorporates a tapered distal tip 74 to pass between layers of tissue. The tapered distal tip 74 is also connected to the drive shaft 76, which further extends through the shaft 78 of the device to the handle where it is connected to an actuation knob. As the drive shaft 76 is retracted, the legs 72 bow outward laterally and apply dissecting pressure on tissue residing around the legs. The drive shaft 76 may further be coupled to a linear motor to further impart high frequency axial displacement of the tapered distal tip thus the lateral legs to augment the mechanical expansion of the fat tissue layers, which causes separation, with ultrasonic heating and emulsification of fat contacting the tapered distal tip and/or the laterally bowing legs.

The dissecting/tunneling tool 124 may incorporate a guide mechanism 86 that mates with the central lumen 84 of the rail mechanism 62 as discussed above. As such, the dissecting/tunneling tool 124 may be used to position the rail mechanism 62 into the desired location along the heart such that once the desired dissection and/or tunneling has been achieved, the dissecting/tunneling tool 124 may be removed so the vacuum-integrated coagulation probe may be advanced along the rail mechanism 62 and into position against the target soft tissue segment.

FIGS. 21A to 21C show side-sectional views of the variation of the dissecting/tunneling tool 124 in FIGS. 20A to 20D. FIG. 21A shows the tapered distal tip 74 fully extended to compress the legs 72 against the drive shaft 76. FIG. 21B shows tension applied to one of the lateral legs 72 that deflects the tapered distal tip 74 thus steers the distal section of the tool. FIG. 21C shows the drive shaft 76 retracting the tapered distal tip 74 thus expanding the laterally bowing legs 72. The drive shaft that is attached to the tapered distal tip is routed through the central lumen of the shaft 98 and is connected to the handle 94. As the handle 94 is actuated (e.g., squeezed) the drive shaft 76 is retracted causing the tapered distal tip to be retracted and the legs to be bowing laterally outward. As shown in FIGS. 21A to 21C, the lateral legs of this dissecting tool variation are connected to a pivoting member 96 that is further attached to an axially movable knob 92 by a pull-wire. As the pull-wire is advanced, shown in FIG. 21B, the pivoting member rotates and applies tension to the upper lateral leg thereby deflecting the tapered distal tip. If the pull-wire is retracted, not shown, the tapered distal tip Would be deflected in the opposite direction. Alternatively, one or both lateral legs can be routed through the central lumen of the shaft and connected to individual knobs at the handle to be independently actuated.

Figure 22:
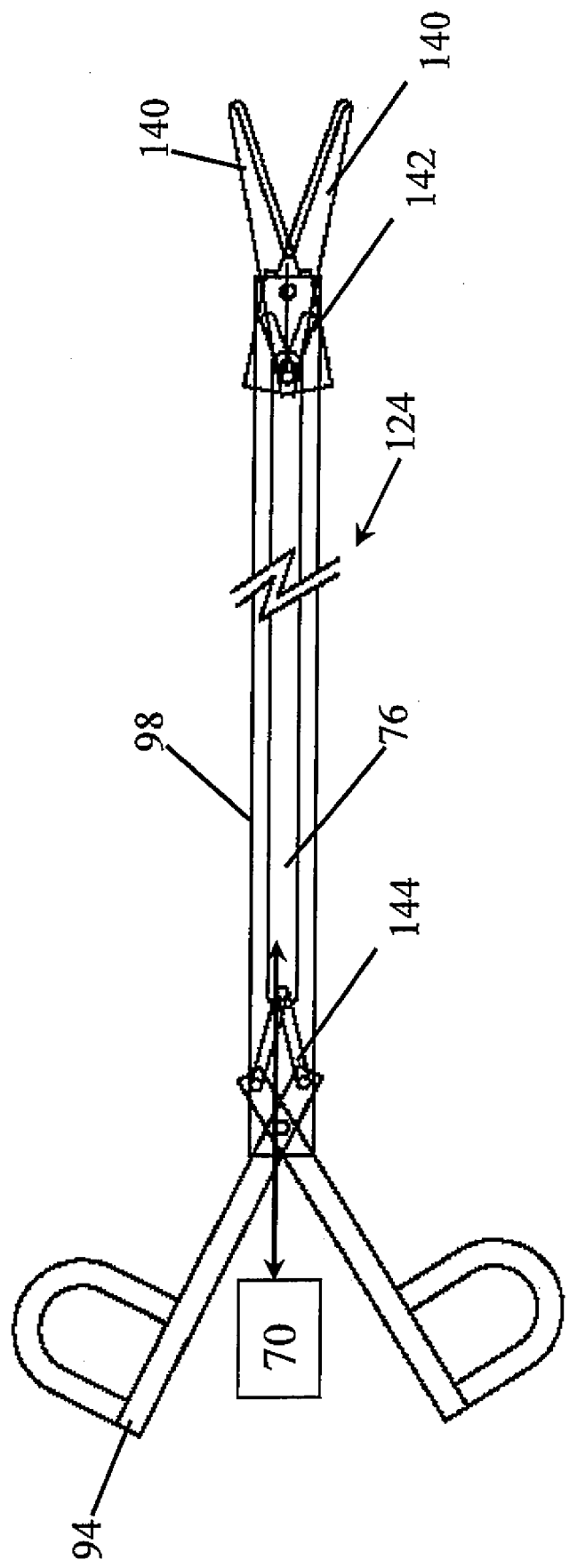
FIG. 22 shows a sectional view of an alternative dissecting/tunneling instrument variation.

FIG. 22 shows an alternative dissecting/tunneling instrument 124 that comprises blunt jaws 140 that pivot relative to each other. The jaws 140 are connected to a drive shaft 76 via links 142 that direct the rotation of the jaws relative to the pivot point. The drive shaft 76 is contained within the shaft 98 that contains a central lumen. The drive shaft 76 connects to the handle arms 94 through proximal links 144 that allow axial movement of the drive shaft as the handle arms are actuated. This dissecting clamp incorporates a mechanical coupler that connects the drive shaft 76 thus the jaws 140 of the dissecting clamp to a linear motor 70 that produces a high frequency displacement causing the dissecting clamp jaws 140 to vibrate and induce an ultrasonic wave capable of separating, emulsifying, or otherwise modifying fat tissue to separate it from muscle tissue. An endoscopic visualization tool may be mounted on the dissecting clamp or inserted through a central lumen in the dissecting clamp to provide direct visualization of the distal end of the dissecting clamp and tissue that is modified with the mechanically-induced ultrasonic dissecting clamp.

Mechanically Vibrating Ultrasonic Ablation Catheters

FIGS. 23A to 23C and FIGS. 24A to 24C show isometric views, side views and top views of two mechanically vibrating ultrasonic ablation catheter variations 150 that access the soft tissue via the vasculature. In these catheter variations, no electrical wire connections are required to transmit energy capable of heating soft tissue to render the tissue electrically non-viable or evoke another heat-induced tissue response.

The catheter variation in FIGS. 23A to 23C comprises a unitary elongate member 152 that passes through a sheath 154 and curves into a reverse spiral emanating from the proximal section 160 of the elongate member. The proximal end of the elongate member is connected to a mechanical vibration mechanism (e.g., linear motor 70 or rotary motor 80), via a mechanical coupler, that moves the distal, curved, expanded section 156 of the elongate member axially or radially at a high frequency (e.g., 5 kHz to 1 MHz and preferably 15 kHz to 30 kHz) and small displacement (<1 mm). The sheath 154 isolates the vibrating elongate member 152, thus the mechanically-induced ultrasonic energy, from surrounding vascular tissue through which the catheter 150 is advanced to access the endocardial soft tissue surface. Because the unitary elongate member 152 utilizes mechanical motion to vibrate and emit ultrasonic energy, the elongate member 152 does not require separate electrodes or transducers. Neither does it require spot welds, solder joints, adhesive bonds, or other attachment processes that stiffen the device or inhibit the ability to bend, expand, or compress the device. Still, a variation of a device according to the invention may include such features.

FIGS. 24A to 24C show another mechanically vibrating ultrasonic ablation catheter 150 variation that incorporates two circular or elliptical loops intersecting into an "X" as shown in FIG. 22B and extending to proximal segments 160 that pass through a sheath 154. This variation of the invention may comprise a unitary member 152 fabricated from a tube laser cut, chemically etched, or otherwise cut into the "X" distal section 158 with proximally extending segments 160. Alternatively, the distal "X" section 158 may be fabricated as one or two components and secured to the proximal segments via attachment processes previously described. Also, the loops of the distal "X" section 158 may comprise separate loops interlaced and bonded at the intersections to form the distal section. For these configurations, the elongate member 152 that defines the mechanically vibrating ultrasonic ablation catheter 150 does not require separate electrodes, transducers, or the requisite bonding processes required to attach electrodes and transducers.

Figure 25B:
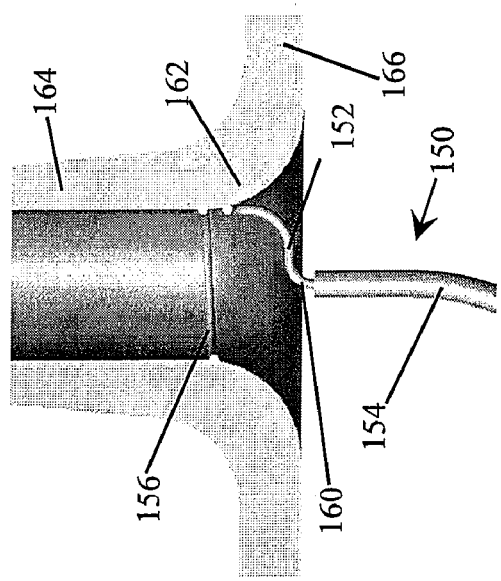
FIGS. 25A and 25B show an isometric view, an end view, and a sectional view of the mechanically vibrating ultrasonic ablation catheter in FIGS. 23A to 23C inside a pulmonary vein.
Figure 25A:
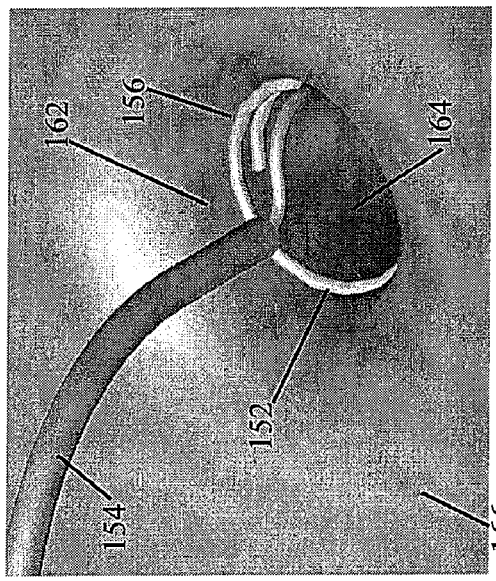

As shown in FIGS. 25A and 25B, the mechanically vibrating ultrasonic ablation catheter 150 variation in FIGS. 23A to 23C is advanced into engagement with a single pulmonary vein 164 and expanded into contact with the orifice 162 of the pulmonary vein to contact atrial tissue at the pulmonary vein 164 such that as the linear motor 70 or rotary motor 80 is actuated, micro-motion of the distal, contacting segment 156 of the catheter at a high cycle rate causes cavitation of adjacent soft tissue thereby heating the atrial tissue at the orifice 162 to the pulmonary vein 164.

Figure 26B:
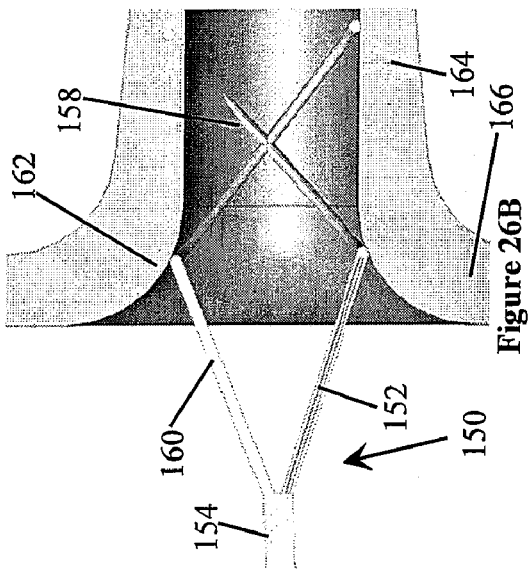
FIGS. 26A and 26B show an isometric view, an end view, and a sectional view of the mechanically vibrating ultrasonic ablation catheter in FIGS. 24A to 24C inside a pulmonary vein.
Figure 26A:
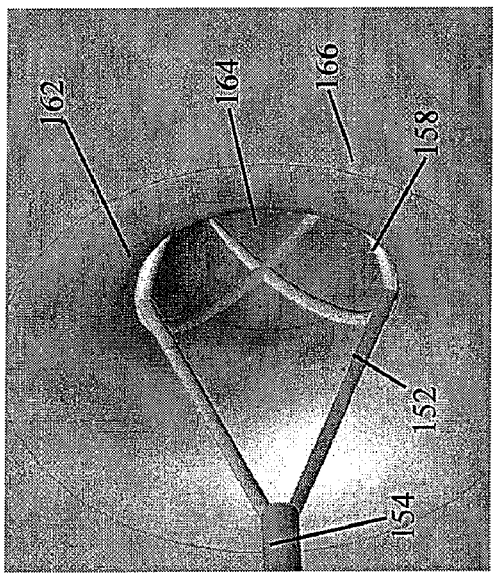

FIGS. 26A and 26B shows the mechanically vibrating ultrasonic catheter 150 variation in FIGS. 24A to 24C inserted at the orifice 162 to the pulmonary vein 164 and expanded into contact with atrial tissue and the pulmonary vein. As described above, actuation of the linear motor 70 or rotary motor 80 causes rapid movement of the distal section 158 causing vibrations that emit an ultrasonic wave capable of causing cavitation and heating of adjacent soft tissue. As the soft tissue heats above 50 degrees Celsius, irreversible conduction block occurs rendering the tissue, adjacent the pulmonary vein and in contact with the mechanically vibrating catheter 150 distal section 158, electrically non-viable and inhibiting cells inside the pulmonary vein 164 from stimulating atrial tissue outside the pulmonary vein 166.

In operation, a transeptal sheath 154 is inserted via conventional techniques through the venous system, through the right atrium, past the interatrial septum at the fossa ovalis, and into the left atrium 166. Once the sheath intravascularly accesses the left atrium, 166 a separate steerable catheter is used to place the distal end of the sheath adjacent or into a pulmonary vein 164. The unitary elongate member 152 that defines the mechanically vibrating ultrasonic ablation catheter 150 is compressed into a small diameter to fit inside the sheath 154. The elongate member 152 is advanced through the sheath 154 and into the pulmonary vein 164 where it extends beyond the distal end of the sheath 154 and expands into contact with the pulmonary vein 164 at the orifice 162. Once positioned, the elongate member 152 can be advanced or retracted to encourage engagement with the orifice 162 to the pulmonary vein 164. The variation in FIGS. 23A to 23C fits against the orifice 162 to the pulmonary vein 164 to circumferentially contact the orifice 162 of the pulmonary vein 164. Alternatively, the distal section 156 can be inserted completely into the pulmonary vein 164.

The variation of the invention in FIGS. 24A to 24C creates a distal section 158 of intersecting loops that has a variable expansion profile such that the proximal end of the distal section 158 expands more than the distal end of the distal section 158 to lock the elongate member 152 into the pulmonary vein 164 and match the contours of the distal section to the orifice 162 of the pulmonary vein 164. The intersecting "X" loops encourage expansion of the distal section 158 into intimate engagement with the orifice 162 of the pulmonary vein 164 (or within the pulmonary vein itself), and ensure that any cross-section of the pulmonary vein 164 is not contacted by the mechanically induced ablation member along more than 90 degrees of the inner circumference of the pulmonary vein 164. As such, the risk of pulmonary vein stenosis due to heat-induced contraction of collagen within the pulmonary vein 164 is mitigated and the degree of contraction is dramatically reduced versus ablation energy transmission configurations that ablate more than 180 degrees around the pulmonary vein 164 at any cross-sectional plane through the pulmonary vein 164. Once the elongate member 152 is expanded into contact with the pulmonary vein 164 and/or orifice 162, the linear motor 70 or rotary motor 80 is activated thereby causing high frequency, small displacement (e.g., <1 mm) of the distal section 158 of the elongate member 152 which causes vibration of the contacted soft tissue and surrounding fluid. This vibration produces an ultrasonic signal capable of heating soft tissue along the orifice 162 of the pulmonary vein 164 or within the pulmonary vein.

As noted herein, variations of the invention may have an elimination of separate electrodes, transducers, electrical wire solder joints or spot welds, and adhesive bonds. In such variations this benefit allows, among others, a decrease in the diameter of the sheath through which the elongate member can be inserted, an improvement in the physical integrity of the ablation catheter, and an increased ability in manipulating the elongate member 152 through the vasculature and into engagement with the orifice 162 to the pulmonary vein 164.

Methods

The methods herein may be performed using the subject devices or by other means. The methods may all comprise the act of providing a suitable device. Such provision may be performed by the end user. In other words, the "providing" (e.g., a delivery system) merely requires the end user obtain, access, approach, position, set-up, activate, power-up, or otherwise act to provide the requisite device in the subject method. Methods recited herein may be carried out in any order of the recited events which is logically possible, as well as in the recited order of events. In addition, variations of the invention may be used in coagulating other soft tissues such as breast tissue, the liver, the prostate, gastrointestinal tissue, skin, or other soft tissue for the coagulation of cancerous cells; or other collagen based soft tissue for the heat induced shrinking or contraction.

Variations

Various exemplary variations of the invention are described below. Reference is made to these examples in a non-limiting sense. They are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein. Exemplary aspects of the invention, together with details regarding material selection and manufacture have been set forth above. As for other details of the present invention, these may be appreciated in connection with the above-referenced patents and publications as well as generally know or appreciated by those with skill in the art.

The same may hold true with respect to method-based aspects of the invention in terms of additional acts as commonly or logically employed. In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "an," "said," and "the" include plural referents unless the specifically stated otherwise. In other words, use of these articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims.

What is claimed is:

1. A method of creating a lesion on an irregular surface of soft tissue, the method comprising:
   advancing a treatment device to the irregular surface, where the treatment device comprises an opening exposing an electrode, the treatment device also comprising a vacuum lumen in fluid communication with a vacuum source and a fluid perfusion lumen in fluid communication with a fluid source, where both the vacuum lumen and fluid perfusion lumen are fluidly coupled to the opening;
   drawing a vacuum in the vacuum source to cause a drop in pressure in both the vacuum lumen and the opening, whereupon placing the opening against the soft tissue creates a seal against the soft tissue to cause the fluid perfusion lumen to drop in pressure resulting in fluid flow from the fluid source through the fluid perfusion lumen across the opening and through the vacuum lumen, where when uncovered the opening prevents the perfusion lumen from reducing in pressure preventing fluid flow; and
   energizing the electrode during the fluid flow to create the lesion in the irregular surface of soft tissue.

2. The method of claim 1, where energizing the electrode during the fluid flow to create the lesion in the irregular surface of soft tissue comprises applying RF energy to the electrode to create a contiguous transmural lesion in atrial tissue.

3. The method of claim 2, where creating the contiguous transmural lesion comprises creating a series of contiguous transmural lesions.

4. The method of claim 2, where advancing the treatment device to the irregular surface of soft tissue comprises advancing the treatment device to a plurality of regions to create a pattern of lesions in atrial tissue.

5. The method of claim 2, where the RF energy comprises a unipolar mode, and further comprising placing a reference element in electrical contact with tissue.

6. The method of claim 2, where the RF energy comprises a bipolar mode.

7. The method of claim 1, where advancing the treatment device to the irregular surface the soft tissue comprises advancing the treatment device to a liver, prostate, colon, esophagus, gastrointestinal region, and gynecological region.

8. The method of claim 1, where advancing the treatment device to the irregular surface of the soft tissue comprises advancing the treatment device during a procedure selected from the group consisting of an arthroscopic, laparoscopic, and other minimally invasive procedure.

9. The method of claim 1, where energizing the electrode during the fluid flow to create the lesion in the irregular surface of soft tissue comprises applying vibrational energy to the electrode to create a contiguous transmural lesion in atrial tissue.

10. The method of claim 1, where the electrode has a length and conforms to the irregular surface of soft tissue to create a curvilinear lesion.

11. The method of claim 1, where a portion of the treatment device housing the electrode is pre-shapeable to assume a shape and where the lesion forms the shape.

12. The method of claim 1, further comprising advancing a track adjacent to the irregular surface and where advancing the treatment device to the irregular surface comprises advancing the treatment device over the track.

13. The method of claim 12, where the track comprises a device selected from the group consisting of a wire, a steerable catheter, a steerable guide-wire, a shaped tube, and a shaped mandrel.

14. A method of creating a curvilinear lesion along an irregular tissue surface, the method comprising:
   advancing a treatment device to the irregular surface, where the treatment device comprises an opening exposing an electrode having a length, the treatment device also comprising a vacuum lumen coupled to a vacuum source and a fluid perfusion lumen coupled to a fluid source, where both the vacuum lumen and fluid perfusion lumen are fluidly coupled to the opening;
   drawing a vacuum in the vacuum source to drop pressure in both the vacuum lumen and the opening, such that when the opening is placed against the irregular tissue surface, the tissue surface forms a seal against the opening, where formation of the seal drops pressure in the fluid perfusion lumen causing fluid flow from the fluid source through the fluid perfusion lumen across the opening and through the vacuum lumen; and
   energizing the electrode during the fluid flow to create the linear lesion along the length of the electrode in the irregular tissue surface.

15. The method of claim 14, where energizing the electrode during the fluid flow to create the lesion in the irregular surface of soft tissue comprises applying RF energy to the electrode to create a contiguous transmural lesion in atrial tissue.

16. The method of claim 15, where creating the contiguous transmural lesion comprises creating a series of contiguous transmural lesions.

17. The method of claim 15, where advancing the treatment device to the irregular surface of soft tissue comprises advancing the treatment device to a plurality of regions to create a pattern of lesions in atrial tissue.

18. The method of claim 15, where the RF energy comprises a unipolar mode, and further comprising placing a reference element in electrical contact with tissue.

19. The method of claim 15, where the RF energy comprises a bipolar mode.

20. The method of claim 1, where advancing the treatment device to the irregular surface the soft tissue comprises advancing the treatment device to a liver, prostate, colon, esophagus, gastrointestinal region, and gynecological region.

21. The method of claim 14, where advancing the treatment device to the irregular surface of the soft tissue comprises advancing the treatment device during a procedure selected from the group consisting of an arthroscopic, laparoscopic, and other minimally invasive procedure.

22. The method of claim 14, where energizing the electrode during the fluid flow to create the lesion in the irregular surface of soft tissue comprises applying vibrational energy to the electrode to create a contiguous transmural lesion in atrial tissue.

23. The method of claim 14, where a portion of the treatment device housing the electrode is pre-shapeable to assume a shape and where the lesion forms the shape.

24. The method of claim 14, further comprising advancing a track adjacent to the irregular surface and where advancing the treatment device to the irregular surface comprises advancing the treatment device over the track.

25. The method of claim 24, where the track comprises a device selected from the group consisting of a wire, a steerable catheter, a steerable guide-wire, a shaped tube, and a shaped mandrel.

26. A method of treating soft tissue, with a treatment device having a fluid circuit comprising a vacuum lumen fluidly coupled to a vacuum source, a perfusion lumen fluidly coupled to a fluid source, and an opening in the device fluidly coupled to both the perfusion lumen and the vacuum lumen, where the opening also contains an electrode, the method comprising:
  applying vacuum to the vacuum lumen, where the opening causes the fluid circuit to be an open fluid circuit through which no fluid flow can occur;
  closing the fluid circuit by placing the opening against soft tissue to form a seal against the soft tissue, where closing the fluid circuit causes fluid from the fluid source to flow in the fluid circuit; and
  energizing the electrode to treat the soft tissue during fluid flow by confirming engagement of the electrode against tissue in the opening using the fluid flow.

27. The method of claim 26, where applying vacuum occurs after closing the fluid circuit.

28. The method of claim 26, where energizing the electrode during the fluid flow to treat the soft tissue comprises applying RF energy to the electrode to create a contiguous transmural lesion in atrial tissue.

29. The method of claim 28, where creating the contiguous transmural lesion comprises creating a series of contiguous transmural lesions.

30. The method of claim 28, where the RF energy comprises a unipolar mode, and further comprising placing a reference element in electrical contact with tissue.

31. The method of claim 28, where the RF energy comprises a bipolar mode.

32. The method of claim 26, where advancing the treatment device to the irregular surface the soft tissue comprises advancing the treatment device to a liver, prostate, colon, esophagus, gastrointestinal region, and gynecological region.

33. The method of claim 26, where advancing the treatment device to the irregular surface of the soft tissue comprises advancing the treatment device during a procedure selected from the group consisting of an arthroscopic, laparoscopic, and other minimally invasive procedure.

34. The method of claim 26, where energizing the electrode during the fluid flow to create the lesion in the irregular surface of soft tissue comprises applying vibrational energy to the electrode to create a contiguous transmural lesion in atrial tissue.

35. The method of claim 26, where the electrode has a length and conforms to the irregular surface of soft tissue to create a curvilinear lesion.

36. The method of claim 26, where a portion of the treatment device housing the electrode is pre-shapeable to assume a shape and where the lesion forms the shape.

37. The method of claim 26, further comprising advancing a track adjacent to the irregular surface and where advancing the treatment device to the irregular surface comprises advancing the treatment device over the track.

38. The method of claim 37, where the track comprises a device selected from the group consisting of a wire, a steerable catheter, a steerable guide-wire, a shaped tube, and a shaped mandrel.

* * * * *